(12) United States Patent
Piran et al.

(10) Patent No.: US 8,937,082 B2
(45) Date of Patent: Jan. 20, 2015

(54) NILOTINIB SALTS AND CRYSTALLINE FORMS THEREOF

(75) Inventors: Maytal Piran, Rishon Le Zion (IL); Jacob Rendell, Beer Sheva (IL)

(73) Assignee: Teva Pharmaceutical Industries Ltd., Petach Tikva (IL)

(*) Notice: Subject to any disclaimer, the term of this patent is extended or adjusted under 35 U.S.C. 154(b) by 73 days.

(21) Appl. No.: 13/806,069

(22) PCT Filed: Jun. 21, 2011

(86) PCT No.: PCT/US2011/041242
§ 371 (c)(1),
(2), (4) Date: Mar. 8, 2013

(87) PCT Pub. No.: WO2011/163222
PCT Pub. Date: Dec. 29, 2011

(65) Prior Publication Data
US 2013/0158059 A1    Jun. 20, 2013

Related U.S. Application Data

(60) Provisional application No. 61/356,771, filed on Jun. 21, 2010, provisional application No. 61/359,469, filed on Jun. 29, 2010, provisional application No. 61/360,064, filed on Jun. 30, 2010, provisional application No. 61/361,691, filed on Jul. 6, 2010, provisional application No. 61/365,510, filed on Jul. 19, 2010, provisional application No. 61/375,013, filed on Aug. 18, 2010, provisional application No. 61/376,213, filed on Aug. 23, 2010, provisional application No. 61/380,428, filed on Sep. 7, 2010, provisional application No. 61/382,136, filed on Sep. 13, 2010, provisional application No. 61/384,428, filed on Sep. 20, 2010, provisional application No. 61/392,266, filed on Oct. 12, 2010, provisional application No. 61/405,301, filed on Oct. 21, 2010, provisional application No. 61/410,202, filed on Nov. 4, 2010, provisional application No. 61/434,561, filed on Jan. 20, 2011.

(51) Int. Cl.
*C07D 401/14* (2006.01)
*A61K 31/506* (2006.01)
*A61K 31/4178* (2006.01)

(52) U.S. Cl.
CPC ............ *C07D 401/14* (2013.01); *A61K 31/506* (2013.01); *A61K 31/4178* (2013.01)
USPC .......................................... 514/275; 544/331

(58) Field of Classification Search
CPC .......................... C07D 401/14; A61K 31/4178
USPC .......................................... 544/331; 514/275
See application file for complete search history.

(56) References Cited

U.S. PATENT DOCUMENTS 7,169,791 B2    1/2007    Breitenstein et al.

FOREIGN PATENT DOCUMENTS

| WO | WO 2004/005281 | * | 1/2004 |
|---|---|---|---|
| WO | WO 2007/015870 A2 | | 2/2007 |
| WO | WO 2007/015871 A1 | | 2/2007 |
| WO | WO2007/072087 | | 6/2007 |
| WO | WO 2010/054056 A2 | | 5/2010 |
| WO | WO 2011/033307 A1 | | 3/2011 |

OTHER PUBLICATIONS

Simone, Oncology: Introduction, Cecil Textbook of Medicine, 20th Edition, vol. 1, pp. 1004-1010, 1996.*
International Search Report dated Oct. 26, 2011 issued in related PCT Application No. PCT/US2011/041242.

* cited by examiner

*Primary Examiner* — Deepak Rao
(74) *Attorney, Agent, or Firm* — Baker & Hostetler LLP

(57) ABSTRACT

Nilotinib salts and crystalline forms thereof have been prepared and characterized.

29 Claims, 74 Drawing Sheets

An X-ray powder diffractogram of Nilotinib oxalate crystalline form I (peak at 28.45 corresponds to the silicon standard).

NILOTINIB SALTS AND CRYSTALLINE FORMS THEREOF

CROSS-REFERENCED TO RELATED APPLICATION

This application is a National Stage entry of International Application PCT/US2011/041242, filed Jun. 21, 2011, which claims the benefit of priority to U.S. Provisional Patent Application Ser. Nos. 61/356,771, filed Jun. 21, 2010; 61/359,469, filed Jun. 29, 2010; 61/360,064, filed Jun. 30, 2010; 61/361, 691, filed Jul. 6, 2010; 61/365,510, filed Jul. 19, 2010; 61/375, 013, filed Aug. 18, 2010; 61/376,213, filed Aug. 23, 2010; 61/380,428, filed Sep. 7, 2010; 61/382,136, filed Sep. 13, 2010; 61/384,428, filed Sep. 20, 2010; 61/392,266, filed Oct. 12, 2010; 61/405,301, filed Oct. 21, 2010; 61/410,202, filed Nov. 4, 2010; and 61/434,561, filed Jan. 20, 2011, which are incorporated herein by reference.

FIELD OF THE INVENTION

The present invention is directed to Nilotinib salts and crystalline forms of Nilotinib salts.

BACKGROUND OF THE INVENTION

Nilotinib, 4-methyl-N-[3-(4-methyl-1H-imidazol-1-yl)-5-(trifluoromethyl)-phenyl]-3-[[4-(3-pyridinyl)-2-pyrimidinyl]amino]-benzamide, having the following formula:

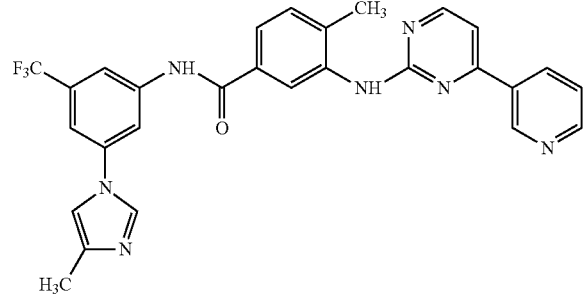 [SMILES: Cc1cn(-c2cc(NC(=O)c3ccc(C)c(Nc4nccc(-c5cccnc5)n4)c3)cc(C(F)(F)F)c2)cn1]

is a tyrosine kinase inhibitor used for the treatment of drug-resistant chronic myelogenous leukemia (CML), and in particular, for the treatment of chronic phase and accelerated phase Philadelphia chromosome positive CML in adult patients whose disease has progressed, or who cannot tolerate other therapies that include imatinib. Nilotinib is administered as a hydrochloride salt in the form of capsules that are marketed in the USA and the EU under the name Tasigna®.

PCT publications WO 2007/015870 ("WO '870") and WO 2007/015871 ("WO '871") describe several Nilotinib salts, including crystalline and amorphous forms of nilotinib free base, Nilotinib hydrochloride and Nilotinib Sulfate. The crystalline forms exist in either solvate, anhydrous or hydrate forms. PCT publication no. WO 2007/015870 (WO '870) describes crystalline forms of nilotinib including Nilotinib HCl crystalline form A. PCT publication no. WO 2010/054056 ('WO '056') describes crystalline forms of nilotinib HCl including Nilotinib HCl crystalline forms T17, T18 and T19. PCT publication no. WO 2011/033307 describes Nilotinib dihydrochloride salt and a crystalline form thereof.

The disclosures of each and every patent, patent application, and publication cited herein are hereby incorporated herein by reference in their entirety.

The present invention relates to salts of Nilotinib; 4-methyl-N-[3-(4-methyl-1H-imidazol-1-yl)-5-(trifluoromethyl) phenyl]-3-[[4-(3-pyridinyl)-2-pyrimidinyl]amino]-benzamide and their solid state forms. The salts are selected from: Nilotinib HCl, Nilotinib fumarate, Nilotinib 2-chloromandelate, Nilotinib succinate, Nilotinib adipate, Nilotinib L-tartrate, Nilotinib glutarate, Nilotinib p-toluenesulfonate, Nilotinib camphorsulfonate, Nilotinib glutamate, Nilotinib palmitate, Nilotinib quinate, Nilotinib citrate, Nilotinib maleate, Nilotinib acetate, Nilotinib L-malate, Nilotinib L-aspartate, Nilotinib formate, Nilotinib hydrobromide, Nilotinib oxalate and Nilotinib malonate. The nature of the solid form can be influenced by controlling the conditions under which the above 4-methyl-N-[3-(4-methyl-1H-imidazol-1-yl)-5-(trifluoromethyl)phenyl]-3-[[4-(3-pyridinyl)-2-pyrimidinyl] amino]-benzamide salts are obtained. Preferably, the present invention relates to solid state forms of Nilotinib hydrobromide and Nilotinib L-tartrate.

Polymorphism, the occurrence of different crystal forms, is a property of some molecules and molecular complexes. A single molecule may give rise to a variety of polymorphs having distinct crystal structures and physical properties like melting point, thermal behaviors (e.g. measured by thermogravimetric analysis—(TGA), or differential scanning calorimetry—(DSC)), X-ray powder diffraction (XRPD) pattern, infrared absorption fingerprint, and solid state nuclear magnetic resonance (NMR) spectrum. One or more of these techniques may be used to distinguish different polymorphic forms of a compound.

Discovering new salts and new polymorphic forms and solvates of a pharmaceutical product can provide materials having desirable processing properties, such as ease of handling, ease of processing, storage stability, ease of purification or as desirable intermediate crystal forms that facilitate conversion to other polymorphic forms. New polymorphic forms and solvates of a pharmaceutically useful compound or salts thereof can also provide an opportunity to improve the performance characteristics of a pharmaceutical product. It enlarges the repertoire of materials that a formulation scientist has available for formulation optimization, for example by providing a product with different properties, e.g., better processing or handling characteristics, improved dissolution profile, or improved shelf-life. For at least these reasons, there is a need for additional polymorphs of Nilotinib salts.

SUMMARY OF THE INVENTION

In one embodiment the present invention provides a Nilotinib salt selected from: Nilotinib 2-chloromandelate, Nilotinib succinate, Nilotinib adipate, Nilotinib glutarate, Nilotinib camphorsulfonate, Nilotinib glutamate, Nilotinib palmitate, Nilotinib quinate, Nilotinib acetate, Nilotinib L-malate, Nilotinib L-aspartate, Nilotinib formate, Nilotinib hydrobromide and Nilotinib oxalate. Preferably, the Nilotinib salt is selected from: Nilotinib succinate, Nilotinib glutamate, Nilotinib acetate and Nilotinib L-malate. More preferably, the Nilotinib salt is Nilotinib hydrobromide.

In another embodiment the present invention relates to the solid state forms of salts of Nilotinib, 4-methyl-N-[3-(4-methyl-1H-imidazol-1-yl)-5-(trifluoromethyl)phenyl]-3-[[4-(3-pyridinyl)-2-pyrimidinyl]amino]-benzamide, selected from: Nilotinib HCl, Nilotinib fumarate, Nilotinib 2-chloromandelate, Nilotinib succinate, Nilotinib adipate, Nilotinib L-tartrate, Nilotinib glutarate, Nilotinib p-toluenesulfonate, Nilotinib camphor-sulfonate, Nilotinib glutamate, Nilotinib palmitate, Nilotinib quinate, Nilotinib citrate, Nilotinib maleate, Nilotinib acetate, Nilotinib L-malate, Nilotinib L-aspartate, Nilotinib formate, Nilotinib hydrobromide, Nilotinib oxalate and Nilotinib malonate. Preferably, the present invention relates to solid state forms of Nilotinib hydrobromide, Nilotinib L-tartrate, Nilotinib succinate, Nilotinib glutamate, Nilotinib acetate and Nilotinib L-malate, more preferably, to solid state forms of Nilotinib hydrobromide, Nilotinib L-tartrate.

In another embodiment the present invention encompasses the above salts and solid state forms of Nilotinib for use in the preparation of Nilotinib base, Nilotinib hydrochloride, or of pharmaceutical compositions of Nilotinib salts, including but not limited to Nilotinib hydrochloride. Preferably, the salts and solid state forms of Nilotinib described herein are used for preparing Nilotinib monohydrochloride, in hydrated (e.g. monohydrate) or anhydrous form, or pharmaceutical compositions thereof, particularly Nilotinib monohydrochloride monohydrate or pharmaceutical compositions thereof.

In another embodiment, the present invention provides the use of any of the above pharmaceutical compositions for the treatment of drug-resistant CML. In another embodiment, the invention provides a method of treating drug-resistant CML, comprising administering a therapeutically effective amount of at least one of the above crystal forms or at least one of the above pharmaceutical compositions to a person suffering from CML.

In another embodiment, the invention provides any form of Nilotinib as described above as a medicament. Preferably, the invention provides a form of Nilotinib as described above for the treatment of CML.

In yet another embodiment, the present invention also provides a process for preparing Nilotinib HCl, by preparing any one of the Nilotinib salts and crystalline forms thereof, and converting it to Nilotinib HCl or a hydrate (e.g., a monohydrate) thereof, preferably Nilotinib monohydrochloride, and more particularly Nilotinib monohydrochloride monohydrate. In yet another embodiment, the present invention also provides a process for preparing Nilotinib base, by preparing any one of the Nilotinib salts and crystalline forms thereof, and converting it to Nilotinib base.

DETAILED DESCRIPTION OF THE INVENTION

Figure 1:
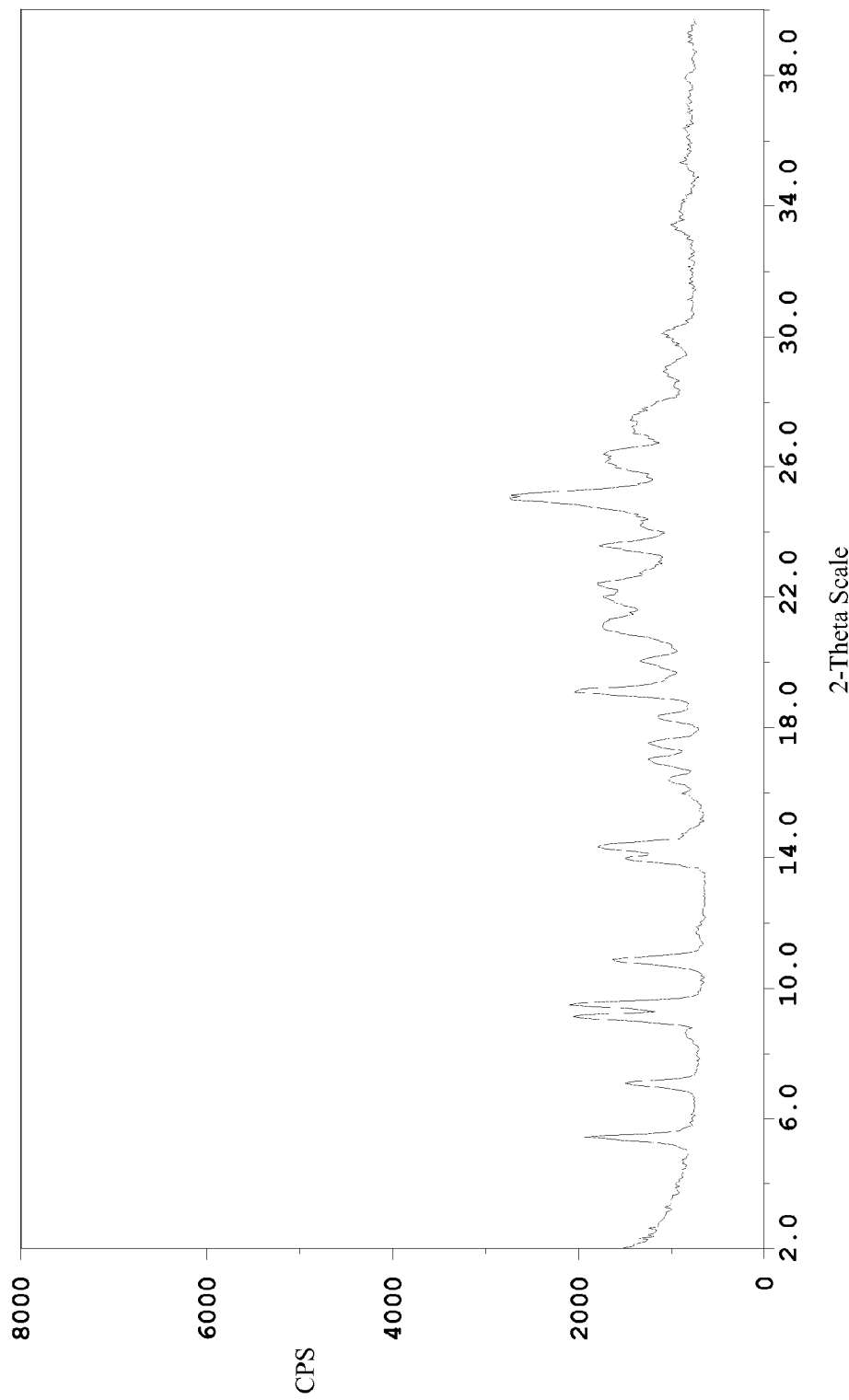
FIG. 1 shows an X-ray powder diffractogram of nilotinib HCl crystalline form T20, prepared according to example 1.

The present invention addresses a need in the art by providing new Nilotinib salts selected from: Nilotinib 2-chloromandelate, Nilotinib succinate, Nilotinib adipate, Nilotinib glutarate, Nilotinib camphorsulfonate, Nilotinib glutamate, Nilotinib palmitate, Nilotinib quinate, Nilotinib acetate, Nilotinib L-malate, Nilotinib L-aspartate, Nilotinib formate, Nilotinib hydrobromide and Nilotinib oxalate, and crystalline forms thereof, as well as new crystalline forms of Nilotinib HCl, Nilotinib fumarate, Nilotinib L-tartrate, Nilotinib p-toluenesulfonate, Nilotinib citrate, Nilotinib acetate, Nilotinib L-malate, Nilotinib L-aspartate, Nilotinib formate, Nilotinib hydrobromide, Nilotinib malonate and Nilotinib oxalate.

In some embodiments, the polymorphs of the above Nilotinib salts of the invention are substantially free of any other polymorphic forms, or of specified polymorphic forms of the Nilotinib salt. In any embodiment of the present invention, by "substantially free" is meant that the forms of the present invention contain 20% (w/w) or less, 10% (w/w) or less, 5% (w/w) or less, 2% (w/w) or less, particularly 1% (w/w) or less, more particularly 0.5% (w/w) or less, and most particularly 0.2% (w/w) or less of either any other polymorphs, or of a specified polymorph or polymorphs of the Nilotinib salt. In other embodiments, the polymorphs of Nilotinib salts of the invention contain from 1% to 20% (w/w), from 5% to 20% (w/w), or from 5% to 10% (w/w) of any other polymorphs or of a specified polymorph or polymorphs of the Nilotinib salt.

The salts and solid state forms of the present invention have advantageous properties including at least one of: high crystallinity, solubility, dissolution rate, morphology, thermal and mechanical stability to polymorphic conversion and/or to dehydration, storage stability, low content of residual solvent, a lower degree of hygroscopicity, flowability, and advantageous processing and handling characteristics such as compressibility, and bulk density.

A crystal form may be referred to herein as being characterized by graphical data "as depicted in" a figure. Such data include, for example, powder X-ray diffractograms and solid state NMR spectra. The skilled person will understand that such graphical representations of data may be subject to small variations, e.g., in peak relative intensities and peak positions due to factors such as variations in instrument response and variations in sample concentration and purity, which are well known to the skilled person. Nonetheless, the skilled person would readily be capable of comparing the graphical data in the Figures herein with graphical data generated for an unknown crystal form and confirm whether the two sets of graphical data are characterizing the same crystal form or two different crystal forms.

As used herein, unless stated otherwise, the XRPD measurements are taken using copper Kα radiation wavelength 1.5418 Å.

As used herein, the term "anhydrous" refers to a crystalline form having less than about 1% total water or any other solvent by weight (bound and unbound) by Karl Fisher titration.

As used herein and unless indicated otherwise, the term "solvate" refers to a crystal form that incorporates a solvent in the crystal structure. When the solvent is water, the solvate is often referred to as a "hydrate." The solvent in a solvate may be present in either a stoichiometric or in a non-stoichiometric amount.

As used herein, the term "isolated" in reference to any of Nilotinib salts or polymorphs thereof of the present invention corresponds to Nilotinib salt or polymorph thereof that is physically separated from the reaction mixture, where it is formed.

As used herein, the term "wet crystalline form" refers to a polymorph that was not dried using any conventional techniques to remove residual solvent.

As used herein, the term "dry crystalline form" refers to a polymorph that was dried using any conventional techniques.

A thing, e.g., a reaction mixture, may be characterized herein as being at, or allowed to come to "room temperature", often abbreviated "RT." This means that the temperature of the thing is close to, or the same as, that of the space, e.g., the room or fume hood, in which the thing is located. Typically, room temperature is from about 15° C. to about 30° C., or about 20° C. to about 25° C., or about 25° C.

A process or step may be referred to herein as being carried out "overnight." This refers to a time interval, e.g., for the process or step, that spans the time during the night, when that process or step may not be actively observed. This time interval is from about 8 to about 20 hours, or about 10-18 hours, typically about 16 hours.

As used herein, the term "absolute ethanol" refers to ethanol having 1% (weight/weight percentage) or less of water, or 0.5% or less of water, particularly, 0.25% or less of water, more particularly, 0.15% or less of water.

The amount of solvent employed in a chemical process, e.g., a reaction or a crystallization, may be referred to herein as a number of "volumes" or "vol" or "V." For example, a material may be referred to as being suspended in 10 volumes (or 10 vol or 10V) of a solvent. In this context, this expression would be understood to mean milliliters of the solvent per gram of the material being suspended, such that suspending a 5 grams of a material in 10 volumes of a solvent means that the solvent is used in an amount of 10 milliliters of the solvent per gram of the material that is being suspended or, in this example, 50 mL of the solvent. In another context, the term "v/v" may be used to indicate the number of volumes of a solvent that are added to a liquid mixture based on the volume of that mixture. For example, adding MTBE (1.5 v/v) to a 100 ml reaction mixture would indicate that 150 mL of MTBE was added.

As used herein, the term "chemical shift difference" refers to the difference in chemical shifts between a reference signal and another signal in the same NMR spectrum. These chemical shift differences serve to provide an additional analytical measurement for a substance, for example a nilotinib salt of the present invention, which will compensate for a phenomenon that may occur in NMR spectroscopy wherein a shift in the solid-state NMR "fingerprint" is observed. Such a shift in the NMR peaks may occur, for example as a result of variations in the instrumentation, the temperature, or the calibration method used in the NMR analysis. This shift in the solid-state NMR "fingerprint", having chemical shift resonances at a certain positions, is such that even though the individual chemical shifts of signals have moved, all the peaks in the spectrum are moved by the same amount, such that the difference between chemical shifts of each signal and another is retained and may be used as a reliable characterization of the material being analyzed.

In the present patent application, the chemical shift differences were calculated by subtracting the chemical shift value of the signal exhibiting the lowest chemical shift (reference signal) in the solid state $^{13}$C NMR spectrum in the range of 100 to 180 ppm from chemical shift value of another (observed) signal in the same $^{13}$C NMR spectrum in the range of 100 to 180 ppm.

As used herein Nilotinib HCl Form A refers to a crystalline form as described in WO '870, which is characterized by an X-ray powder diffraction pattern having at least one, more preferably at least two, still more preferably at least four and most preferably all maxima selected from about 8.5, 11.0, 11.5, 17.2, 18.8, 19.2, 20.8, 22.1 and 26.0 degrees two theta±0.2 degrees two theta.

As used herein Nilotinib HCl Form T17 refers to a crystalline form which is characterized by an X-ray powder diffraction pattern having peaks at 5.7, 9.8, 15.0, 15.8 and 17.3 degrees two theta±0.2 degrees two theta. Nilotinib HCl Form T17 may be further characterized by x-ray powder diffraction pattern having additional peaks at about 7.5, 11.4, 18.6, 19.6 and 20.7 degrees two theta±0.2 degrees two theta or at about 7.6, 11.4, 18.7, 19.7 and 20.7 degrees two theta±0.2 degrees two theta.

As used herein Nilotinib HCl Form T18 refers to a crystalline form which is characterized by an X-ray powder diffraction pattern having peaks at 5.5, 7.2, 8.7, 9.6 and 10.9 degrees two theta±0.2 degrees two theta, or an X-ray powder diffraction pattern having peaks at 5.5, 7.1, 8.7, 9.6 and 10.9 degrees two theta±0.2 degrees two theta. Nilotinib HCl Form T18 may be further characterized by additional X-ray powder diffraction peaks at 14.4, 17.0, 19.2, 21.9 and 22.3 degrees two theta±0.2 degrees two theta or at 14.4, 17.0, 19.2, 21.9 and 22.4 degrees two theta±0.2 degrees two theta.

As used herein Nilotinib HCl Form T19 refers to a crystalline form which is characterized by an X-ray powder diffraction pattern having peaks at 5.5, 7.2, 9.2, 9.6 and 10.9 degrees two theta±0.2 degrees two theta; Nilotinib HCl Form T19 may be further characterized by additional X-ray powder diffraction peaks at 14.1, 14.9, 17.7, 18.5 and 19.3 degrees two theta±0.2 degrees two theta.

Preferably, the Nilotinib hydrochloride forms according to any embodiment of the present invention (i.e. Forms T20, T27, T28 and T29) are substantially free of other known forms of Nilotinib hydrochloride, particularly Forms A, B, T17, T18 and T19 as defined above, wherein the term "substantially free" is as defined above.

The present invention provides new Nilotinib salts selected from: Nilotinib 2-chloromandelate, Nilotinib succinate, Nilotinib adipate, Nilotinib glutarate, Nilotinib camphorsulfonate, Nilotinib glutamate, Nilotinib palmitate, Nilotinib quinate, Nilotinib acetate, Nilotinib L-malate, Nilotinib L-aspartate, Nilotinib formate and Nilotinib hydrobromide. The above salts can be isolated. Preferably, the above salts are in crystalline form.

Figure 2:
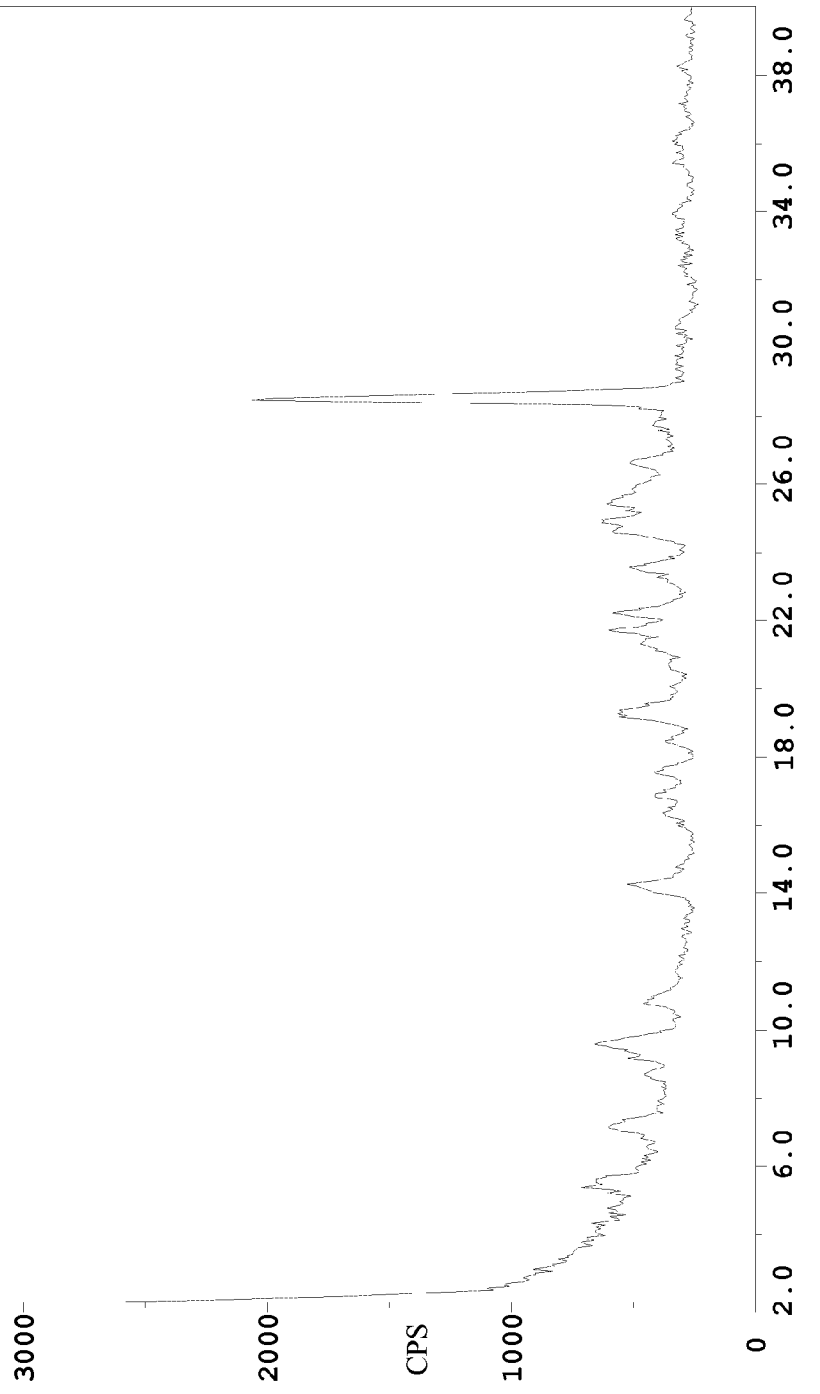
FIG. 2 shows an X-ray powder diffractogram of nilotinib HCl crystalline form T20, prepared according to example 3.

The present invention encompasses crystalline Nilotinib hydrochloride (HCl), designated as form T20. Form T20 can be characterized by data selected from: an X-ray powder diffraction pattern having peaks at 5.3, 7.0, 14.4, 20.1 and 21.1 degrees two theta±0.2 degrees two theta; an X-ray powder diffraction pattern substantially as depicted in FIG. 1; an X-ray powder diffraction pattern substantially as depicted in FIG. 2; and combinations thereof. Nilotinib HCl Form T20 may be further characterized by data selected from: an X-ray powder diffraction pattern having additional peaks at 9.1, 10.9, 19.1, 22.5 and 25.0 degrees two theta±0.2 degrees two theta; a FT-IR spectrum having peaks at 745, 803, 998, 1124, 1352, 1378, 1462 and 1525 cm$^{-1}$±2 cm$^{-1}$; a FT-IR spectrum having peaks at 749, 798, 869, 969, 1378, 1399, 1455 and 1583 cm$^{-1}$±2 cm$^{-1}$; and combinations thereof.

Figure 3:
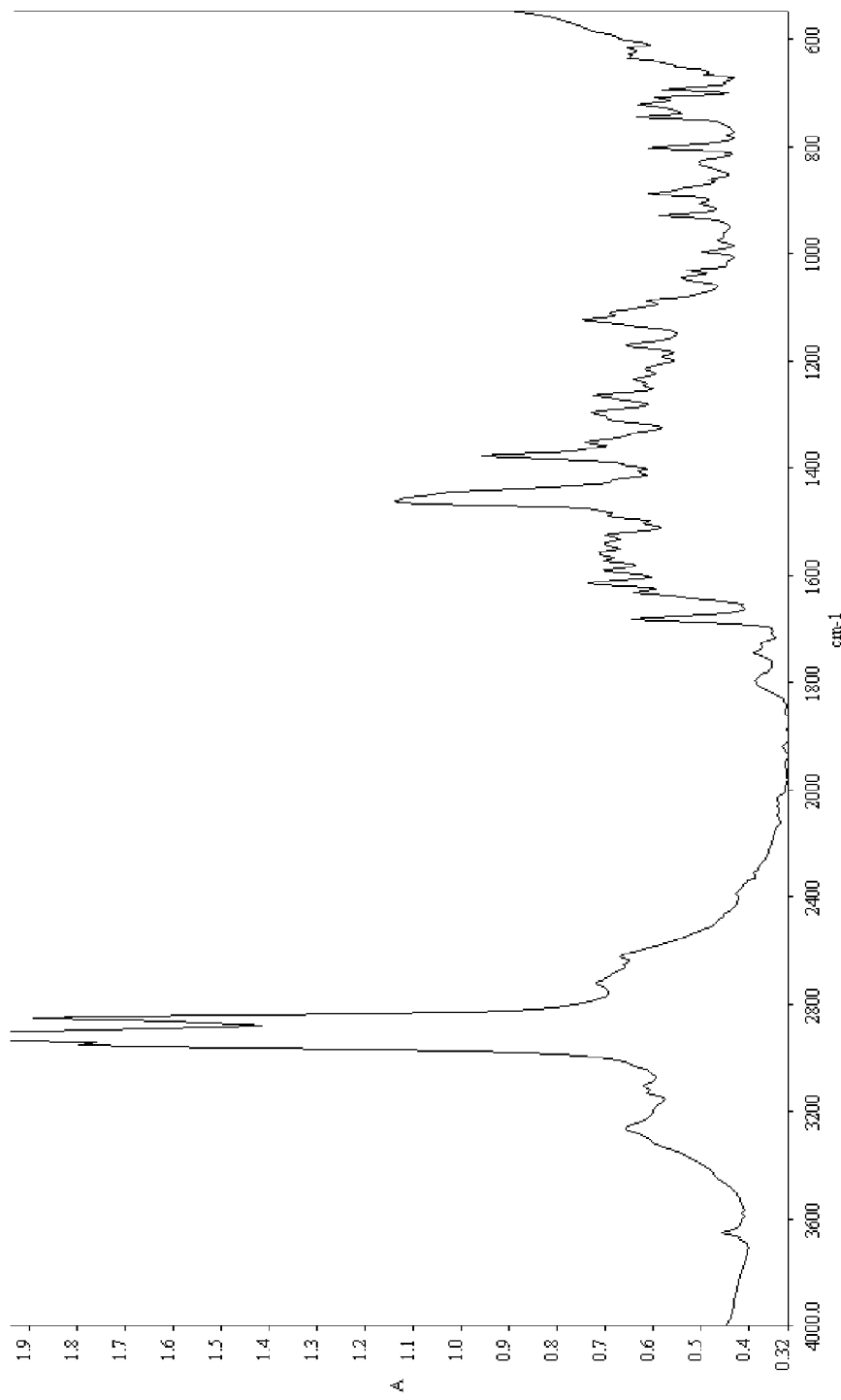
FIG. 3 shows an FT-IR spectrum of nilotinib HCl crystalline form T20, prepared according to example 1.
Figure 4:
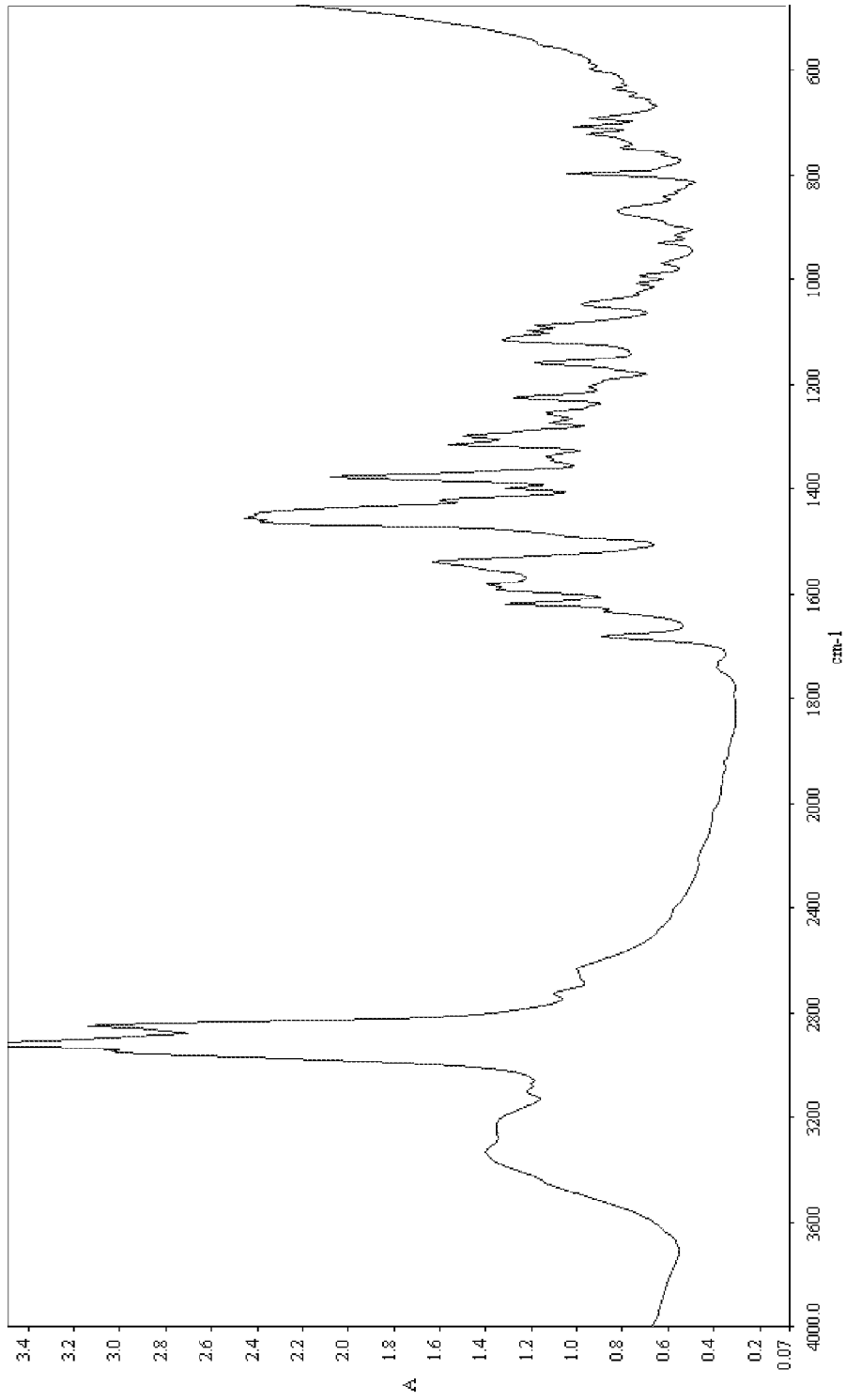
FIG. 4 shows an FT-IR spectrum of nilotinib HCl crystalline form T20, prepared according to example 3.

When form T20 is characterized by a FT-IR spectrum having peaks at 745, 803, 998, 1124, 1352, 1378, 1462 and 1525 cm$^{-1}$±2 cm$^{-1}$, it may be further characterized by a FT-IR spectrum substantially as depicted in FIG. 3. When form T20 is characterized by a FT-IR spectrum having peaks at 749, 798, 869, 969, 1378, 1399, 1455 and 1583 cm$^{-1}$±2 cm$^{-1}$, it may be further characterized by a FT-IR spectrum substantially as depicted in FIG. 4.

Figure 68:
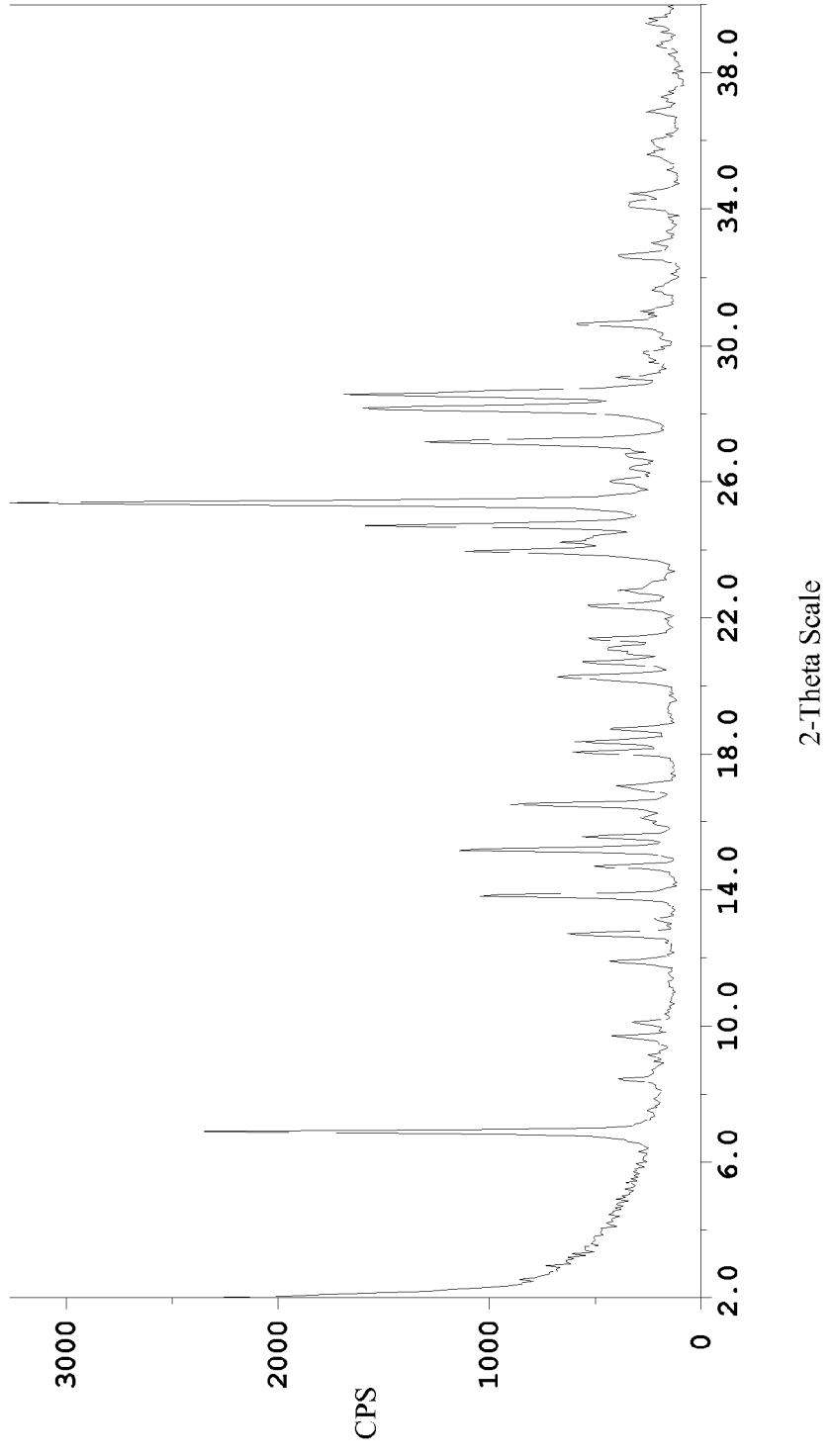
FIG. 68 shows an X-ray powder diffractogram of Nilotinib hydrochloride crystalline form T27.

The present invention encompasses a crystalline form of Nilotinib HCl, designated as form T27. Nilotinib HCl form T27 can be characterized by data selected from: an X-ray powder diffraction pattern having peaks at 6.8, 11.8, 12.6, 13.7 and 25.3 degrees two theta±0.2 degrees two theta; an X-ray powder diffraction pattern substantially as depicted in FIG. 68; and combinations thereof. The Nilotinib HCl form T27 may be further characterized by an X-ray powder diffraction pattern having additional peaks at 10.0, 15.0, 16.4, 20.2 and 24.6 degrees two theta±0.2 degrees two theta. Alternatively Nilotinib HCl form T27 can be characterized by an X-ray powder diffraction pattern with peaks at 6.8, 11.8, 12.6, 13.7 and 25.3 degrees two theta±0.2 degrees two theta; and also having one, two, three, four or more peaks selected from 8.3, 9.6, 10.0, 14.6, 15.0, 15.4, 16.4, 16.9, 18.0, 18.2, 18.6, 20.2, 20.6, 21.0, 21.3, 22.3, 22.7, 23.9, 24.6, 25.9 and 27.1 degrees two theta±0.2 degrees two theta.

Figure 69:
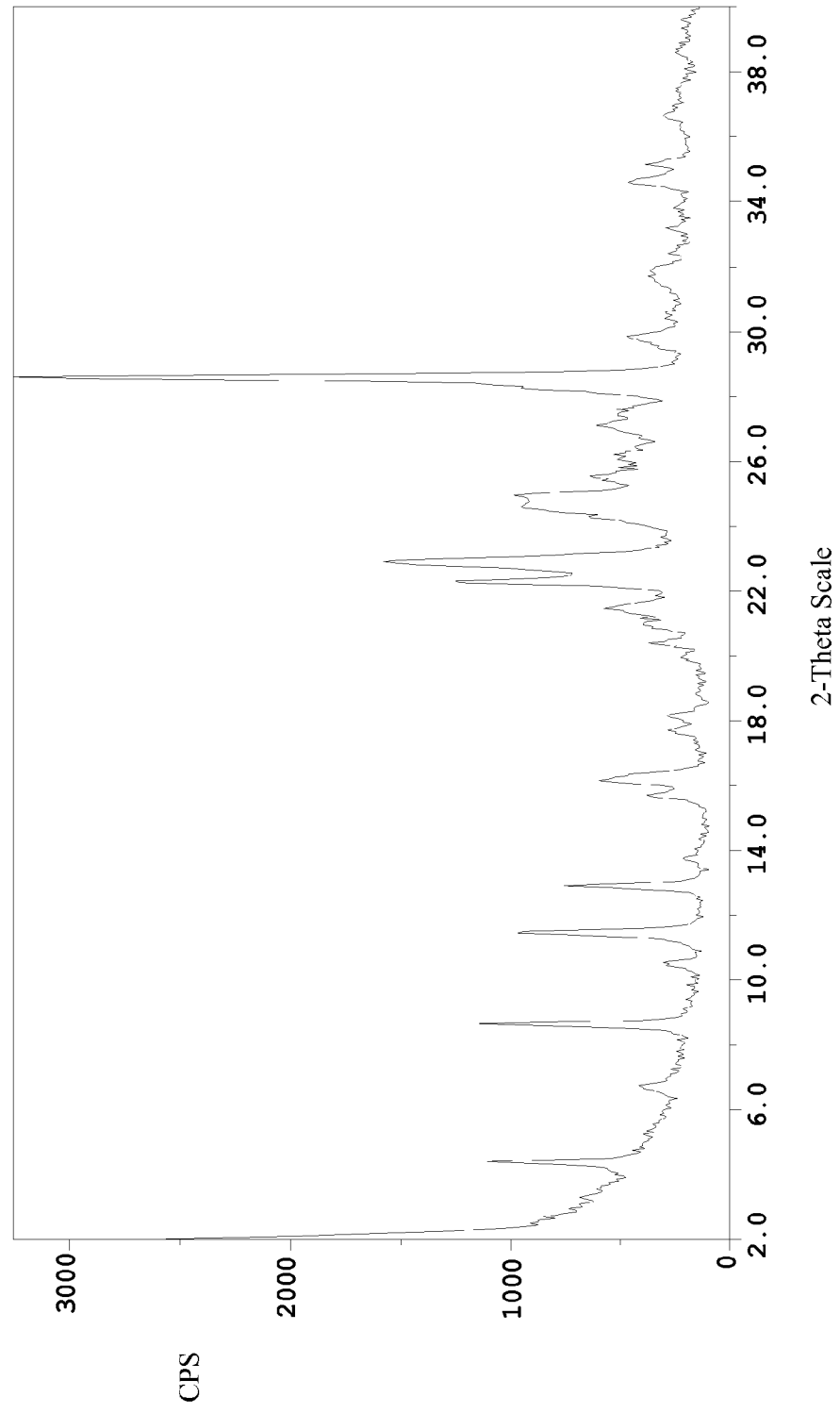
FIG. 69 shows an X-ray powder diffractogram of Nilotinib hydrochloride crystalline form T28.

The present invention encompasses a crystalline form of Nilotinib HCl, designated as form T28. Nilotinib HCl form T28 can be characterized by data selected from: an X-ray powder diffraction pattern having peaks at 4.2, 8.5, 11.3, 12.8 and 16.0 degrees two theta±0.2 degrees two theta; an X-ray powder diffraction pattern substantially as depicted in FIG. 69; and combinations thereof. The Nilotinib HCl form T28 may be further characterized by an X-ray powder diffraction pattern having additional peaks at 6.6, 10.4, 15.6, 22.1 and 24.5 degrees two theta±0.2 degrees two theta. Alternatively Nilotinib HCl form T28 can be characterized by an X-ray powder diffraction pattern with peaks at 4.2, 8.5, 11.3, 12.8 and 16.0 degrees two theta±0.2 degrees two theta; and also having one, two, three, four or more peaks selected from 6.6, 10.4, 15.6, 17.6, 18.0, 20.3, 20.8, 21.3, 22.1, 22.8, 24.5, 24.8, 25.4 and 27.0 degrees two theta±0.2 degrees two theta.

Figure 70:
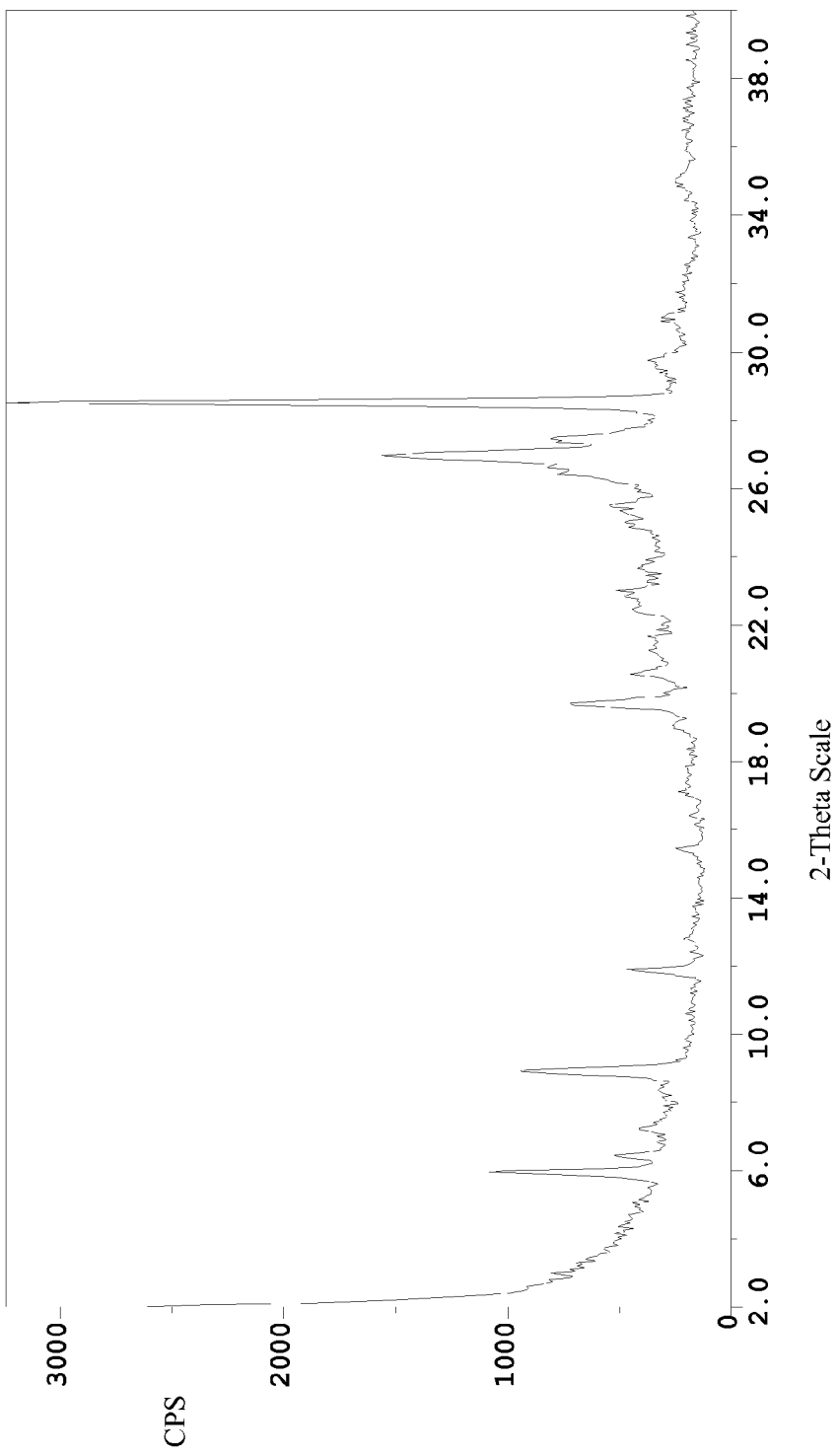
FIG. 70 shows an X-ray powder diffractogram of Nilotinib hydrochloride crystalline form T29.

The present invention encompasses a crystalline form of Nilotinib HCl, designated as form T29. Nilotinib HCl form T29 can be characterized by data selected from: an X-ray powder diffraction pattern having peaks at 6.0, 6.4, 8.9, 19.7 and 20.6 degrees two theta±0.2 degrees two theta; an X-ray powder diffraction pattern substantially as depicted in FIG. 70; and combinations thereof. The Nilotinib HCl form T29 may be further characterized by an X-ray powder diffraction pattern having additional peaks at 7.3, 11.9, 15.4, 27.0 and 27.4 degrees two theta±0.2 degrees two theta. Alternatively Nilotinib HCl form T29 can be characterized by an X-ray powder diffraction pattern with peaks at 6.0, 6.4, 8.9, 19.7 and 20.6 degrees two theta±0.2 degrees two theta; and also having one, two, three, four or more peaks selected from 7.3, 11.9, 15.4, 19.0, 27.0 and 27.4 degrees two theta±0.2 degrees two theta.

The invention also encompasses a process for preparing Nilotinib HCl form T20 comprising: slurrying a mixture of Nilotinib HCl form T18 and Nilotinib HCl form A in absolute ethanol to obtain a precipitate. The slurrying may be done at a temperature of about room temperature to about reflux temperature, for example at a temperature of about 78° C., for a time interval of about 15 minutes to about 21 hours. The obtained precipitate of Nilotinib HCl form T20 may be recovered, e.g., by filtering; and optionally drying the obtained precipitate. The drying may be done at a temperature from about 40° C. to about 60° C., or about 40° C. and about 50° C., for example, about 45° C.

The present invention provides a process for preparing Nilotinib HCl form T19 comprising: slurrying Nilotinib HCl form A in absolute ethanol to obtain a mixture. The slurrying may be followed by a heating step to a temperature from about 76° C. to about 80° C., or to about reflux temperature; and optionally maintaining the mixture at that temperature for a time interval of about 30 minutes to about 24 hours, for example, for about 1 hour. The obtained Nilotinib HCl form T19 may be further recovered from the mixture, for example, by filtering.

Figure 5:
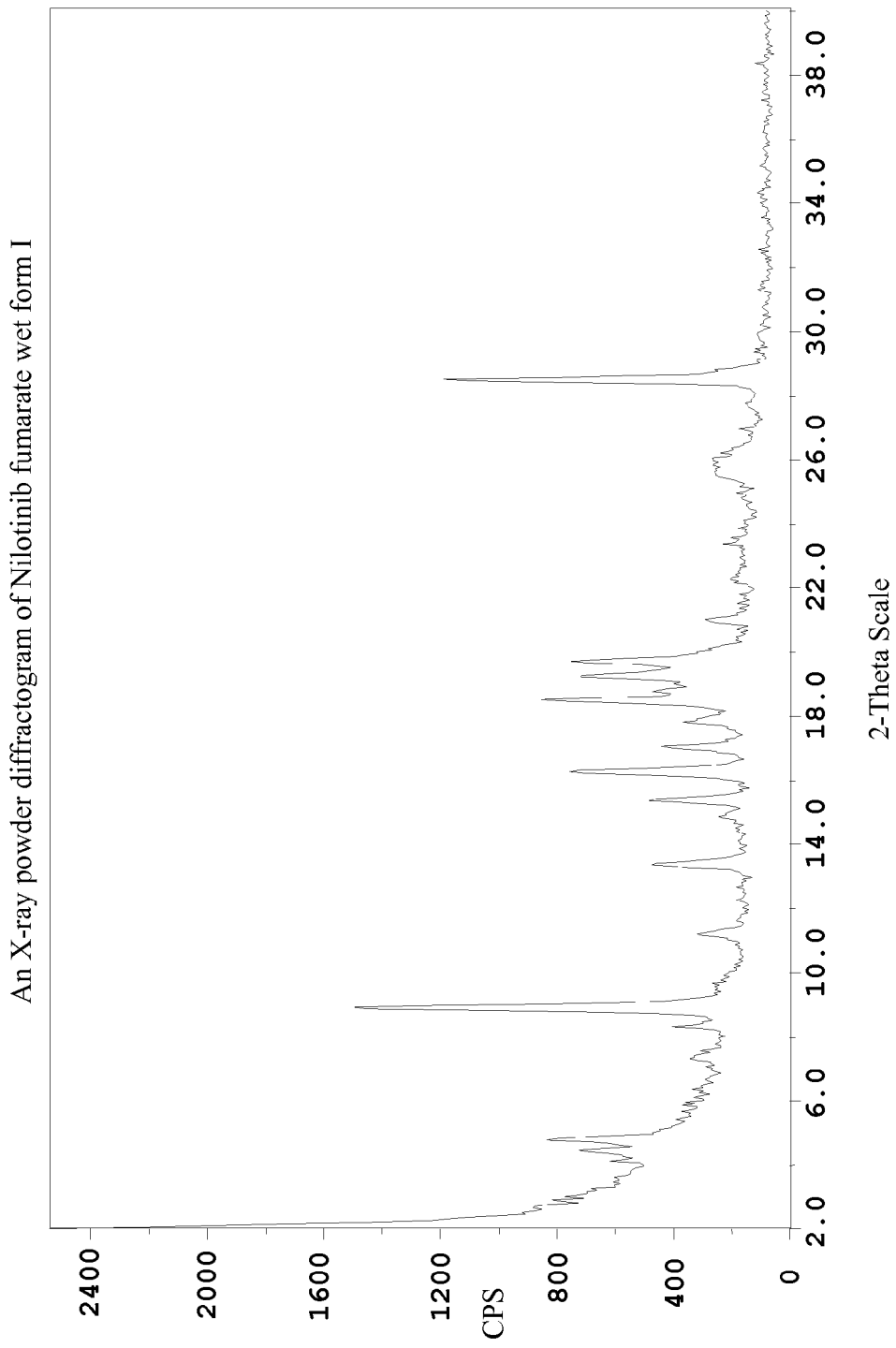
FIG. 5 shows an X-ray powder diffractogram of nilotinib fumarate wet crystalline form I.
Figure 6:
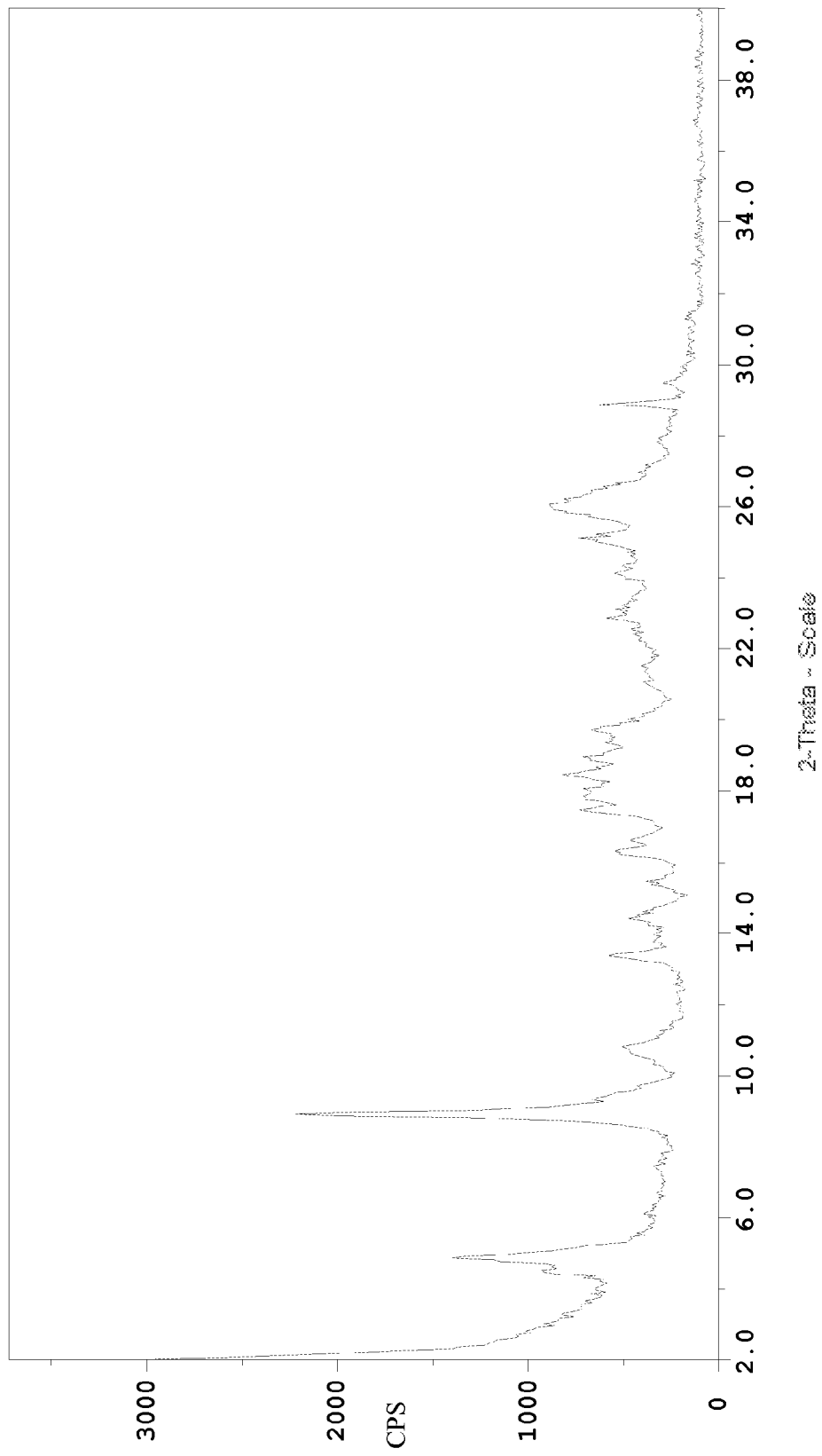
FIG. 6 shows an X-ray powder diffractogram of nilotinib fumarate dry crystalline form I.

The present invention encompasses a crystalline form of Nilotinib fumarate, designated as form I. Form I can be characterized by data selected from: an X-ray powder diffraction pattern having peaks at 4.8, 8.9, 16.2, 18.5 and 19.7 degrees two theta±0.2 degrees two theta; an X-ray powder diffraction pattern substantially as depicted in FIG. 5; an X-ray powder diffraction pattern substantially as depicted in FIG. 6; and a combination thereof. The Nilotinib Fumarate form I may be further characterized by additional X-ray powder diffraction peaks at 4.4, 13.3, 15.3, 17.0 and 19.2 degrees two theta±0.2 degrees two theta or by X-ray powder diffraction pattern having additional peaks at 4.4, 13.3, 14.3, 15.3 and 17.4 degrees two theta±0.2 degrees two theta.

The invention further encompasses a process for preparing Nilotinib fumarate form I comprising: dissolving Nilotinib base in trifluoroethanol (TFE) and fumaric acid. Typically, the fumaric acid is in a molar equivalent range of about 0.5 to about 1.1. Typically, the Nilotinib base is first dissolved in TFE; and then the fumaric acid is added to obtain a mixture.

The process for preparing Nilotinib fumarate form I may further comprise heating that is followed by cooling and optionally maintaining the mixture. The heating may be done to a temperature from about 30° C. to about 50° C., for example, to a temperature of about 40° C., and maintaining at that temperature for a time interval of about 30 minutes to about 3 hours, for example, for about 1 hour. The cooling may be done to a temperature such as about room temperature. The mixture may be maintained at about room temperature for a time interval such as from about 5 hours to about 3 days, for example, for about 2 days. The obtained Nilotinib fumarate may be further isolated, for example by evaporating the TFE; and drying. The drying may be done at a temperature from about 50° C. to about 70° C., for example, at about 60° C., for a time interval from about 1 day to about 3 days, for example, for about 2 days.

Figure 7:
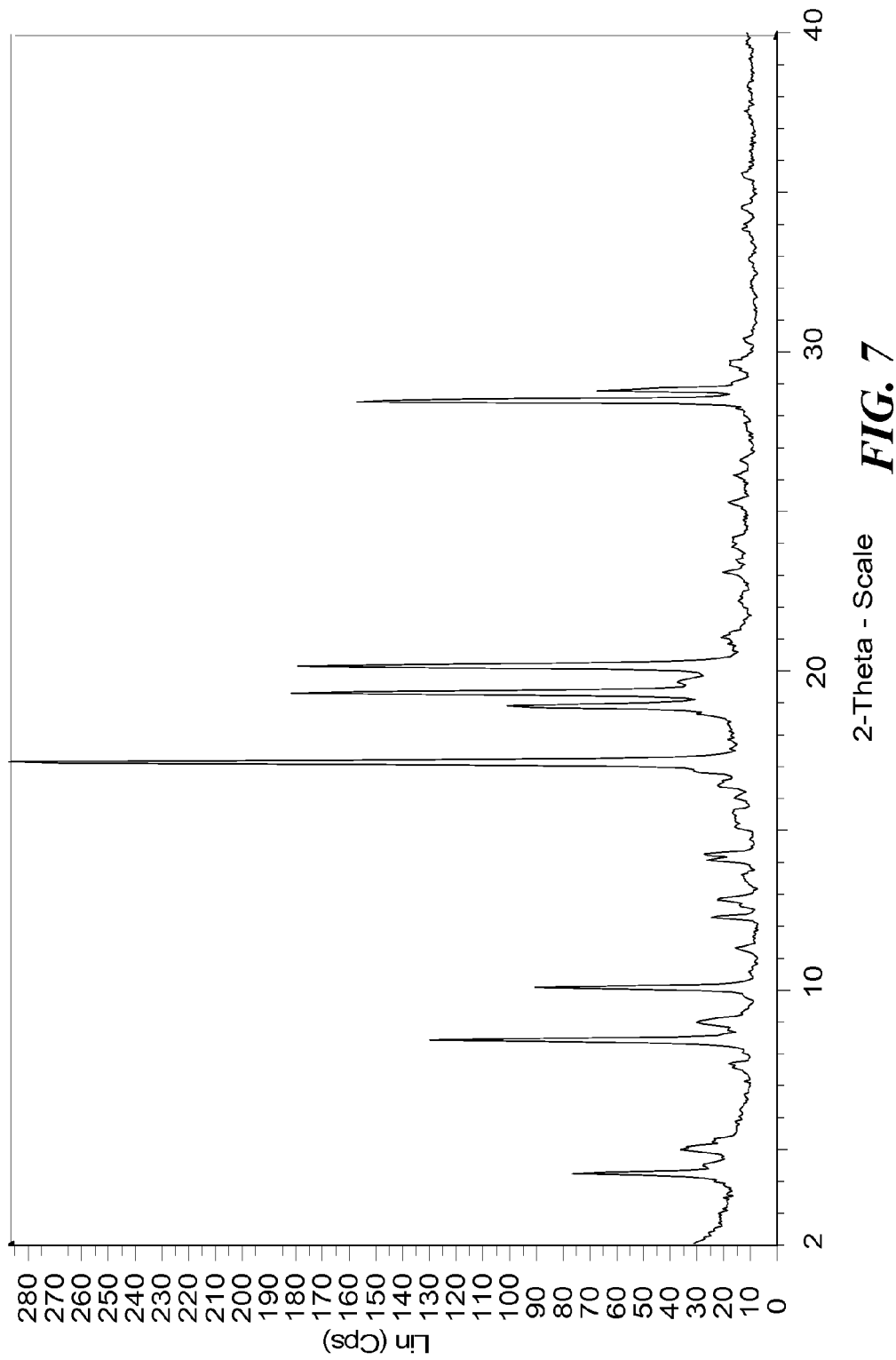
FIG. 7 shows an X-ray powder diffractogram of Nilotinib fumarate crystalline Form II.

The present invention encompasses a crystalline form of Nilotinib fumarate, designated as form II. Nilotinib fumarate form II can be characterized by data selected from: an X-ray powder diffraction pattern having peaks at 4.2, 8.4, 10.0, 17.1 and 19.3 degrees two theta±0.2 degrees two theta; an X-ray powder diffraction pattern substantially as depicted in FIG. 7; and combinations thereof. The Nilotinib fumarate form II may be further characterized by additional X-ray powder diffraction peaks at 5.0, 8.9, 18.9, 20.1 and 28.8 degrees two theta±0.2 degrees two theta.

Figure 8:
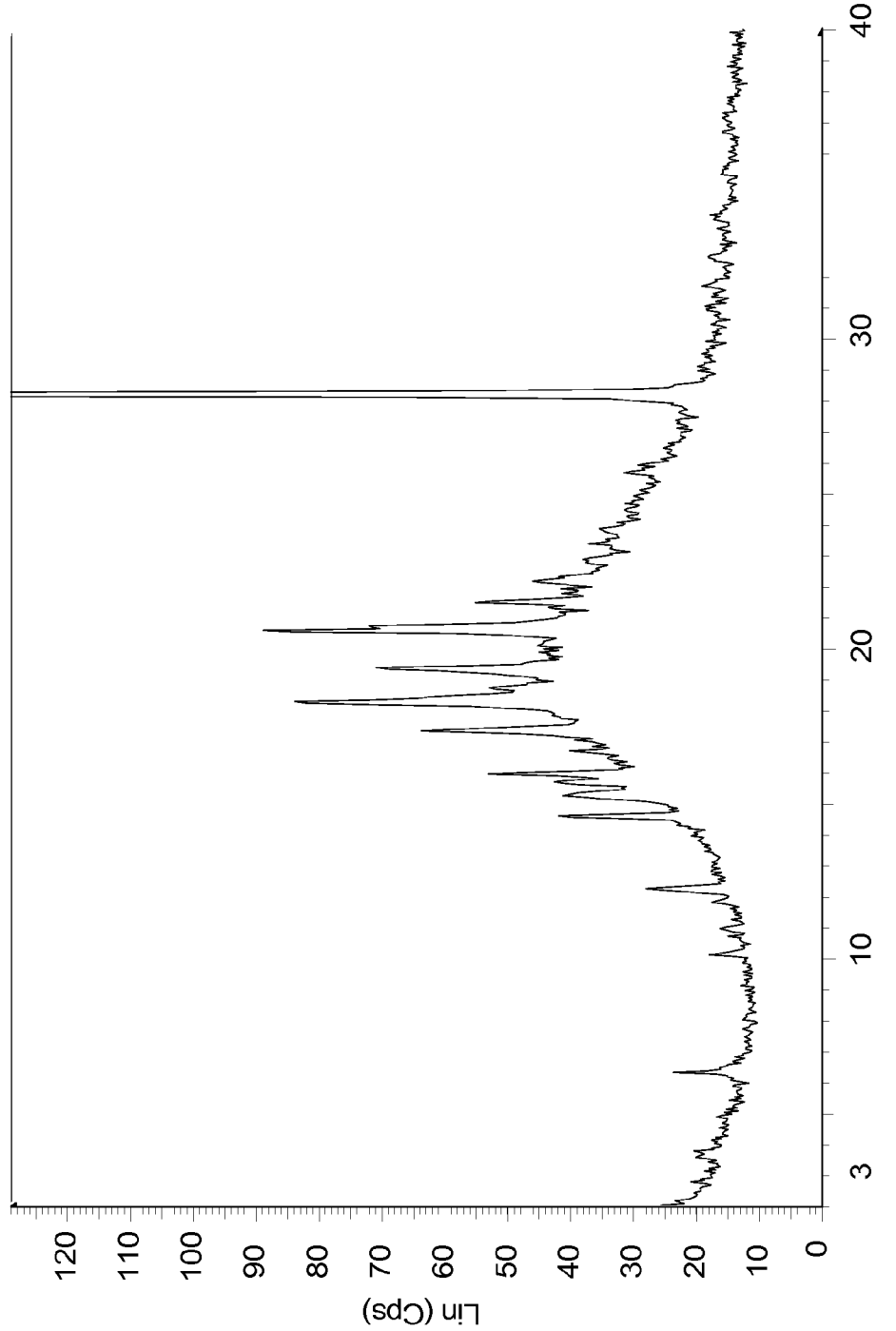
FIG. 8 shows an X-ray powder diffractogram of Nilotinib 2-chloro-mandelate crystalline Form I.

The present invention encompasses a crystalline form of Nilotinib 2-chloro-mandelate, designated as form I. Nilotinib 2-chloromandelate form I can be characterized by data selected from: an X-ray powder diffraction pattern having peaks at 14.8, 16.2, 17.6, 18.5 and 19.6 degrees two theta±0.2 degrees two theta; an X-ray powder diffraction pattern substantially as depicted in FIG. 8; and combinations thereof. The Nilotinib 2-chloromandelate form I may be further characterized by additional X-ray powder diffraction peaks at 6.5, 12.5, 15.5, 20.8 and 21.8 degrees two theta±0.2 degrees two theta.

Figure 9:
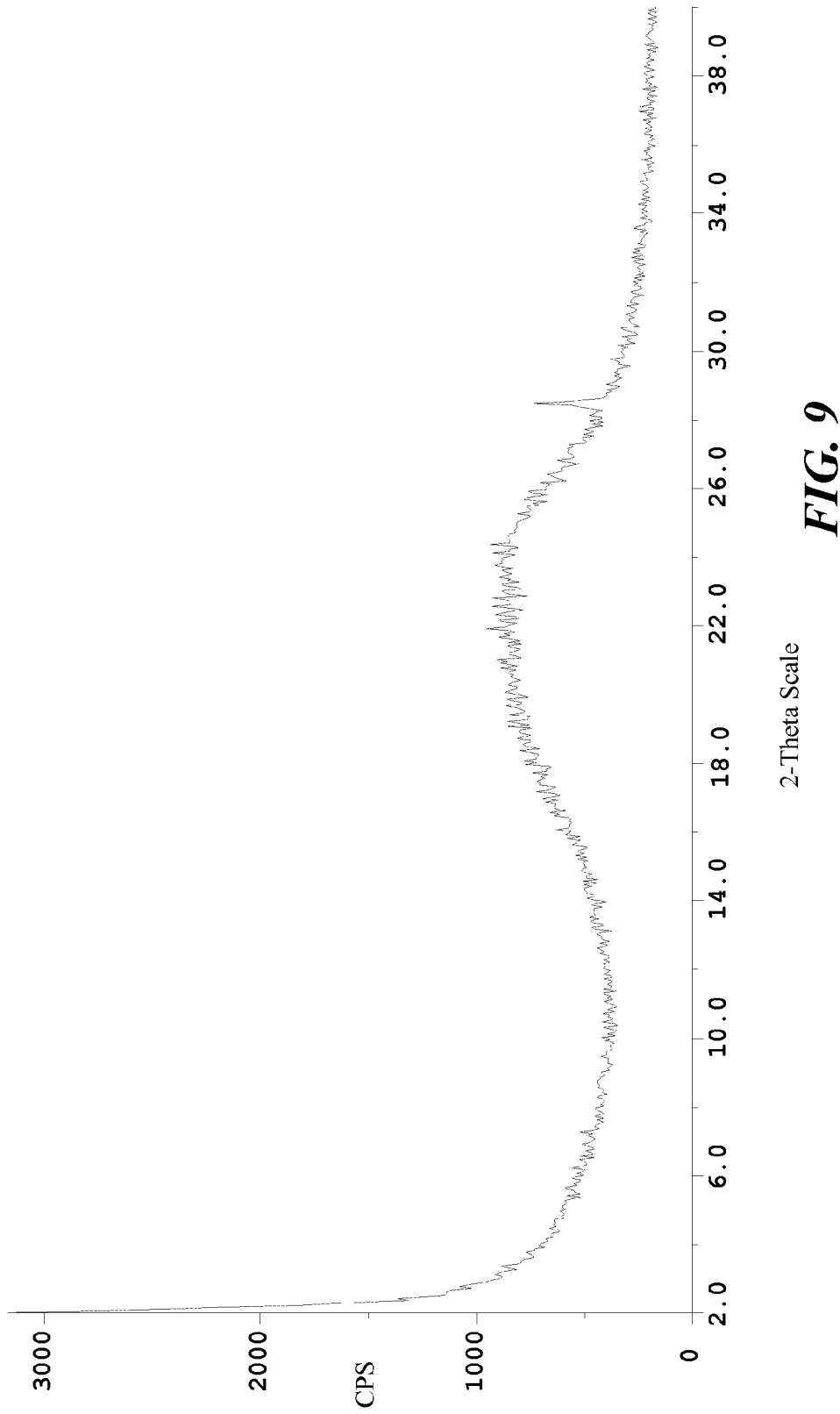
FIG. 9 shows an X-ray powder diffractogram of Nilotinib 2-chloro-mandelate amorphous form.

The present invention encompasses an amorphous form of Nilotinib 2-chloromandelate. The amorphous form of Nilotinib 2-chloromandelate can be characterized by an X-ray powder diffraction pattern substantially as depicted in FIG. 9.

Figure 10:
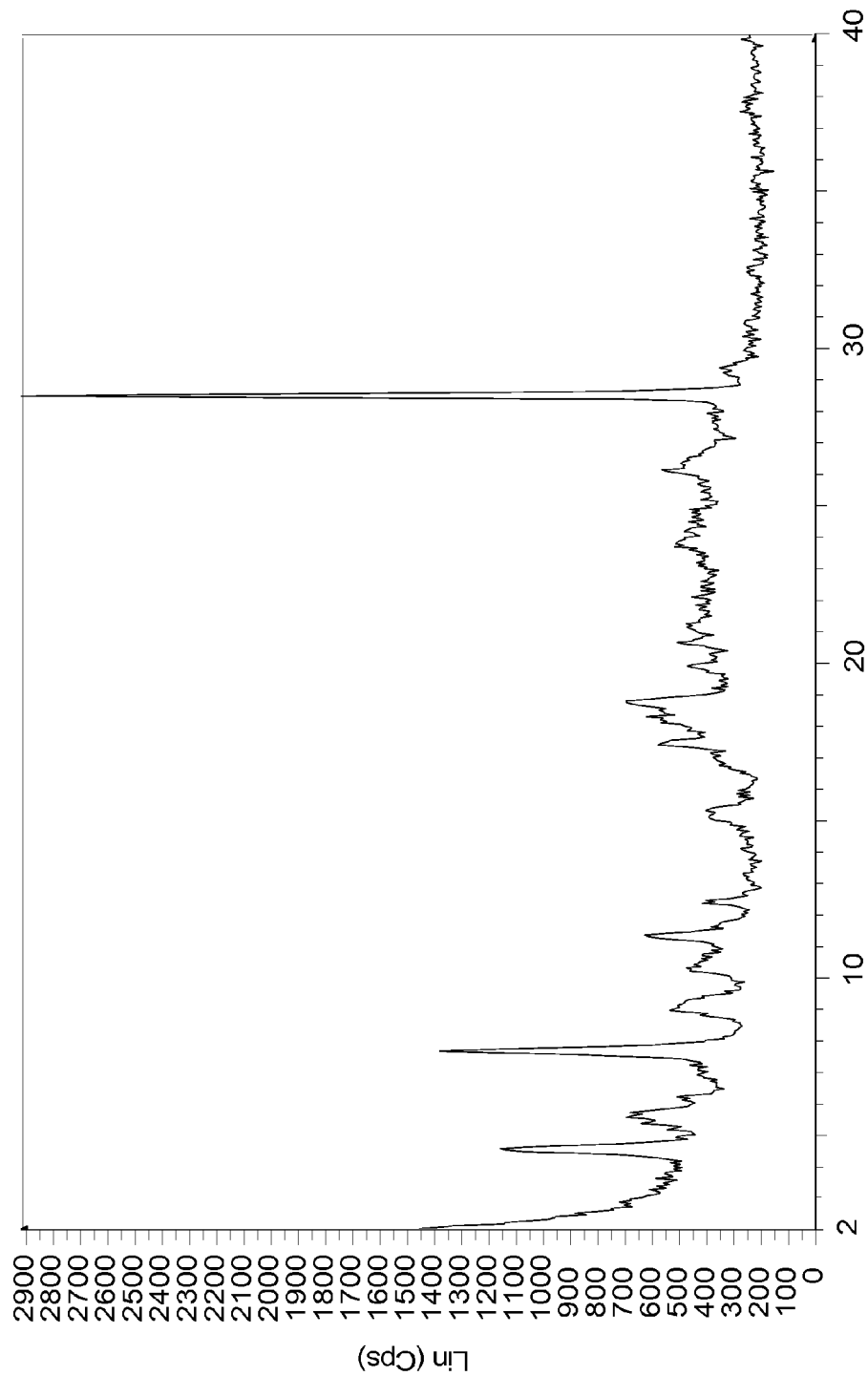
FIG. 10 shows an X-ray powder diffractogram of Nilotinib succinate crystalline form I.

The present invention encompasses a crystalline form of Nilotinib succinate, designated as form I. Nilotinib succinate Form I can be characterized by data selected from: an X-ray powder diffraction pattern having peaks at 4.5, 7.6, 11.3, 17.4 and 18.7 degrees two theta±0.2 degrees two theta; an X-ray powder diffraction pattern having peaks at 4.4, 7.6, 11.3, 17.3 and 18.7 degrees two theta±0.2 degrees two theta; an X-ray powder diffraction pattern substantially as depicted in FIG. 10; and combinations thereof. The Nilotinib succinate form I may be further characterized by additional X-ray powder diffraction peaks at 5.5, 8.9, 10.3, 12.3 and 26.1 degrees two theta±0.2 degrees two theta; additional X-ray powder diffraction peaks at 5.2, 8.8, 10.5, 12.3 and 26.1 degrees two theta±0.2 degrees two theta; or a combination of this data.

Figure 11:
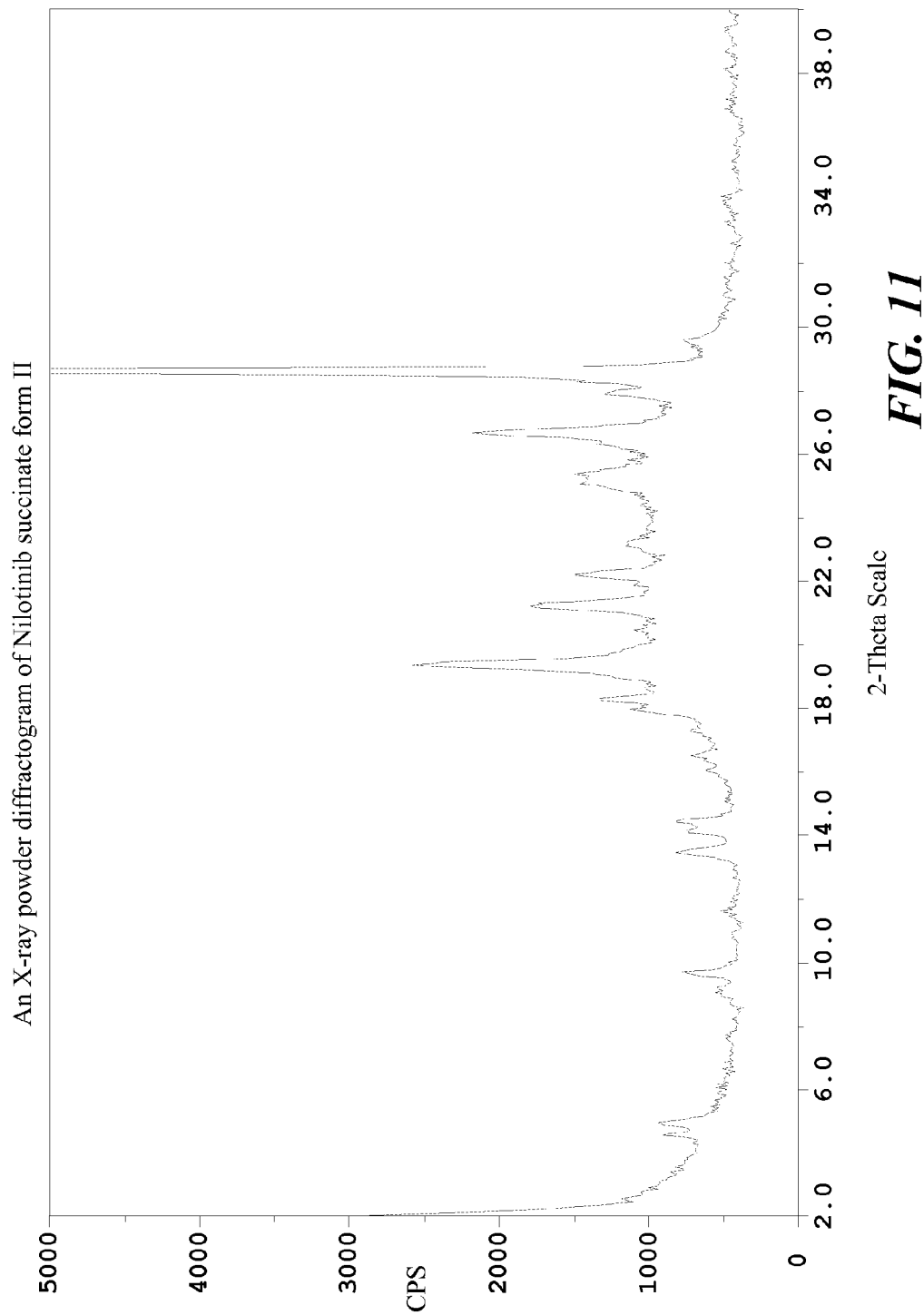
FIG. 11 shows an X-ray powder diffractogram of Nilotinib succinate crystalline form II.

The present invention encompasses a crystalline form of Nilotinib succinate, designated as form II. Nilotinib succinate form II can be characterized by data selected from: an X-ray powder diffraction pattern having peaks at 4.8, 9.5, 13.3, 19.2 and 21.0 degrees two theta±0.2 degrees two theta; an X-ray powder diffraction pattern substantially as depicted in FIG. 11; and combinations thereof. The Nilotinib succinate form II may be further characterized by additional X-ray powder diffraction peaks at 4.4, 14.2, 18.1, 22.0 and 26.5 degrees two theta±0.2 degrees two theta.

Figure 12:
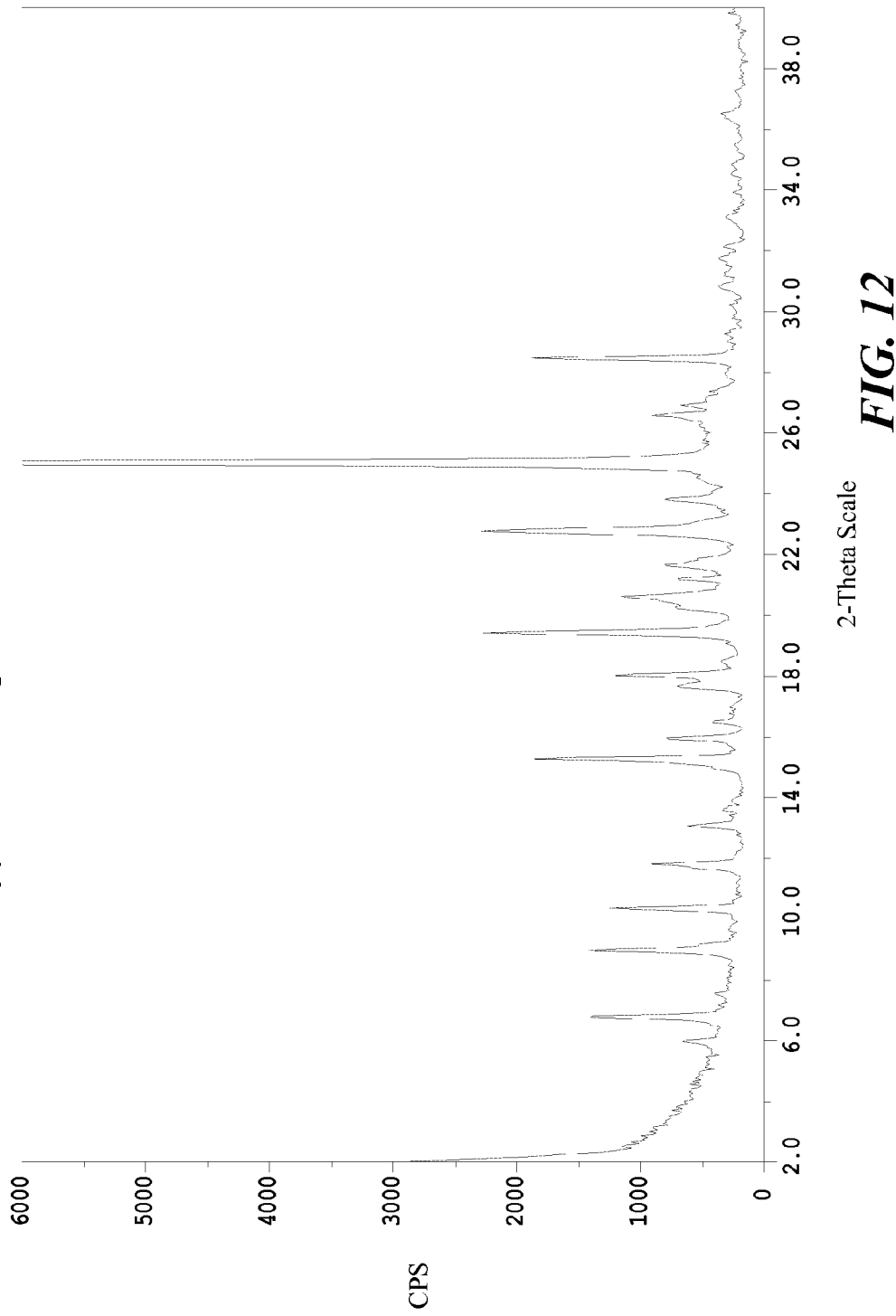
FIG. 12 shows an X-ray powder diffractogram of Nilotinib succinate crystalline form III.

The present invention encompasses a crystalline form of Nilotinib succinate, designated as form III. Nilotinib succinate form III can be characterized by data selected from: an X-ray powder diffraction pattern having peaks at 6.8, 9.0, 10.4, 15.3 and 19.4 degrees two theta±0.2 degrees two theta; an X-ray powder diffraction pattern substantially as depicted in FIG. 12; and combinations thereof. The Nilotinib succinate form III may be further characterized by additional X-ray powder diffraction peaks at 11.8, 18.0, 20.6, 22.8 and 25.0 degrees two theta±0.2 degrees two theta.

Figure 13:
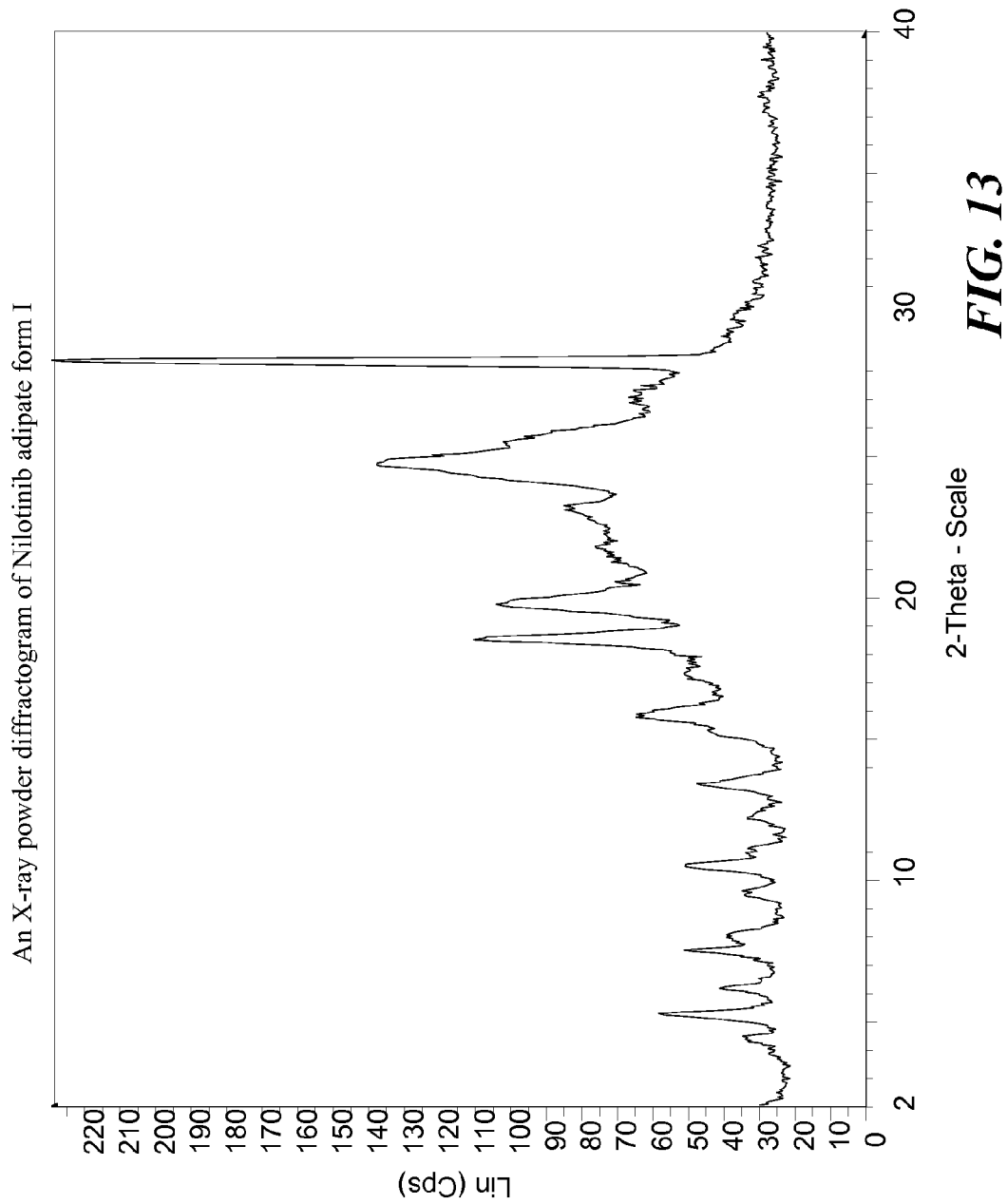
FIG. 13 shows an X-ray powder diffractogram of Nilotinib adipate crystalline form I.

The present invention encompasses a crystalline form of Nilotinib adipate, designated as form I. Nilotinib adipate form I can be characterized by data selected from: an X-ray powder diffraction pattern having peaks at 5.3, 7.6, 10.5, 18.6 and 19.8 degrees two theta±0.2 degrees two theta; an X-ray powder diffraction pattern substantially as depicted in FIG. 13; and combinations thereof. The Nilotinib adipate form I may be further characterized by additional X-ray powder diffraction peaks at 4.4, 6.2, 13.4, 15.9 and 24.8 degrees two theta±0.2 degrees two theta.

Figure 14:
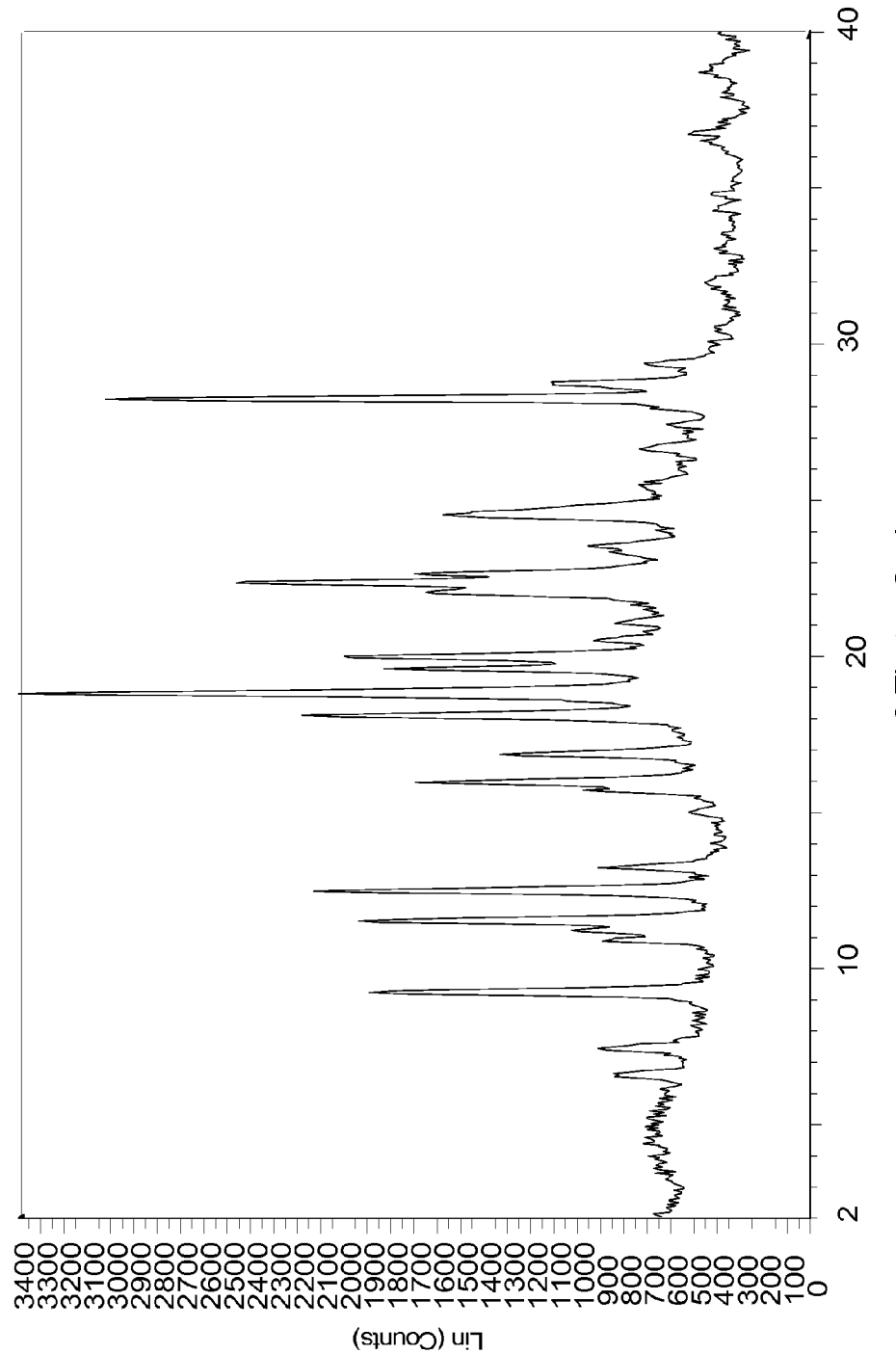
FIG. 14 shows an X-ray powder diffractogram of Nilotinib L-tartrate crystalline form I.

The present invention encompasses a crystalline form of Nilotinib L-tartrate, designated as form I. Nilotinib L-tartrate form I can be characterized by data selected from: an X-ray powder diffraction pattern having peaks at 9.4, 11.7, 12.7, 18.2 and 19.0 degrees two theta±0.2 degrees two theta; an X-ray powder diffraction pattern substantially as depicted in FIG. 14; and combinations thereof. The Nilotinib L-tartrate form I may be further characterized by additional X-ray powder diffraction peaks at 7.6, 16.1, 17.1, 20.1 and 22.6 degrees two theta±0.2 degrees two theta. Typically, the Nilotinib L-tartrate form I can be of Nilotinib monotartrate salt.

Figure 15:
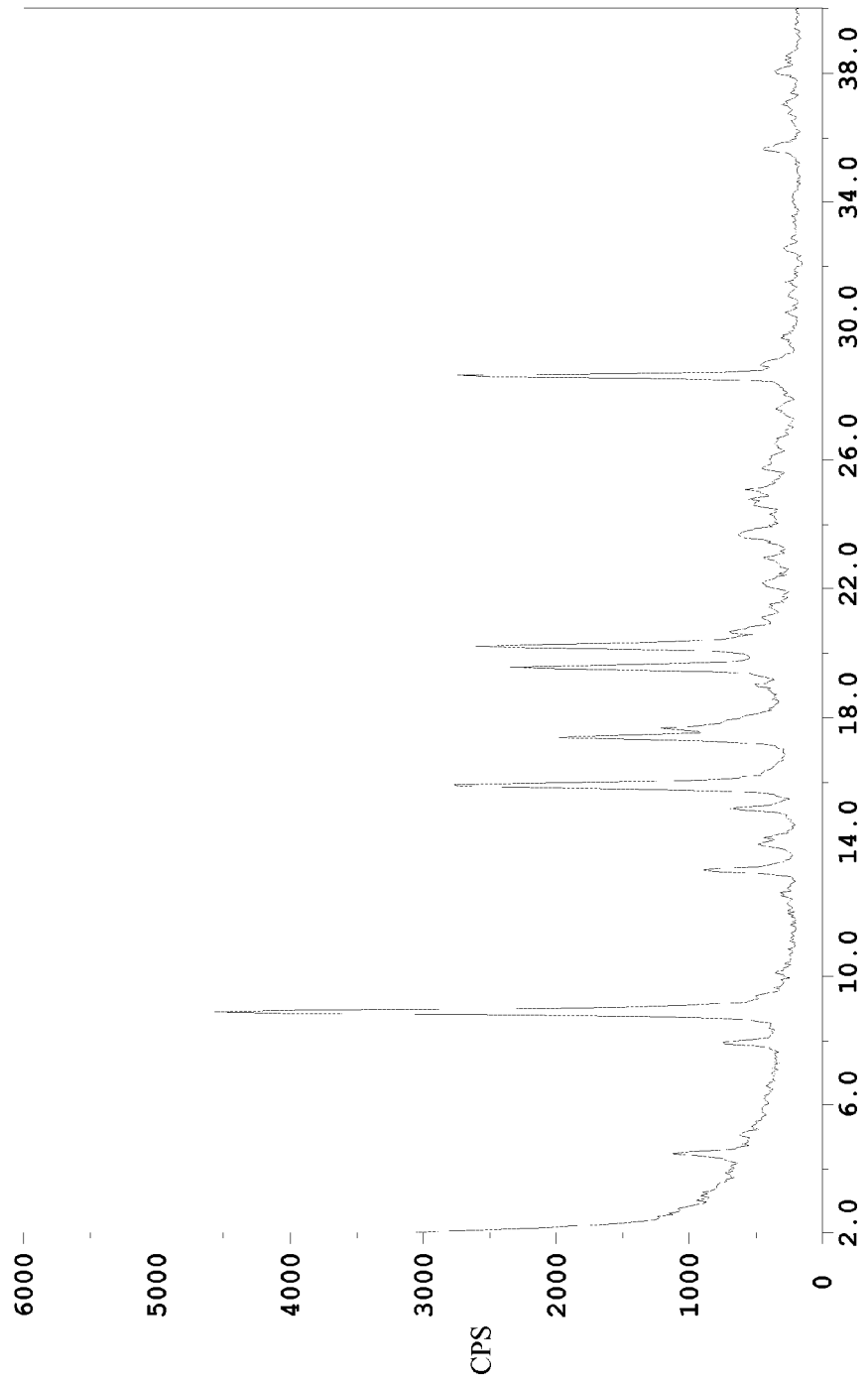
FIG. 15 shows an X-ray powder diffractogram of Nilotinib L-tartrate crystalline form II.

The present invention encompasses a crystalline form of Nilotinib L-tartrate, designated as form II. Nilotinib L-tartrate form II can be characterized by data selected from: an X-ray powder diffraction pattern having peaks at 8.7, 15.7, 17.2, 19.4 and 20.0 degrees two theta±0.2 degrees two theta; an X-ray powder diffraction pattern substantially as depicted in FIG. 15; and combinations thereof. The Nilotinib L-tartrate form II may be further characterized by additional X-ray powder diffraction peaks at 4.3, 7.7, 13.0, 13.9 and 15.0 degrees two theta±0.2 degrees two theta.

Figure 16:
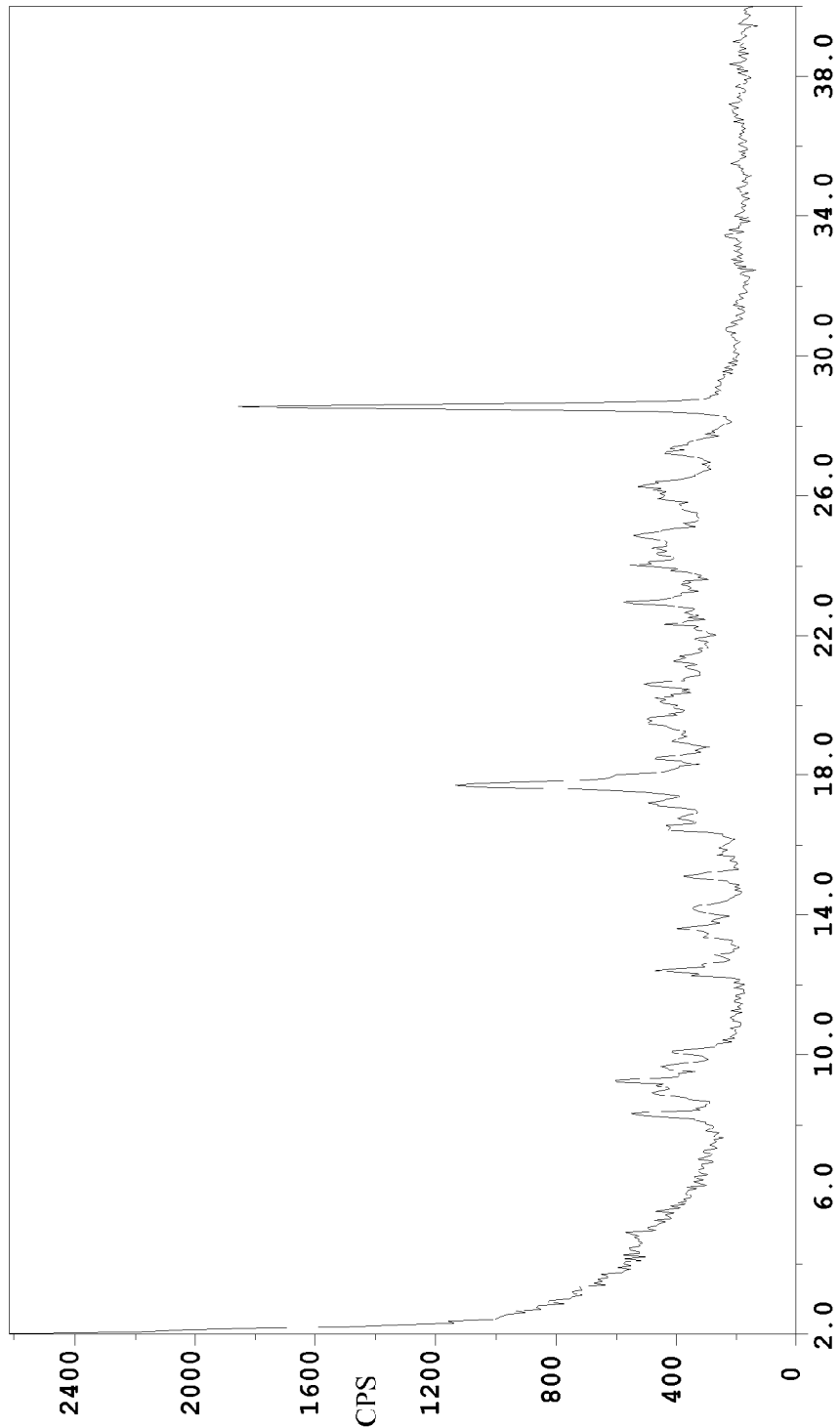
FIG. 16 shows an X-ray powder diffractogram of Nilotinib L-tartrate crystalline form III.

The present invention encompasses a crystalline form of Nilotinib L-tartrate, designated as form III. Nilotinib L-tartrate form III can be characterized by data selected from: an X-ray powder diffraction pattern having peaks at 8.2, 9.1, 12.3, 15.0 and 17.6 degrees two theta±0.2 degrees two theta; an X-ray powder diffraction pattern substantially as depicted in FIG. 16; and combinations thereof. The Nilotinib L-tartrate form III may be further characterized by additional X-ray powder diffraction peaks at 9.9, 13.5, 18.4, 20.5 and 22.9 degrees two theta±0.2 degrees two theta.

Figure 60:
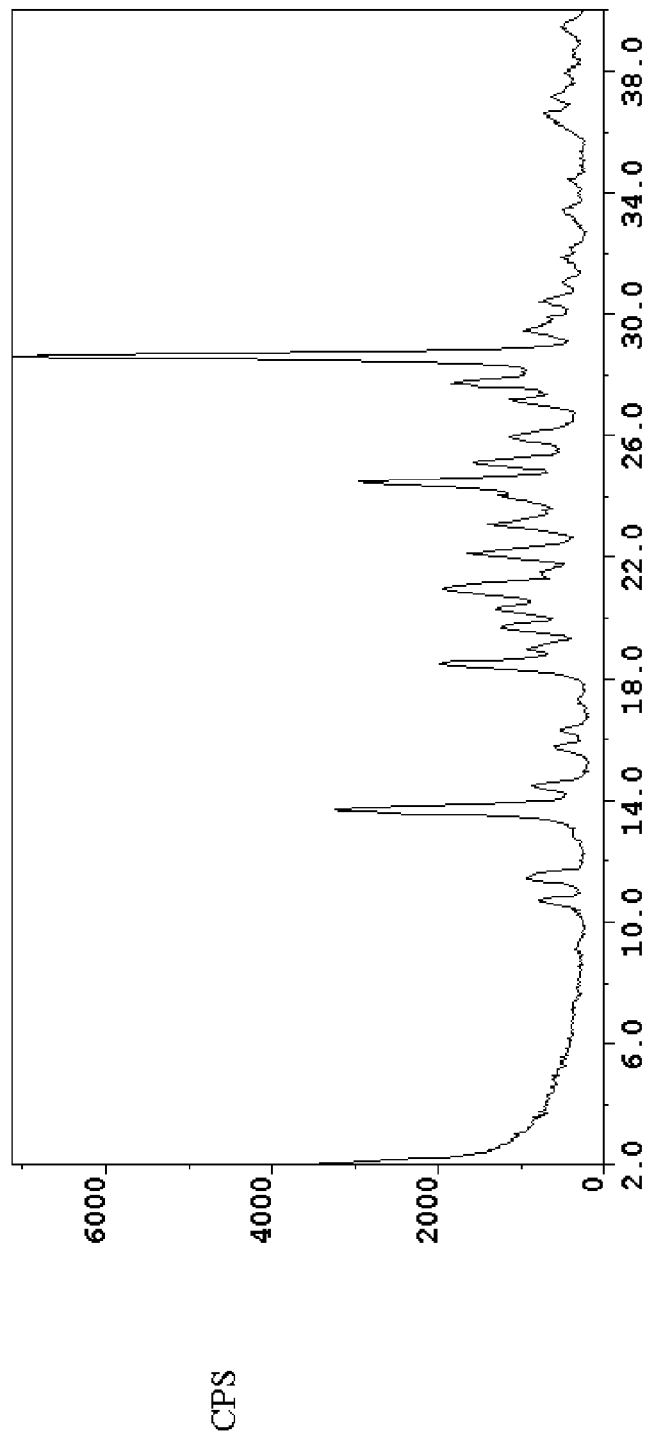
FIG. 60 shows an X-ray powder diffractogram of Nilotinib L-tartrate crystalline form IV.

In another embodiment, the present invention encompasses a crystalline form of Nilotinib L-tartrate, designated as form IV. Nilotinib L-tartrate form IV can be characterized by data selected from: an X-ray powder diffraction pattern having peaks at 13.6 18.3, 19.5, 21.9 and 24.3 degrees two theta±0.2 degrees two theta; an X-ray powder diffraction pattern substantially as depicted in FIG. 60; a solid state $^{13}$C NMR spectrum having signals at 118.7, 136.2 and 172.7±0.2 ppm; a solid-state $^{13}$C NMR spectrum having chemical shifts differences between the signal exhibiting the lowest chemical shift in the chemical shift range of 100 to 180 ppm and another in the chemical shift range of 100 to 180 ppm of 12.0, 29.5 and 66.0±0.1 ppm; a solid state $^{13}$C NMR spectrum as depicted in any one of FIGS. 71-72; and combinations thereof. Typically, the signal exhibiting the lowest chemical shift in the chemical shift range of 100 to 180 ppm is typically at about 106.7±1 ppm. The Nilotinib L-tartrate form IV may be further characterized by an X-ray powder diffraction pattern having one, two, three, four or five peaks selected from 10.6, 11.3, 20.8, 22.9 and 25.0 degrees two theta±0.2 degrees two theta.

Typically, Nilotinib L-tartrate Form IV can be anhydrous.
Typically, Nilotinib L-tartrate Form IV can be mono-L-tartrate salt.

As discussed above, Nilotinib L-tartrate Form IV has advantageous properties. In particular, the crystalline Nilotinib L-tartrate Form IV of the present invention demonstrates thermal polymorphic stability, which means it does not convert to other forms when heated up to 200° C.

Figure 61:
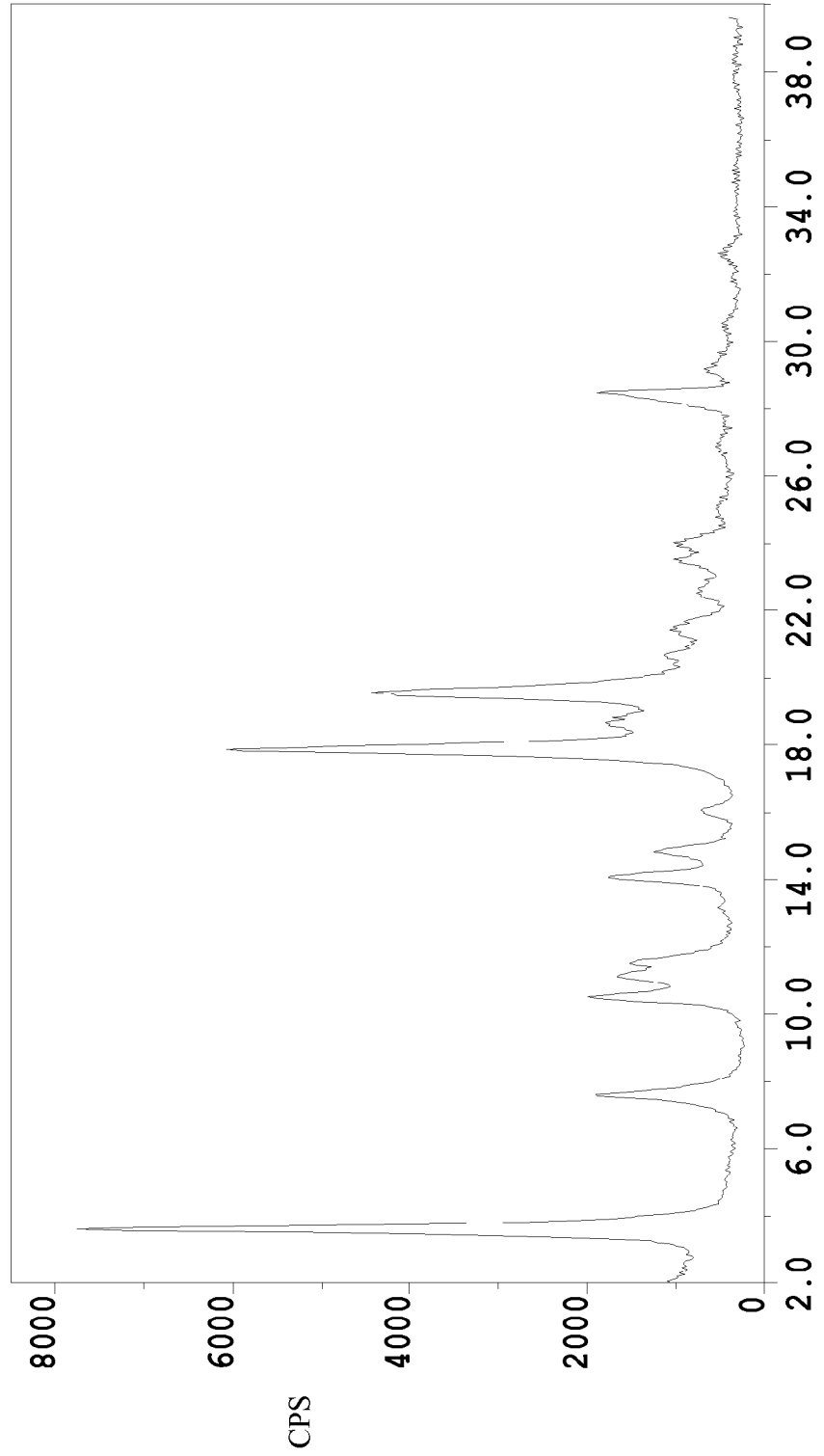
FIG. 61 shows an X-ray powder diffractogram of Nilotinib L-tartrate crystalline form V.

In another embodiment, the present invention encompasses a crystalline form of Nilotinib L-tartrate, designated as form V. Nilotinib L-tartrate form V can be characterized by data selected from: an X-ray powder diffraction pattern having peaks at 3.6, 7.6, 14.1, 17.8 and 19.5 degrees two theta±0.2 degrees two theta; an X-ray powder diffraction pattern substantially as depicted in FIG. 61; and combinations thereof. The Nilotinib L-tartrate form V may be further characterized by additional X-ray powder diffraction peaks at 10.5, 11.1, 14.8 and 16.0 degrees two theta±0.2 degrees two theta.

Figure 62:
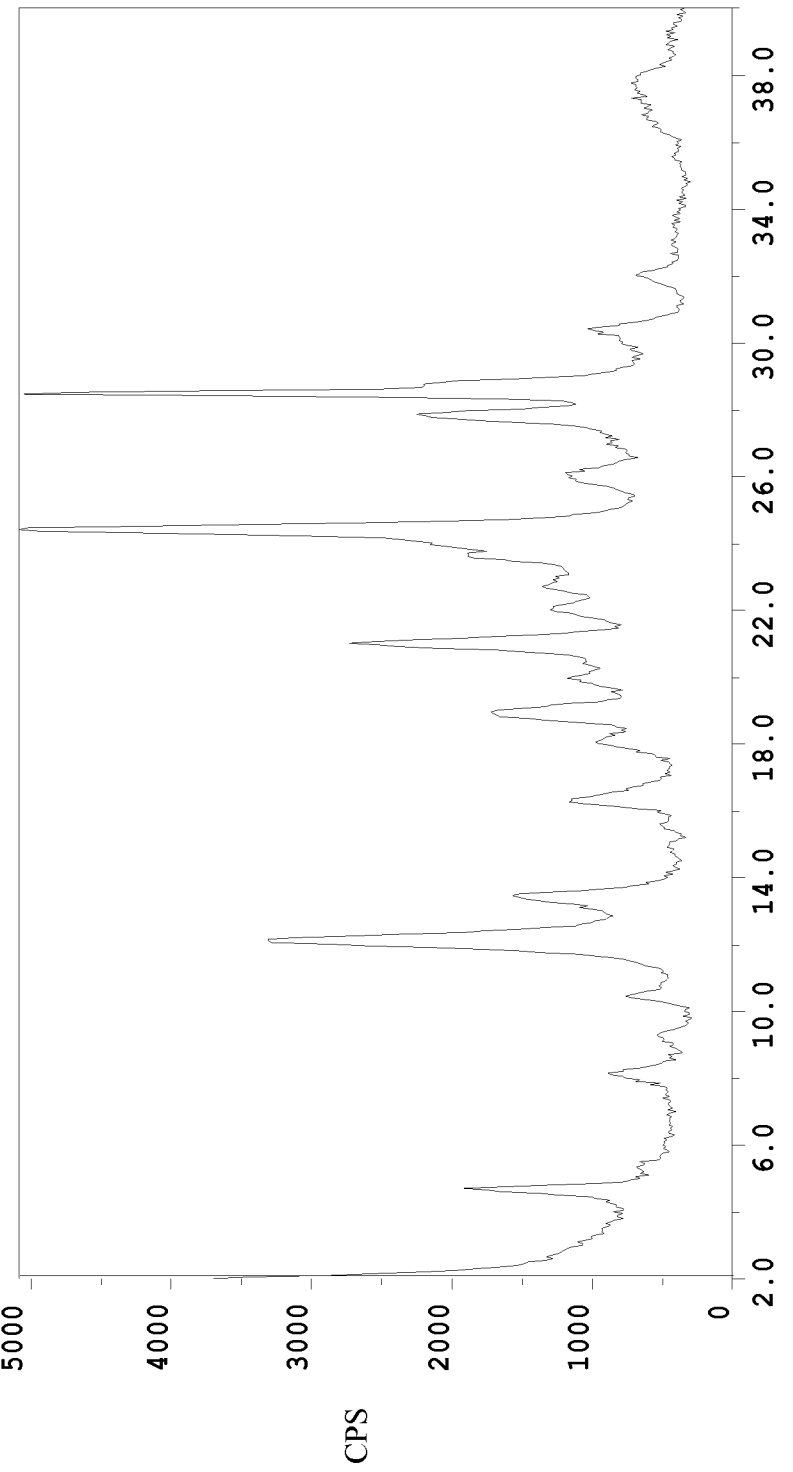
FIG. 62 shows an X-ray powder diffractogram of Nilotinib L-tartrate crystalline form VI.

In yet another embodiment, the present invention encompasses a crystalline form of Nilotinib L-tartrate, designated as form VI. Nilotinib L-tartrate form VI can be characterized by data selected from: an X-ray powder diffraction pattern having peaks at 4.7, 12.1, 16.3, 21.0 and 24.4 degrees two theta±0.2 degrees two theta; an X-ray powder diffraction pattern substantially as depicted in FIG. 62; and combinations thereof. The Nilotinib L-tartrate form VI may be further characterized by additional X-ray powder diffraction peaks at 8.1, 10.5, 13.5, 18.9 and 27.9 degrees two theta±0.2 degrees two theta.

Figure 17:
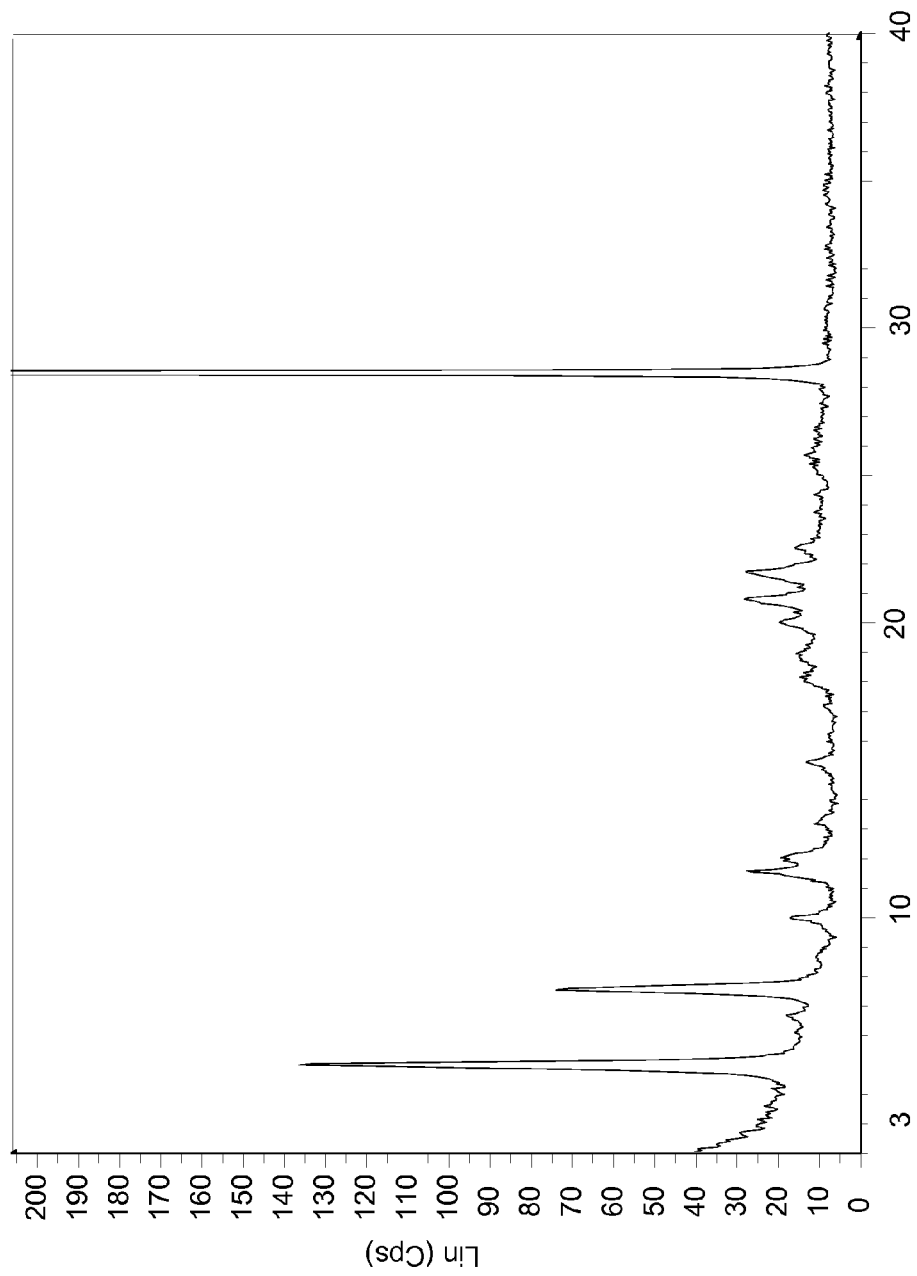
FIG. 17 shows an X-ray powder diffractogram of Nilotinib glutarate crystalline form I.
Figure 18:
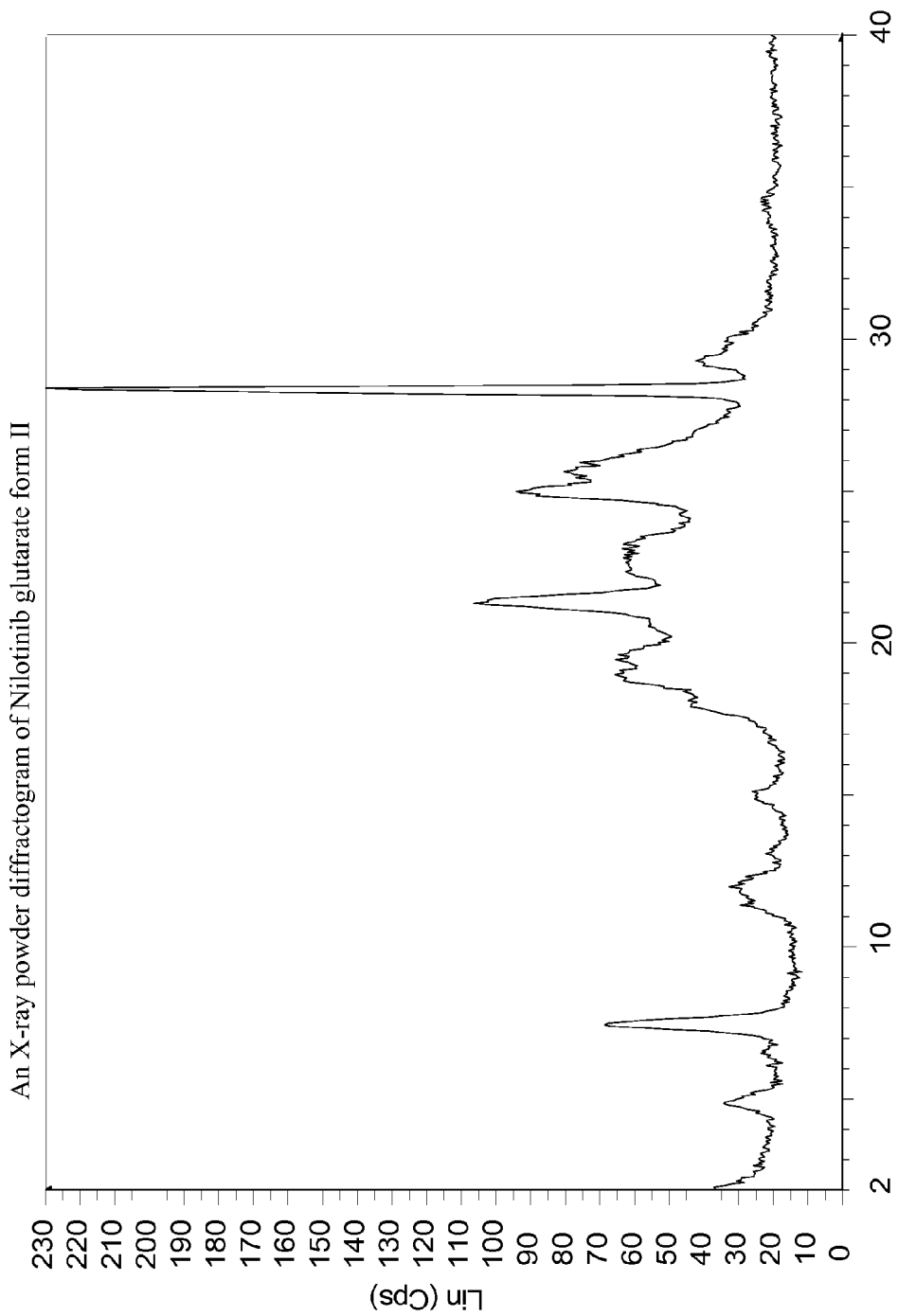
FIG. 18 shows an X-ray powder diffractogram of Nilotinib glutarate crystalline form II.

The present invention encompasses a crystalline form of Nilotinib glutarate, designated as form I. Nilotinib glutarate form I can be characterized by data selected from: an X-ray powder diffraction pattern having peaks at 4.9, 7.5, 11.5, 20.8 and 21.7 degrees two theta±0.2 degrees two theta; an X-ray powder diffraction pattern substantially as depicted in FIG. 17; and combinations thereof. The Nilotinib glutarate form I may be further characterized by additional X-ray powder diffraction peaks at 9.9, 11.9, 15.2, 20.0 and 22.5 degrees two theta±0.2 degrees two theta.

The present invention encompasses a crystalline form of Nilotinib glutarate, designated as form II. Nilotinib glutarate form II can be characterized by data selected from: an X-ray powder diffraction pattern having peaks at 4.9, 7.5, 21.4, 25.0 and 25.6 degrees two theta±0.2 degrees two theta; an X-ray powder diffraction pattern substantially as depicted in FIG.

18; and combinations thereof. The Nilotinib glutarate form II may be further characterized by additional broad X-ray powder diffraction peaks having maxima at 12.0, 15.0, 19.0, 23.2 and 29.4 degrees two theta±0.2 degrees two theta and a peak at 22.5 degrees two theta±0.2 degrees two theta.

Figure 19:
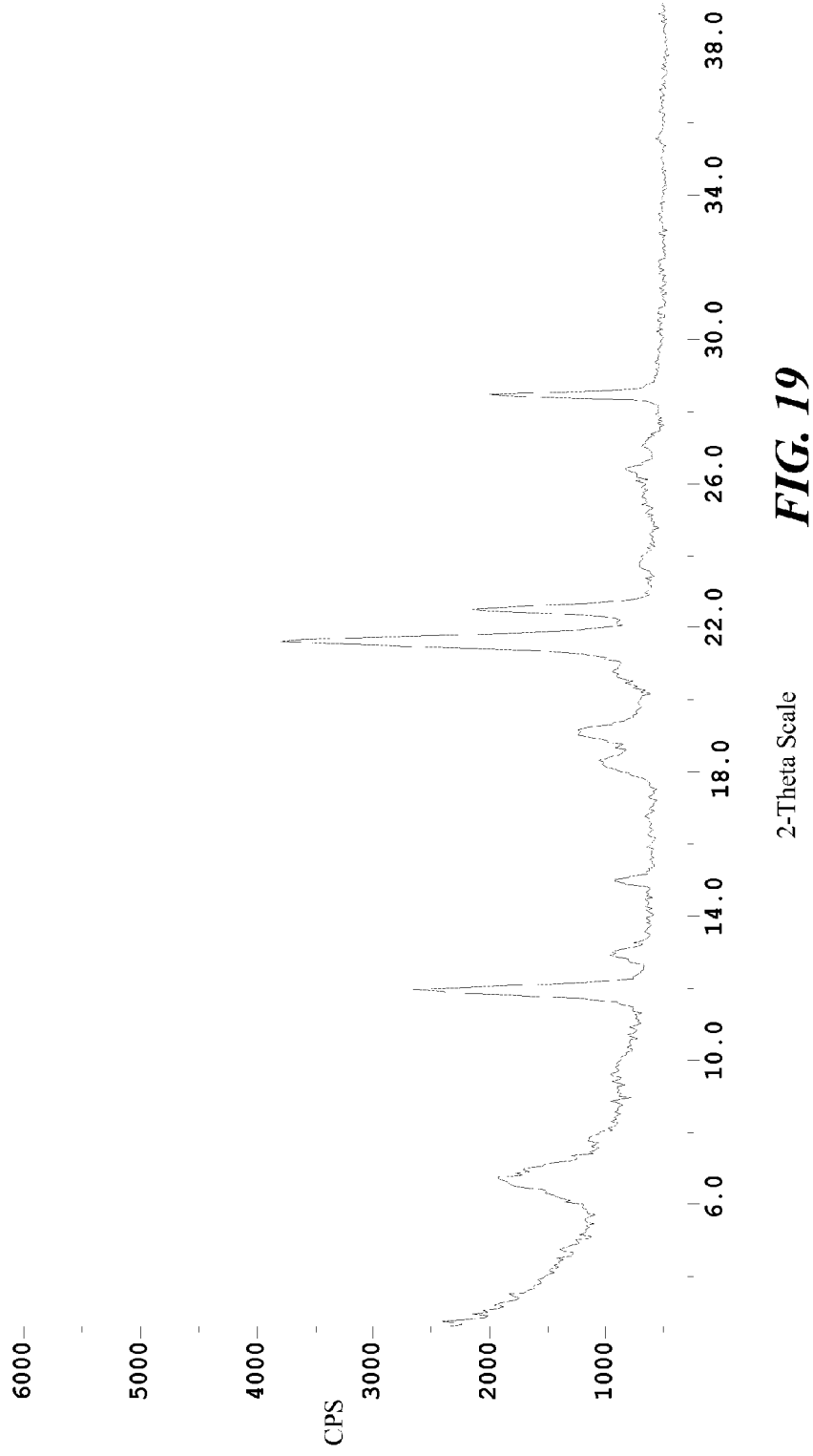
FIG. 19 shows an X-ray powder diffractogram of Nilotinib glutarate crystalline form III.

The present invention encompasses a crystalline form of Nilotinib glutarate, designated as form III. Nilotinib glutarate form III can be characterized by data selected from: an X-ray powder diffraction pattern having peaks at 12.0, 19.0, 21.6, and 22.5 degrees two theta±0.2 degrees two theta and a broad peak having a maximum at 6.7 degrees two theta±0.2 degrees two theta; an X-ray powder diffraction pattern substantially as depicted in FIG. 19; and combinations thereof. The Nilotinib glutarate form III may be further characterized by additional broad X-ray powder diffraction peaks having maxima at 12.9, 15.0 and 18.3 degrees two theta±0.2 degrees two theta.

Figure 20:
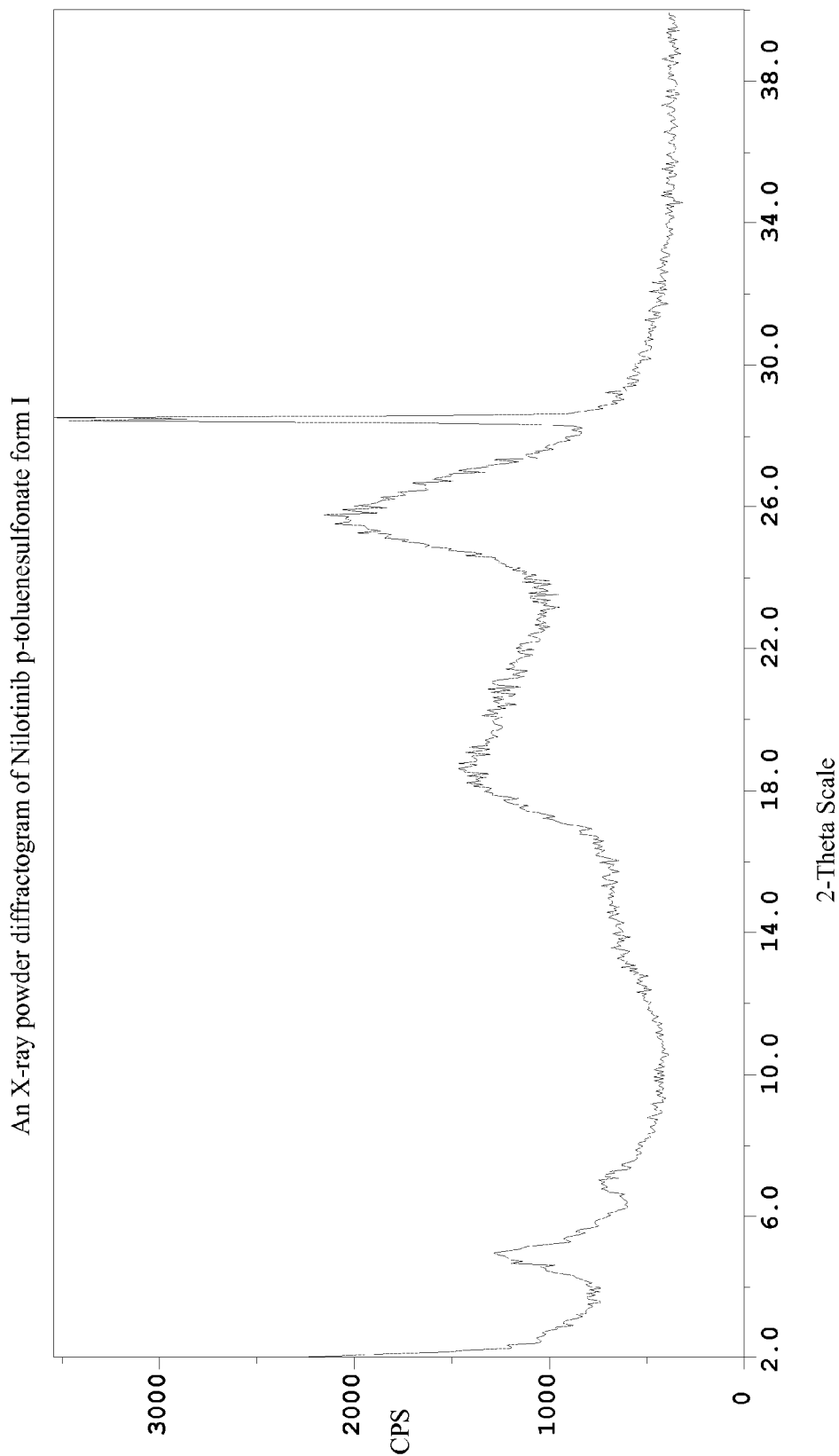
FIG. 20 shows an X-ray powder diffractogram of Nilotinib p-toluene-sulfonate crystalline form I.

The present invention encompasses a crystalline form of Nilotinib p-toluenesulfonate, designated as form I. Nilotinib p-toluenesulfonate form I can be characterized by data selected from: an X-ray powder diffraction pattern with broad peaks having maxima at 4.9, 7.0, 18.5 and 25.7 degrees two theta±0.2 degrees two theta; an X-ray powder diffraction pattern substantially as depicted in FIG. 20; and combinations thereof.

Figure 21:
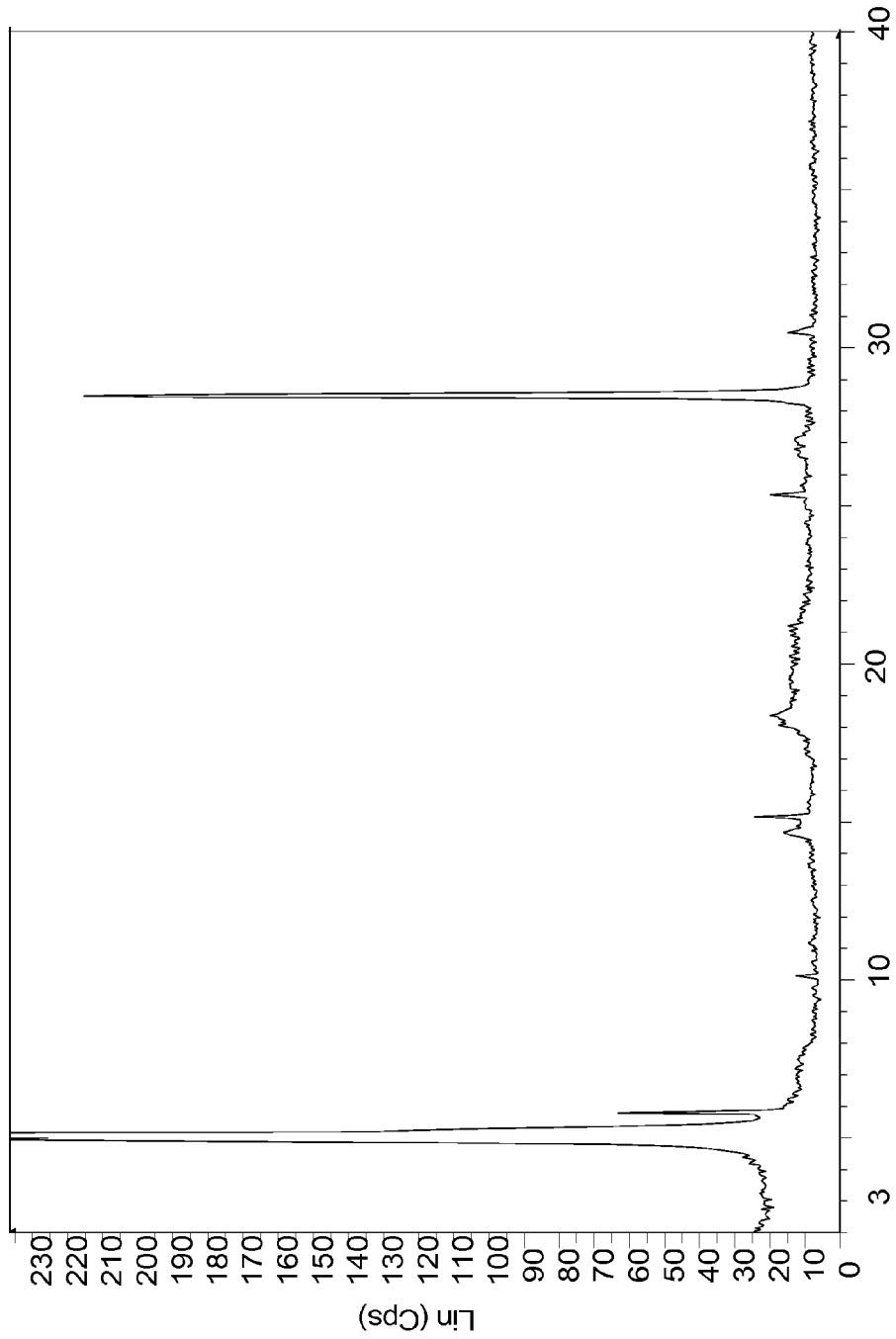
FIG. 21 shows an X-ray powder diffractogram of Nilotinib p-toluene-sulfonate crystalline form II.

The present invention encompasses a crystalline form of Nilotinib p-toluenesulfonate, designated as form II. Nilotinib p-toluenesulfonate Form II can be characterized by data selected from: an X-ray powder diffraction pattern having peaks at 5.0, 14.6, 18.3 and 27.0 degrees two theta±0.2 degrees two theta; an X-ray powder diffraction pattern substantially as depicted in FIG. 21; and combinations thereof.

Figure 22:
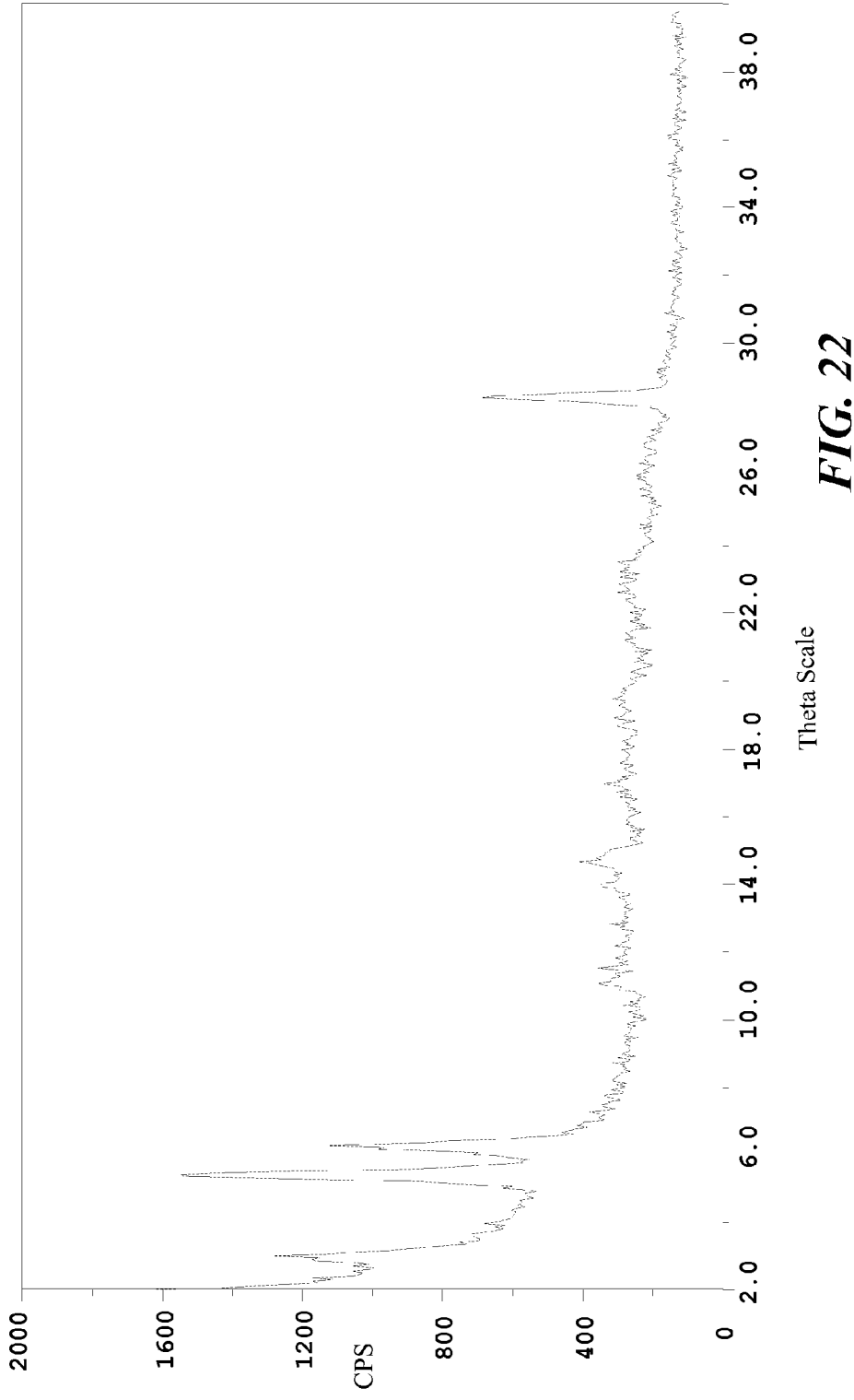
FIG. 22 shows an X-ray powder diffractogram of Nilotinib camphor-sulfonate crystalline form I.

The present invention encompasses a crystalline form of Nilotinib camphorsulfonate, designated as form I. Nilotinib camphorsulfonate form I can be characterized by data selected from: an X-ray powder diffraction pattern having peaks at 3.0, 5.4 and 6.2 degrees two theta±0.2 degrees two theta; an X-ray powder diffraction pattern substantially as depicted in FIG. 22; and combinations thereof.

Figure 23:
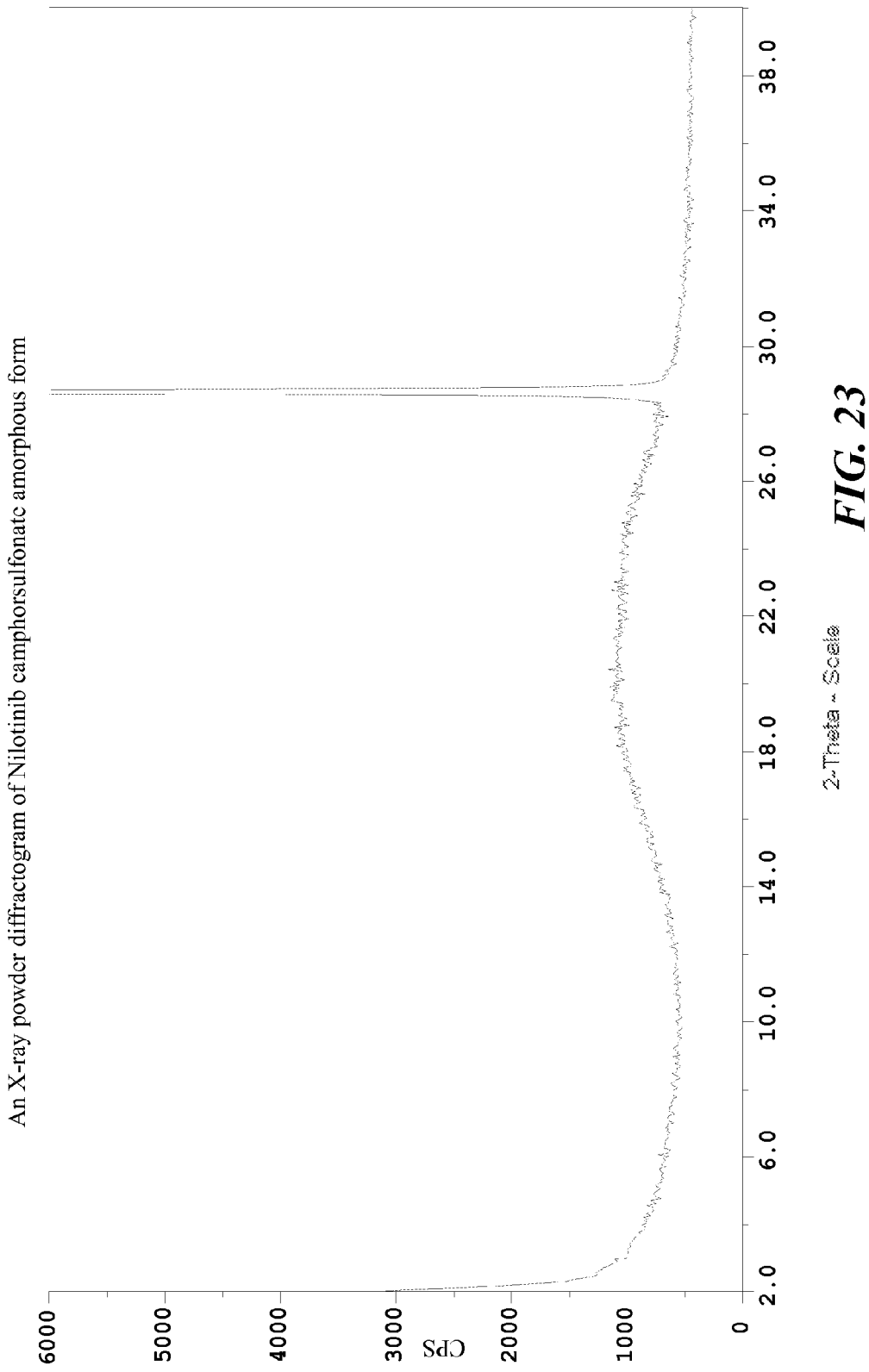
FIG. 23 shows an X-ray powder diffractogram of Nilotinib camphor-sulfonate amorphous form.

The present invention encompasses an amorphous form of Nilotinib camphorsulfonate. The amorphous Nilotinib camphorsulfonate can be characterized by an X-ray powder diffraction pattern substantially as depicted in FIG. 23.

Figure 24:
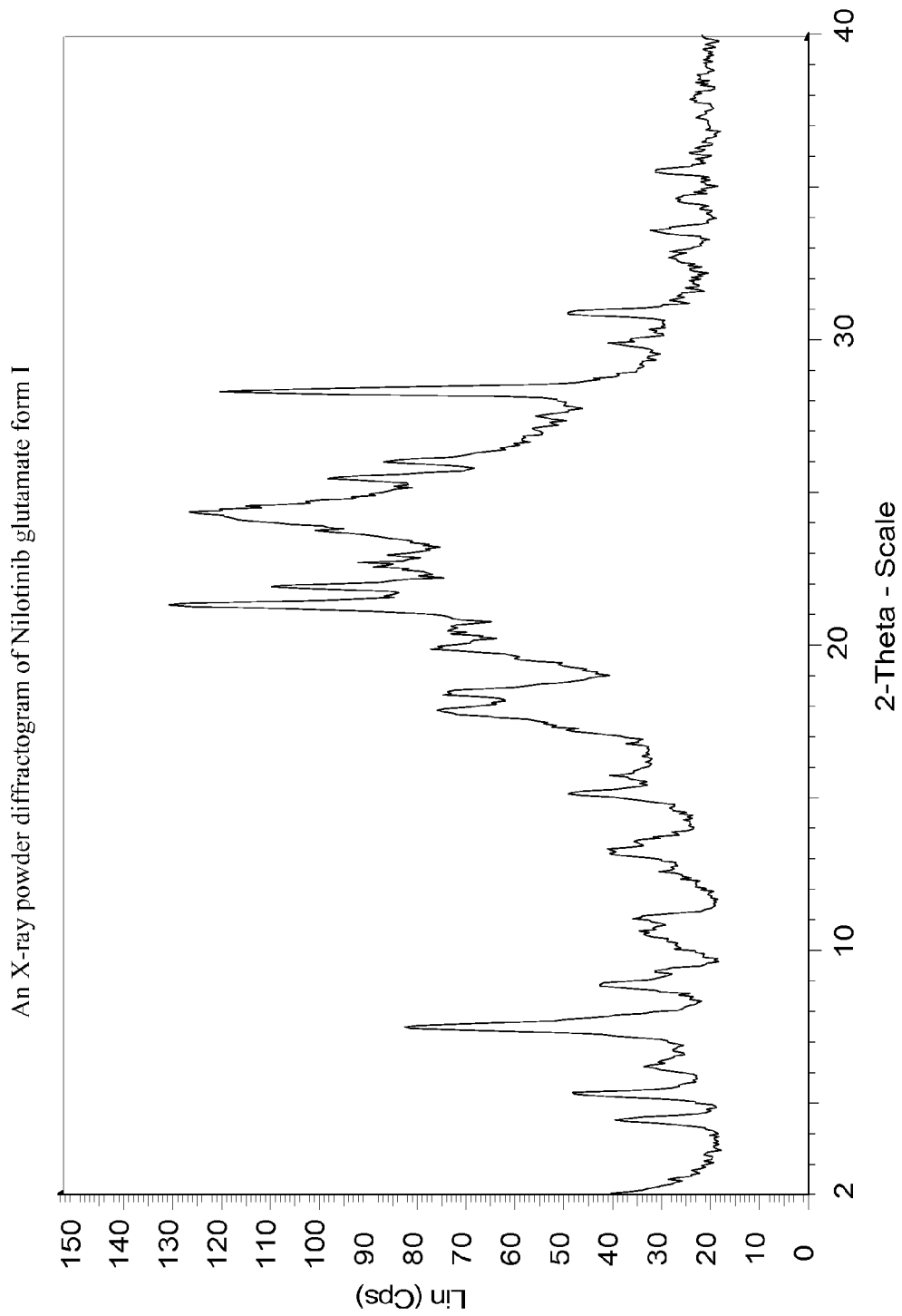
FIG. 24 shows an X-ray powder diffractogram of Nilotinib glutamate crystalline form I.

The present invention encompasses a crystalline form of Nilotinib glutamate, designated as form I. Nilotinib glutamate form I can be characterized by data selected from: an X-ray powder diffraction pattern having peaks at 4.5, 5.5, 7.5, 9.0 and 18.0 degrees two theta±0.2 degrees two theta; an X-ray powder diffraction pattern substantially as depicted in FIG. 24; and combinations thereof. The Nilotinib glutamate form I may be further characterized by additional X-ray powder diffraction pattern peaks at 15.2 and 24.4 degrees two theta±0.2 degrees two theta.

Figure 25:
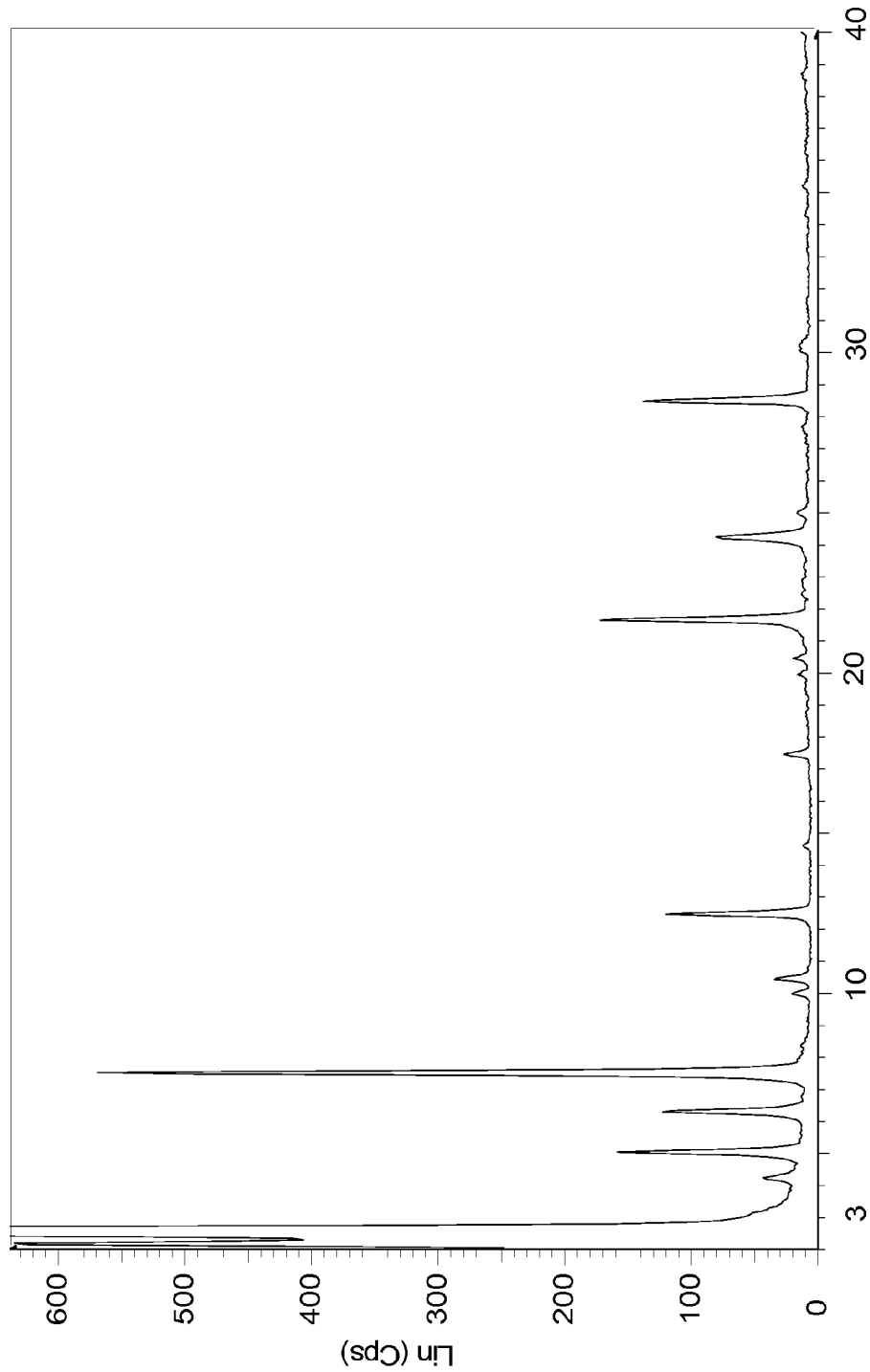
FIG. 25 shows an X-ray powder diffractogram of Nilotinib palmitate crystalline form I.

The present invention encompasses a crystalline form of Nilotinib palmitate, designated as form I. Nilotinib palmitate form I can be characterized by data selected from: an X-ray powder diffraction pattern having peaks at 2.1, 4.1, 6.2, 10.4 and 14.6 degrees two theta±0.2 degrees two theta; an X-ray powder diffraction pattern substantially as depicted in FIG. 25; and combinations thereof.

Figure 26:
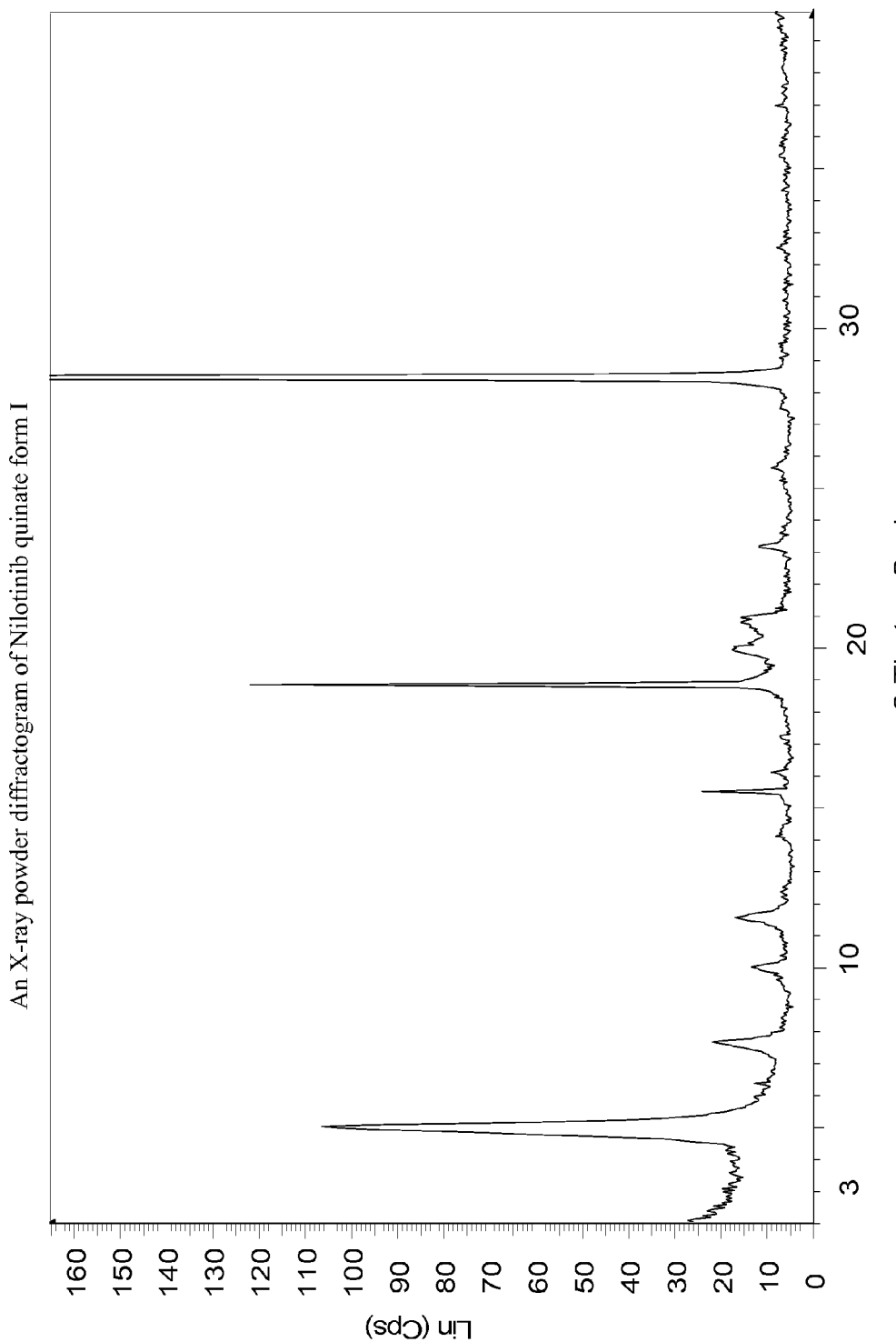
FIG. 26 shows an X-ray powder diffractogram of Nilotinib quinate crystalline form I.

The present invention encompasses a crystalline form of Nilotinib quinate, designated as form I. Nilotinib quinate form I can be characterized by data selected from: an X-ray powder diffraction pattern having peaks at 4.9, 7.6, 10.0, 11.5 and 20.0 degrees two theta±0.2 degrees two theta; an X-ray powder diffraction pattern substantially as depicted in FIG. 26; and combinations thereof. The Nilotinib quinate form I may be further characterized by an additional X-ray powder diffraction peak at 25.7 degrees two theta±0.2 degrees two theta.

Figure 27:
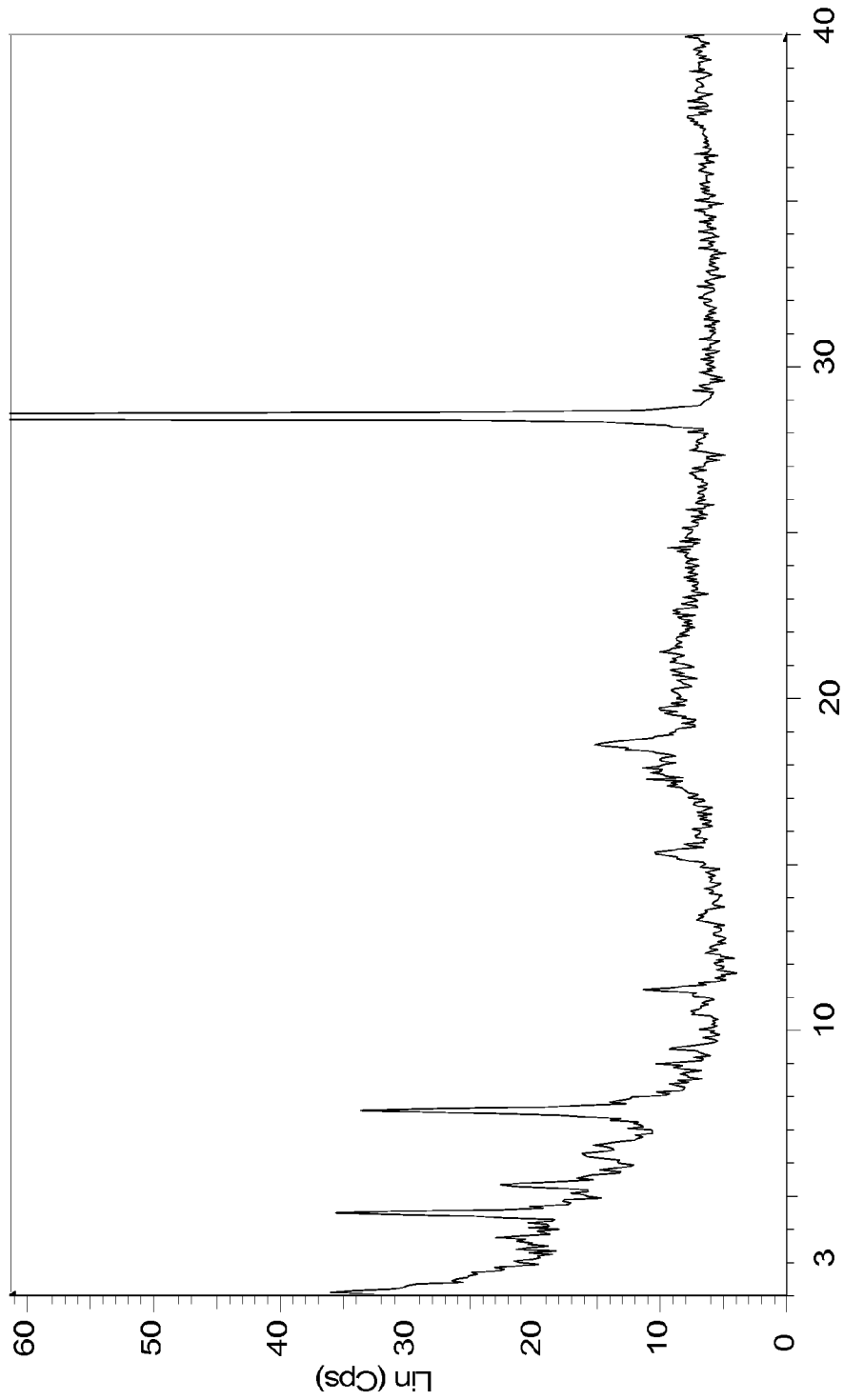
FIG. 27 shows an X-ray powder diffractogram of Nilotinib citrate crystalline form I.

The present invention encompasses a crystalline form of Nilotinib citrate, designated as form I. Nilotinib citrate form I can be characterized by data selected from: an X-ray powder diffraction pattern having peaks at 4.4, 5.2, 7.5, 11.2 and 15.3 degrees two theta±0.2 degrees two theta; an X-ray powder diffraction pattern substantially as depicted in FIG. 27; and combinations thereof. The Nilotinib citrate form I may be further characterized by an additional X-ray powder diffraction peak at 18.6 degrees two theta±0.2 degrees two theta.

The present invention encompasses an amorphous form of Nilotinib citrate. The Amorphous Nilotinib citrate can be characterized by an X-ray powder diffraction pattern substantially as depicted in any one of FIGS. 28-31.

Figure 32:
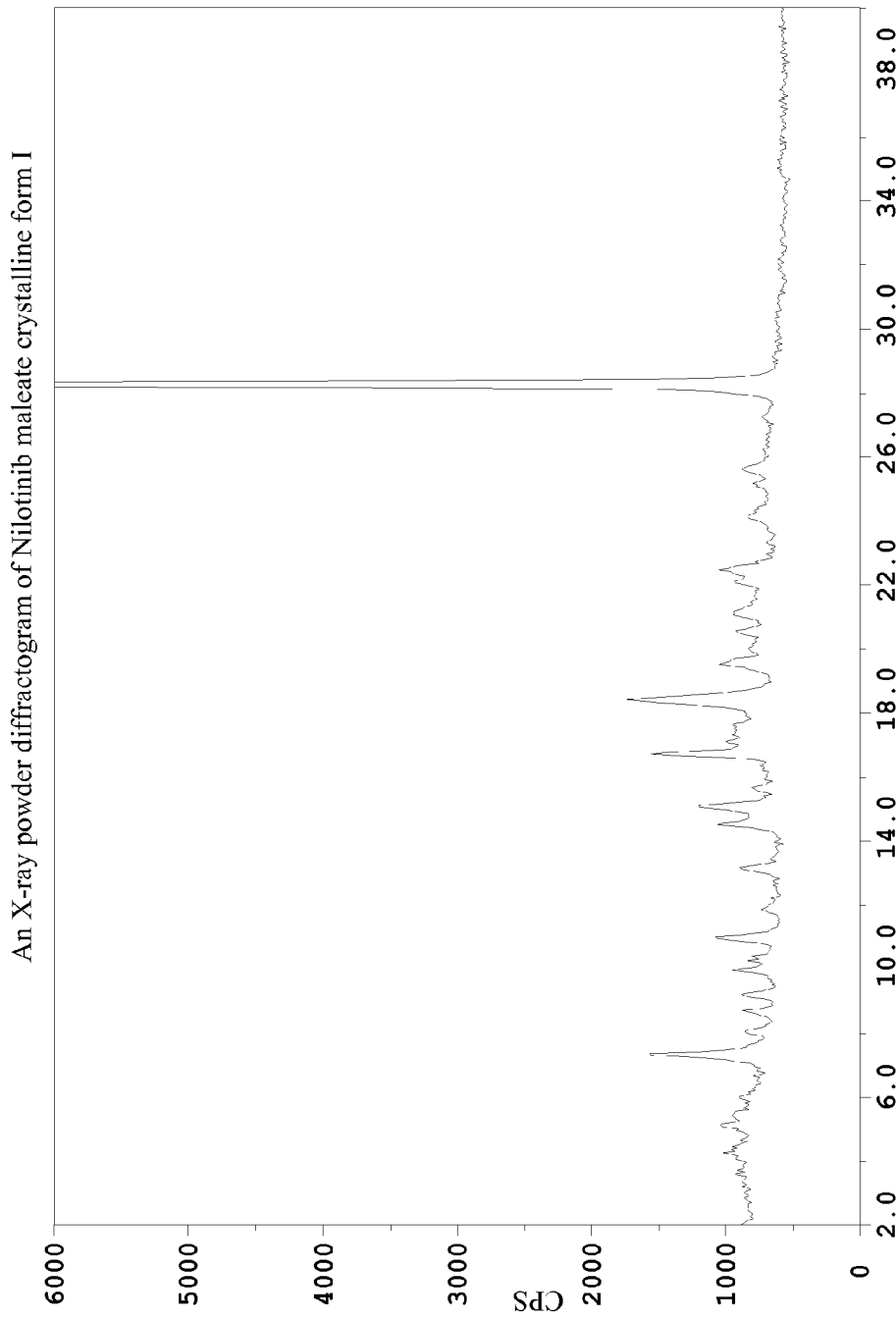
FIG. 32 shows an X-ray powder diffractogram of Nilotinib maleate crystalline form I.

The present invention encompasses a crystalline form of Nilotinib maleate, designated as form I. Nilotinib maleate form I can be characterized by data selected from: an X-ray powder diffraction pattern having peaks at 7.5, 11.1, 15.3, 16.9 and 18.6 degrees two theta±0.2 degrees two theta; an X-ray powder diffraction pattern substantially as depicted in FIG. 32; and combinations thereof. The Nilotinib maleate form I may be further characterized by additional X-ray powder diffraction peaks at 8.2, 9.4, 13.3, 14.7 and 19.7 degrees two theta±0.2 degrees two theta.

Figure 33:
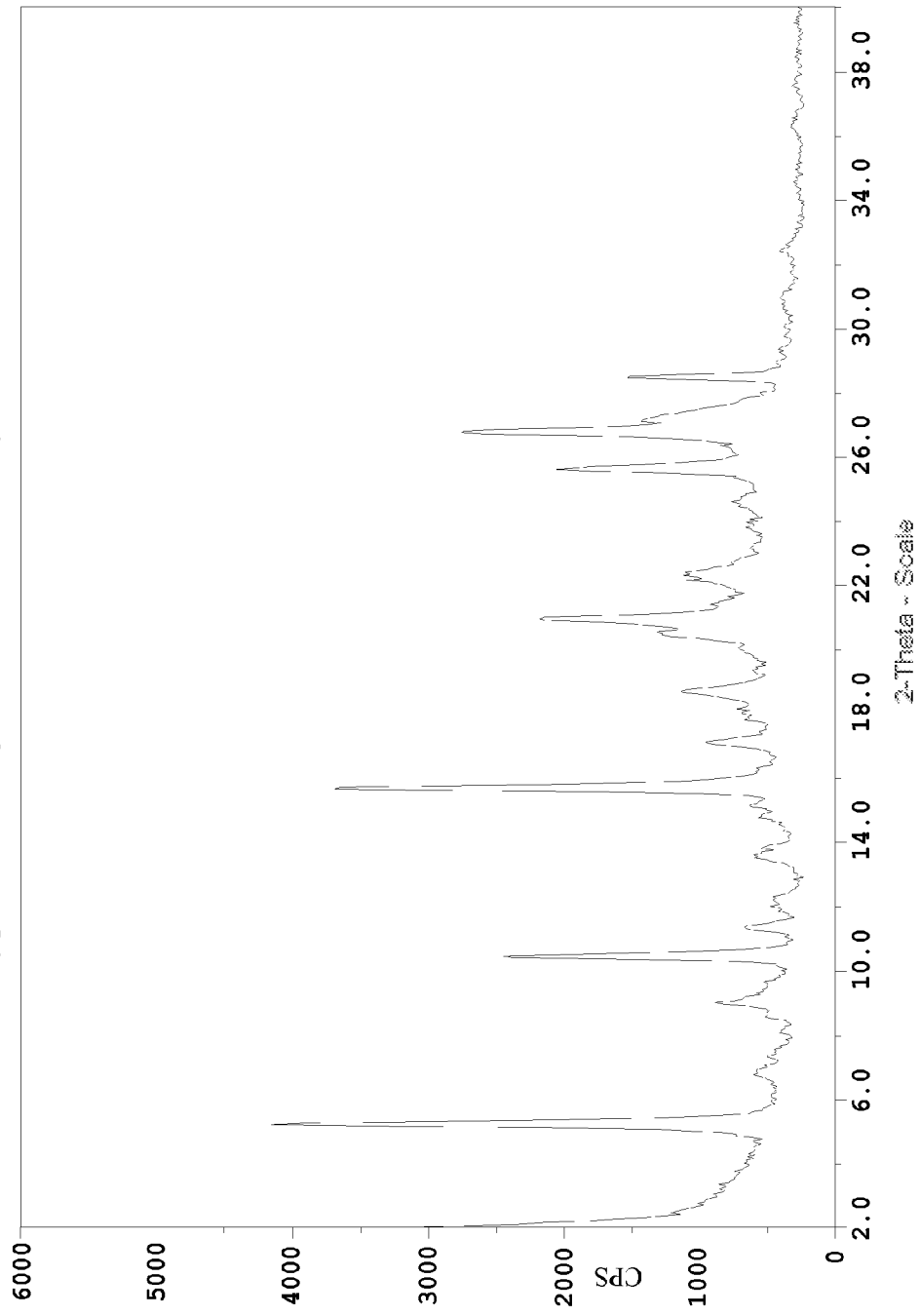
FIG. 33 shows an X-ray powder diffractogram of Nilotinib maleate crystalline form II.

The present invention encompasses a crystalline form of Nilotinib maleate, designated as form II. Nilotinib maleate form II can be characterized by data selected from: an X-ray powder diffraction pattern having peaks at 5.2, 10.4, 15.6, 21.0 and 25.6 degrees two theta±0.2 degrees two theta; an X-ray powder diffraction pattern substantially as depicted in FIG. 33; and combinations thereof. The Nilotinib maleate form II may be further characterized by additional X-ray powder diffraction peaks at 9.0, 17.1, 18.7, 22.3 and 26.8 degrees two theta±0.2 degrees two theta.

Figure 34:
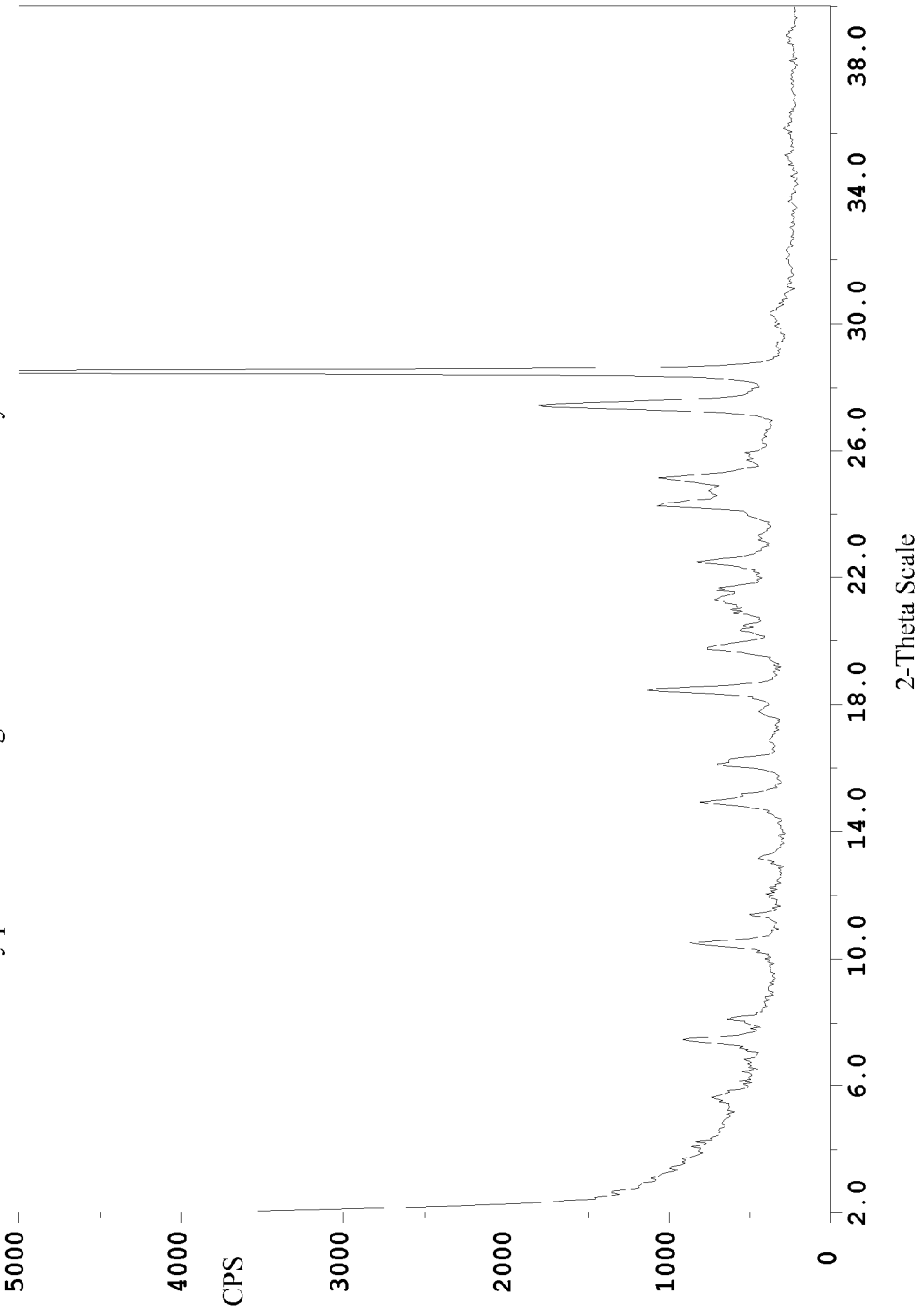
FIG. 34 shows an X-ray powder diffractogram of Nilotinib maleate crystalline form III.

The present invention encompasses a crystalline form of Nilotinib maleate, designated as form III. Nilotinib maleate form III can be characterized by data selected from: an X-ray powder diffraction pattern having peaks at 7.4, 10.4, 14.9, 16.1 and 18.4 degrees two theta±0.2 degrees two theta; an X-ray powder diffraction pattern substantially as depicted in FIG. 34; and combinations thereof. The Nilotinib maleate form III may be further characterized by additional X-ray powder diffraction peaks at 19.7, 22.4, 24.3, 25.1 and 27.4 degrees two theta±0.2 degrees two theta.

Figure 35:
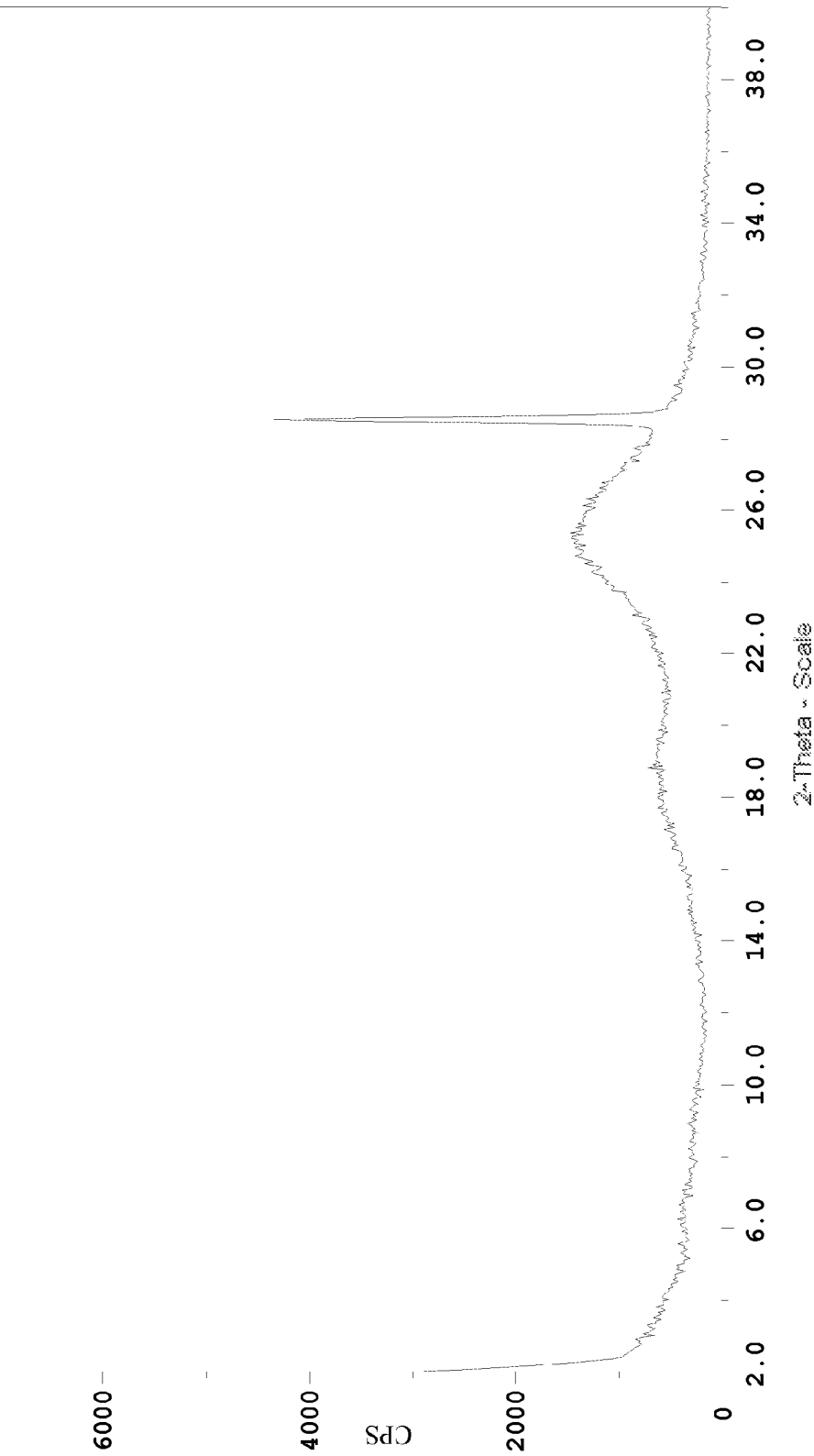
FIG. 35 shows an X-ray powder diffractogram of Nilotinib maleate amorphous form.

The present invention encompasses an amorphous form of Nilotinib maleate. The amorphous Nilotinib maleate can be characterized by an X-ray powder diffraction pattern substantially as depicted in FIG. 35.

Figure 36:
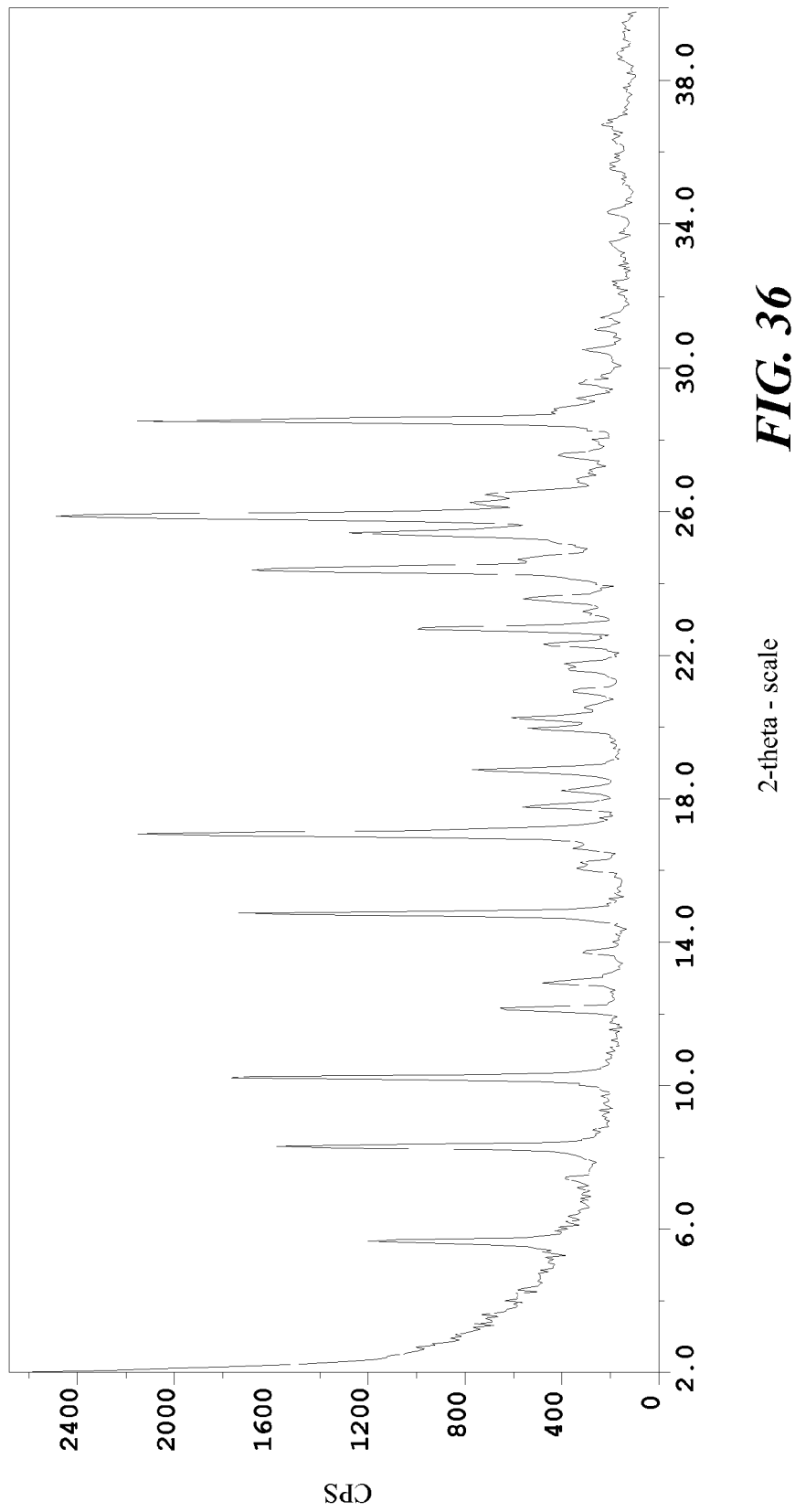
FIG. 36 shows an X-ray powder diffractogram of Nilotinib maleate crystalline form IV.

The present invention encompasses a crystalline form of Nilotinib maleate, designated as form IV. Nilotinib maleate form IV can be characterized by data selected from: an X-ray powder diffraction pattern having peaks at 5.6, 8.3, 10.1, 14.8 and 17.0 degrees two theta±0.2 degrees two theta; an X-ray powder diffraction pattern substantially as depicted in FIG. 36; and combinations thereof. The Nilotinib maleate form IV may be further characterized by additional X-ray powder diffraction peaks at 12.1, 17.7, 18.7, 22.7 and 24.3 degrees two theta±0.2 degrees two theta.

Typically, the Nilotinib maleate form IV can be of Nilotinib monomaleate salt.

Figure 57:
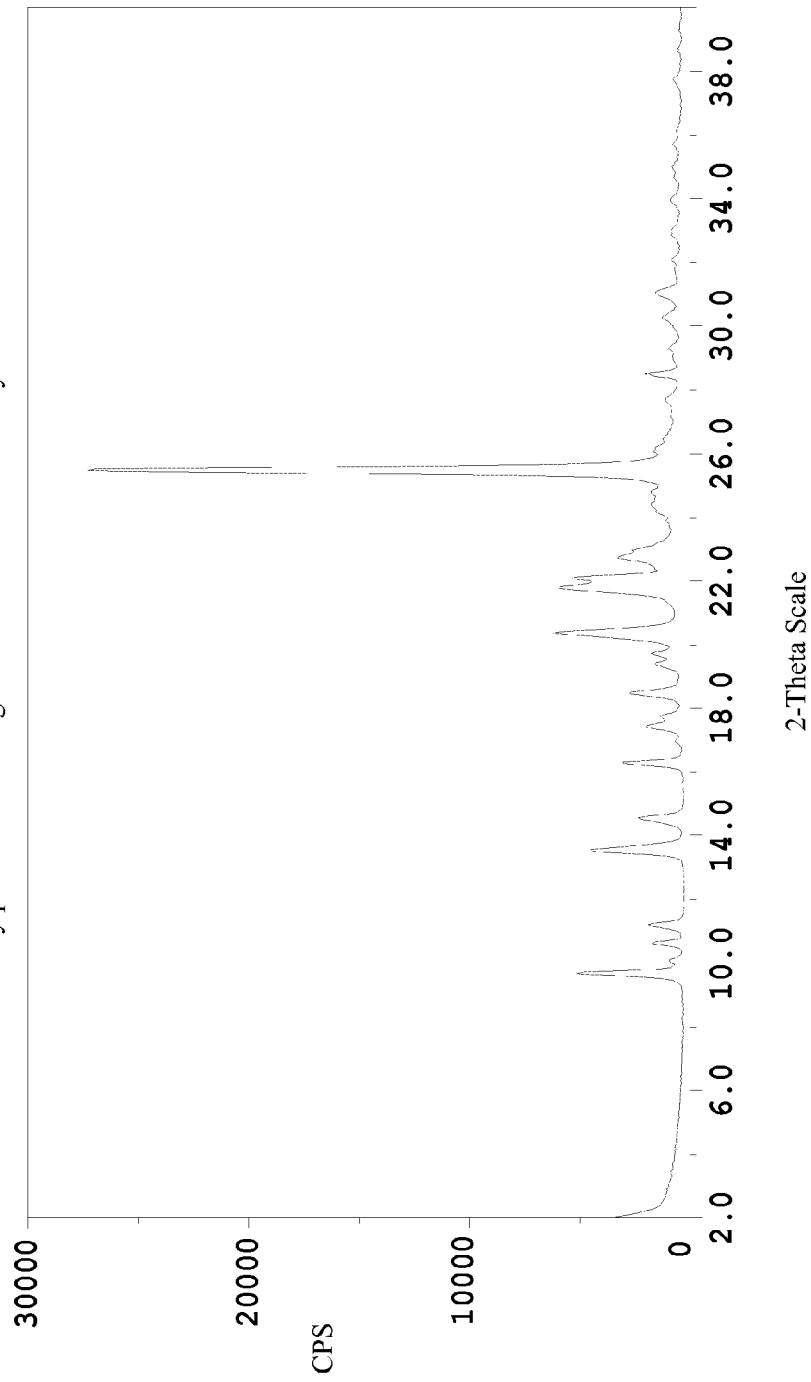
FIG. 57 shows an X-ray powder diffractogram of Nilotinib maleate crystalline form V.

The present invention encompasses a crystalline form of Nilotinib maleate, designated as form V. Nilotinib maleate form V can be characterized by data selected from: an X-ray powder diffraction pattern having peaks at 9.7, 13.5, 16.6, 20.3 and 21.8 degrees two theta±0.2 degrees two theta; an X-ray powder diffraction pattern substantially as depicted in FIG. 57; and combinations thereof. The Nilotinib maleate form V may be further characterized by additional X-ray powder diffraction peaks at 10.6, 11.2, 14.5, 17.4 and 18.4 degrees two theta±0.2 degrees two theta.

Typically, the Nilotinib maleate form V can be of Nilotinib monomaleate salt.

Figure 37:
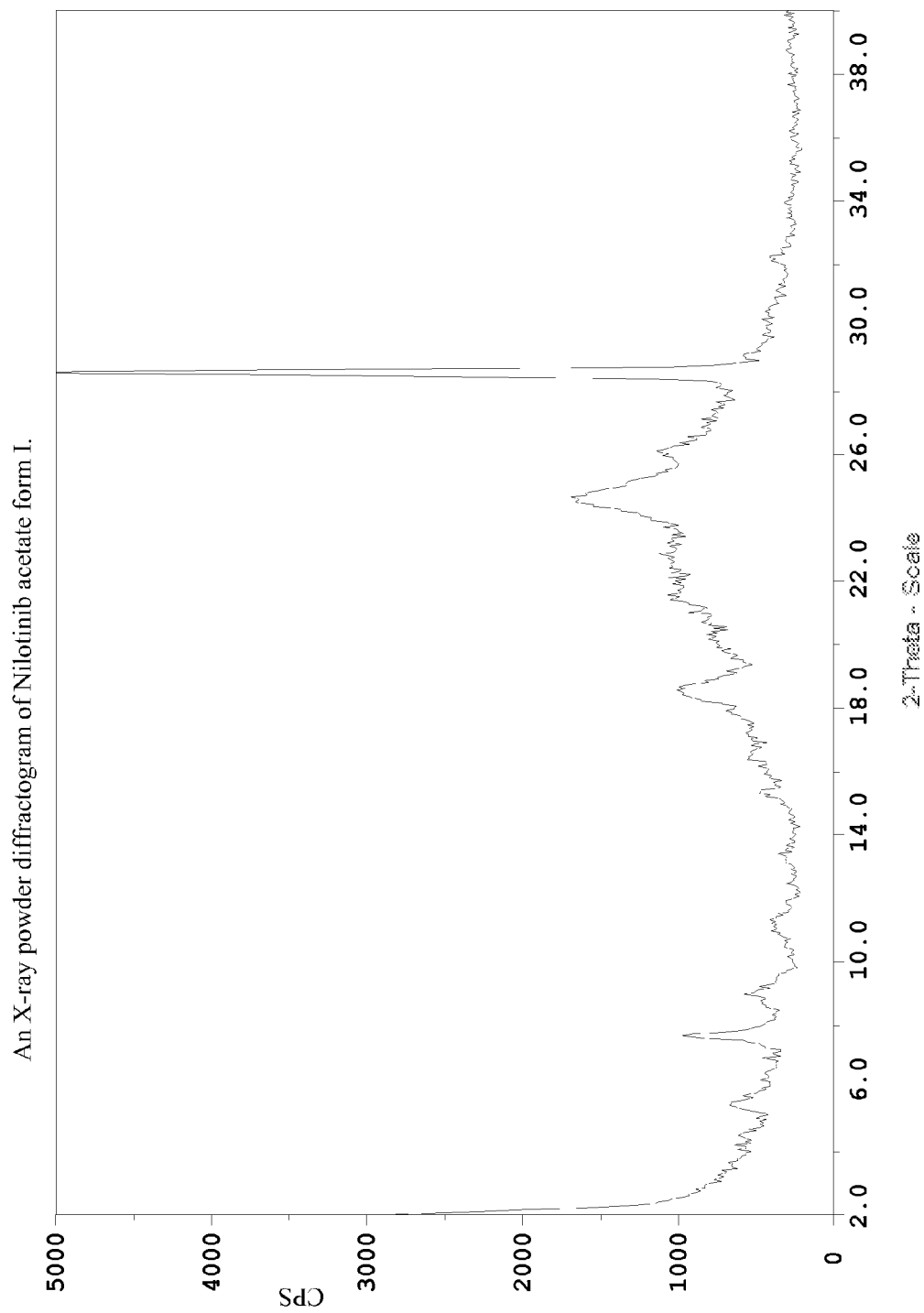
FIG. 37 shows an X-ray powder diffractogram of Nilotinib acetate crystalline form I.

The present invention encompasses a crystalline form of Nilotinib acetate, designated as form I. Nilotinib acetate form I can be characterized by data selected from: an X-ray powder diffraction pattern having peaks at 5.4, 7.6, 8.8 degrees two theta±0.2 degrees two theta and broad peaks having maxima at 18.4 and 24.5 degrees two theta±0.2 degrees two theta; an X-ray powder diffraction pattern substantially as depicted in FIG. 37; and combinations thereof.

Figure 38:
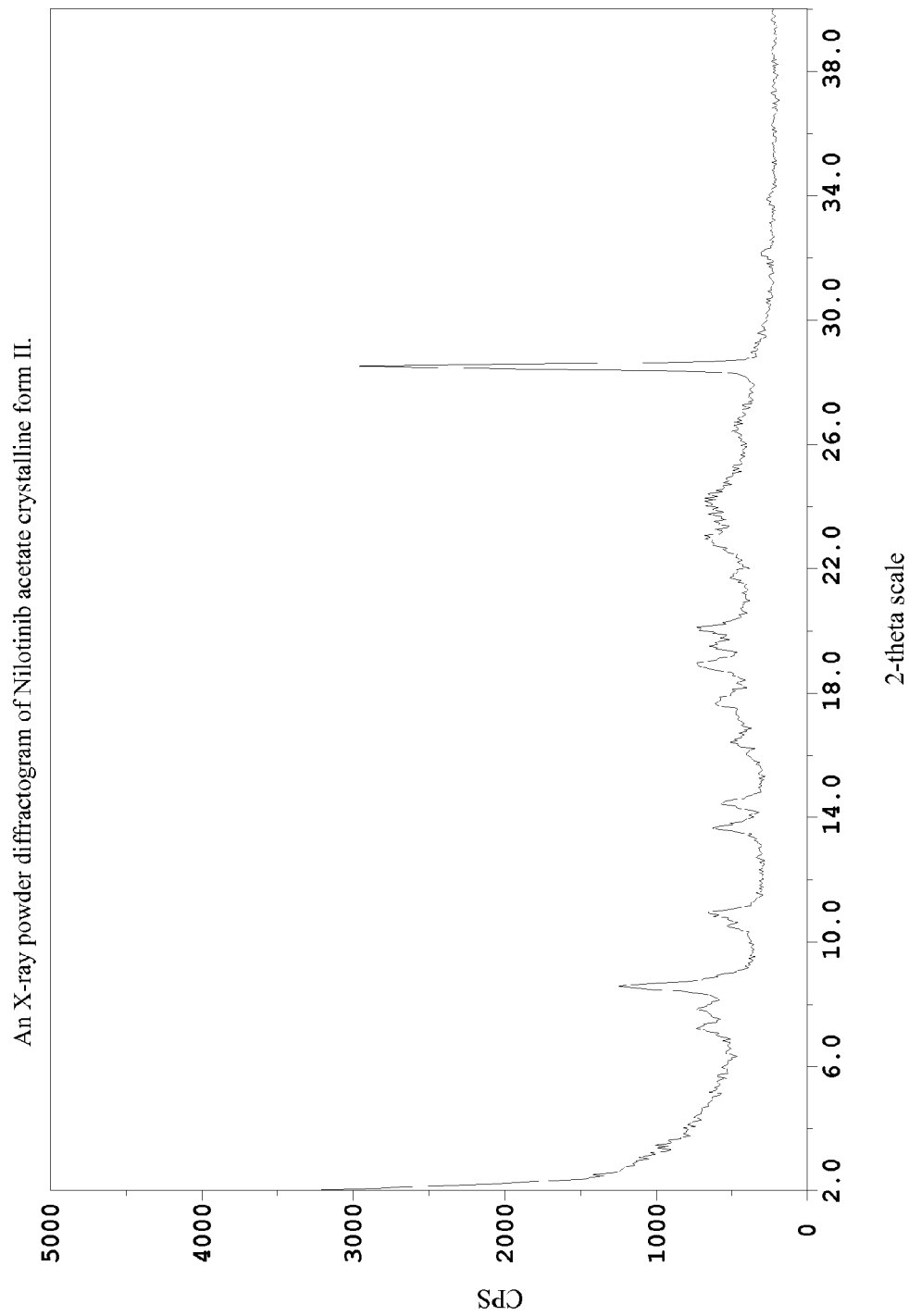
FIG. 38 shows an X-ray powder diffractogram of Nilotinib acetate crystalline form II.

The present invention encompasses a crystalline form of Nilotinib acetate, designated as form II. Nilotinib acetate form II can be characterized by data selected from: an X-ray powder diffraction pattern having peaks at 7.2, 7.8, 8.6, 10.9 and 13.6 degrees two theta±0.2 degrees two theta; an X-ray powder diffraction pattern substantially as depicted in FIG. 38; and combinations thereof. The Nilotinib acetate form II may be further characterized by additional X-ray powder diffraction peaks at 14.4, 17.6, 18.9, 20.1 and 22.9 degrees two theta±0.2 degrees two theta.

Figure 39:
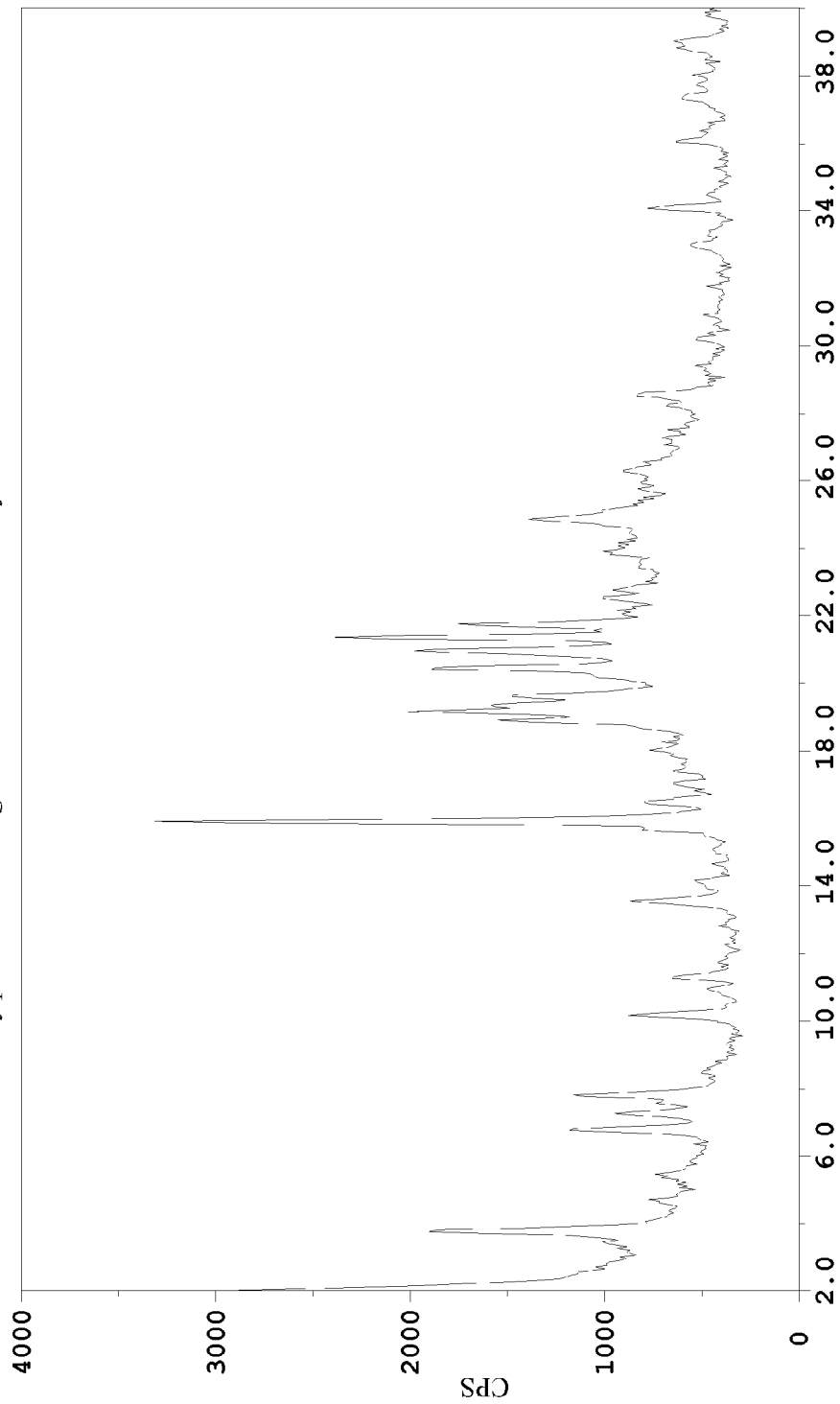
FIG. 39 shows an X-ray powder diffractogram of Nilotinib acetate crystalline form III.

The present invention encompasses a crystalline form of Nilotinib acetate, designated as form III. Nilotinib acetate form III can be characterized by data selected from: an X-ray powder diffraction pattern having peaks at 3.6, 6.7, 10.0, 15.8 and 21.2 degrees two theta±0.2 degrees two theta; an X-ray powder diffraction pattern substantially as depicted in FIG. 39; and combinations thereof. The Nilotinib acetate form III may be further characterized by additional X-ray powder diffraction peaks at 7.7, 19.1, 20.3, 20.9 and 24.7 degrees two theta±0.2 degrees two theta.

Figure 40:
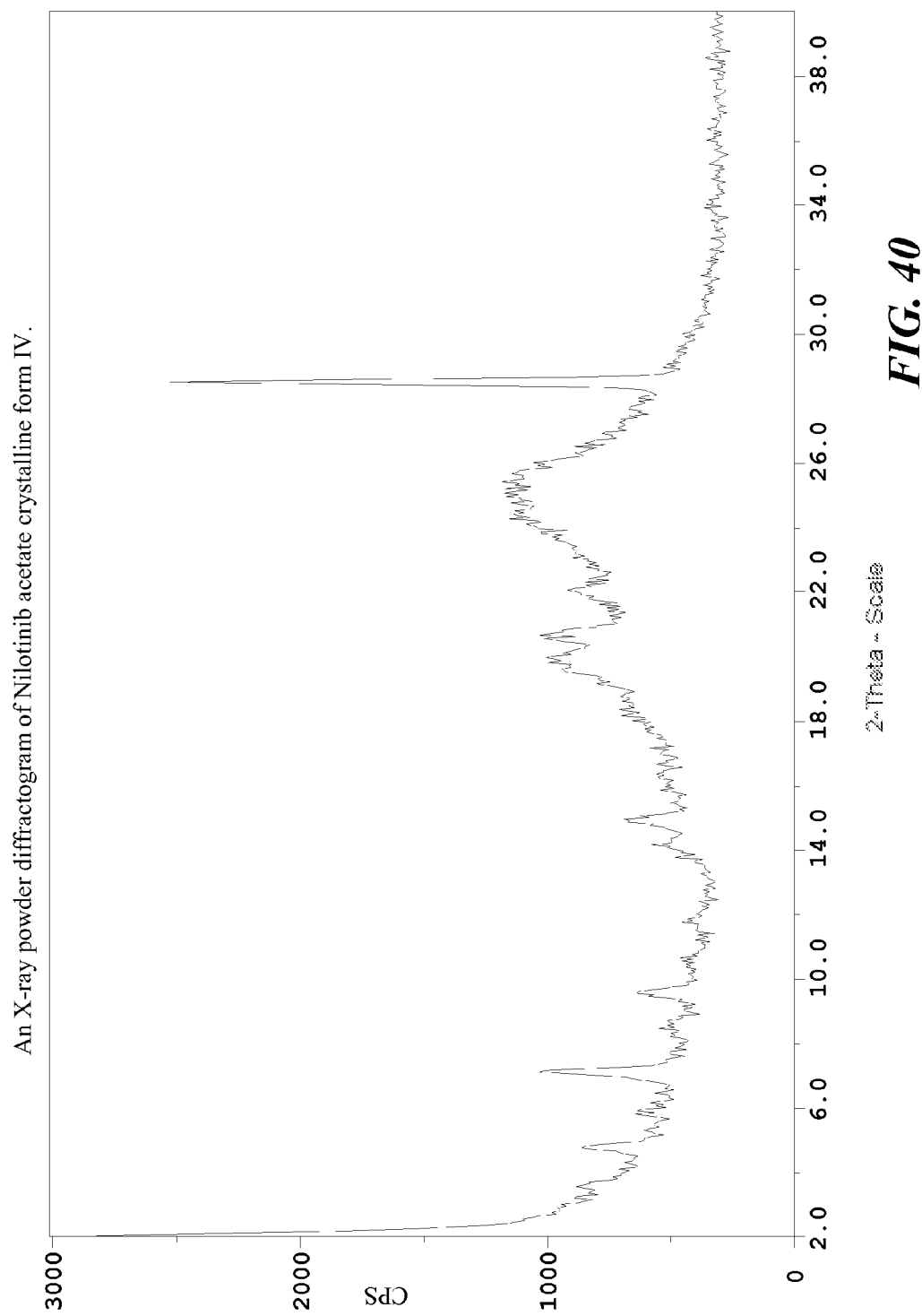
FIG. 40 shows an X-ray powder diffractogram of Nilotinib acetate crystalline form IV.

The present invention encompasses a crystalline form of Nilotinib acetate, designated as form IV. Nilotinib acetate form IV can be characterized by data selected from: an X-ray powder diffraction pattern having peaks at 4.7, 7.1, 9.5 and 14.9 degrees two theta±0.2 degrees two theta and a broad peak having a maximum at 14.1 degrees two theta±0.2 degrees two theta; an X-ray powder diffraction pattern substantially as depicted in FIG. 40; and combinations thereof. The Nilotinib acetate form IV may be further characterized by additional broad X-ray powder diffraction peaks having maxima at 19.8, 20.5 and 21.9 degrees two theta±0.2 degrees two theta.

Figure 41:
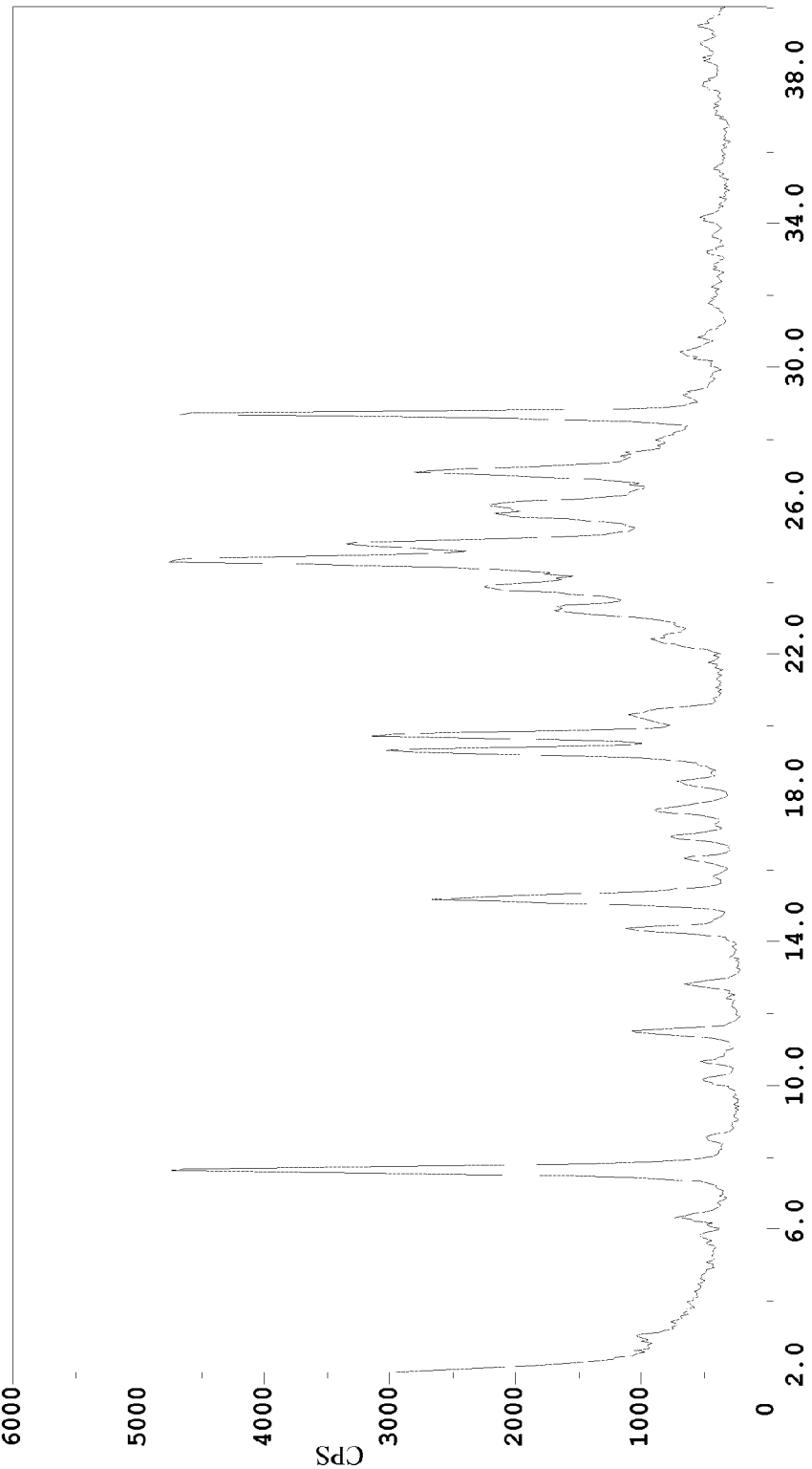
FIG. 41 shows an X-ray powder diffractogram of Nilotinib acetate crystalline form V.

The present invention encompasses a crystalline form of Nilotinib acetate, designated as form V. Nilotinib acetate form V can be characterized by data selected from: an X-ray powder diffraction pattern having peaks at 7.4, 11.3, 14.2, 14.9 and 19.1 degrees two theta±0.2 degrees two theta; an X-ray powder diffraction pattern substantially as depicted in FIG. 41; and combinations thereof. The Nilotinib acetate form V may be further characterized by additional broad X-ray powder diffraction peaks having maxima at 12.6, 17.4, 19.5, 24.3 and 26.9 degrees two theta±0.2 degrees two theta.

Figure 42:
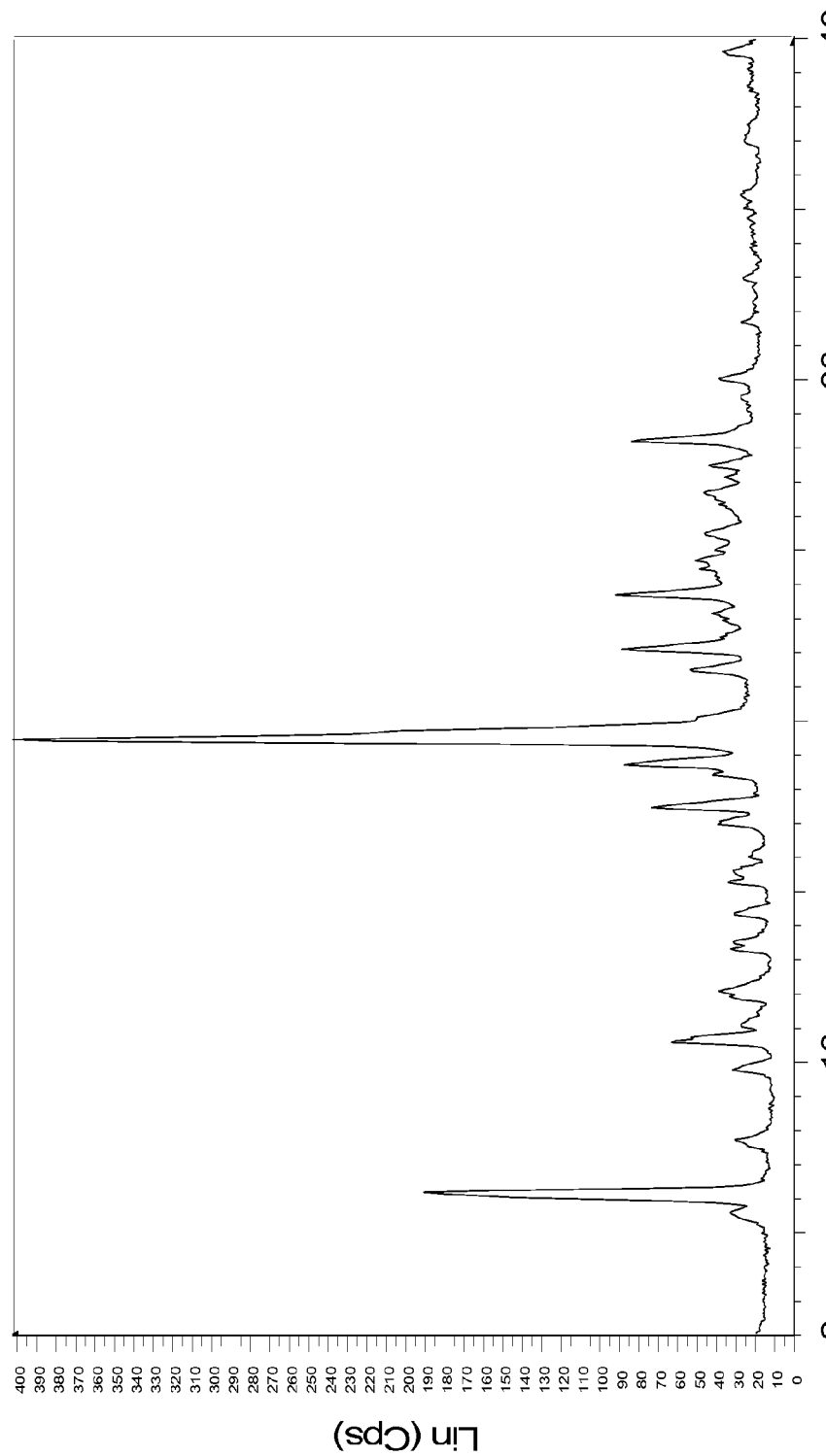
FIG. 42 shows an X-ray powder diffractogram of Nilotinib acetate crystalline form VI.

The present invention encompasses a crystalline form of Nilotinib acetate, designated as form VI. Nilotinib acetate form VI can be characterized by data selected from: an X-ray powder diffraction pattern having peaks at 6.4, 10.8, 17.7, 19.0 and 19.7 degrees two theta±0.2 degrees two theta; an X-ray powder diffraction pattern substantially as depicted in FIG. 42; and combinations thereof. The Nilotinib acetate form VI may be further characterized by additional broad X-ray powder diffraction peaks having maxima at 7.9, 12.3, 21.7, 22.4 and 24.0 degrees two theta±0.2 degrees two theta.

Figure 43:
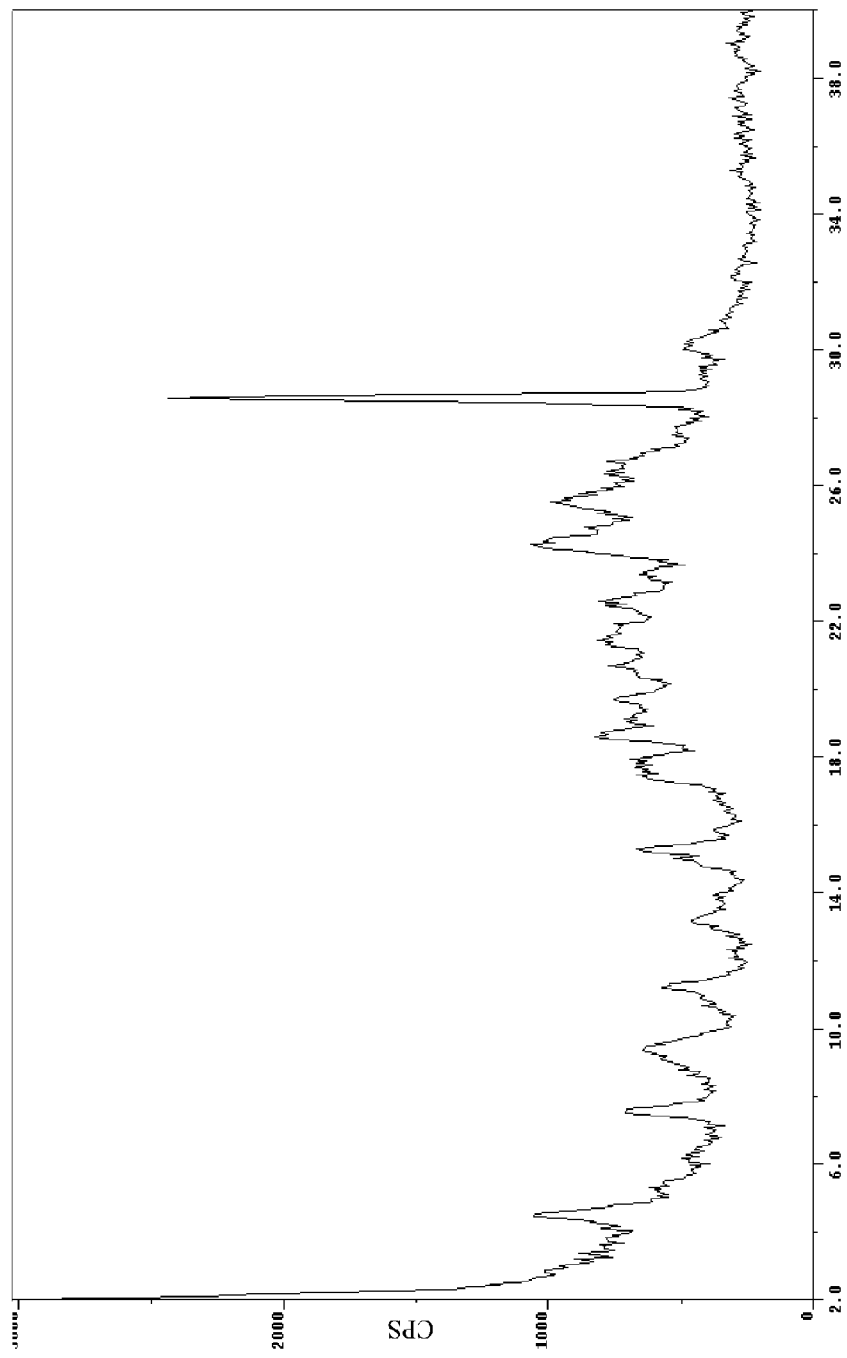
FIG. 43 shows an X-ray powder diffractogram of Nilotinib L-malate crystalline form I.

The present invention encompasses a crystalline form of Nilotinib L-malate, designated as form I. Nilotinib L-malate form I can be characterized by data selected from: an X-ray powder diffraction pattern having peaks at 4.5, 7.5, 9.3, 11.2 and 15.2 degrees two theta±0.2 degrees two theta; an X-ray powder diffraction pattern substantially as depicted in FIG. 43; and combinations thereof. The Nilotinib L-malate form I may be further characterized by additional X-ray powder diffraction peaks at 18.6, 19.7, 22.5, 24.2 and 25.5 degrees two theta±0.2 degrees two theta.

Figure 44:
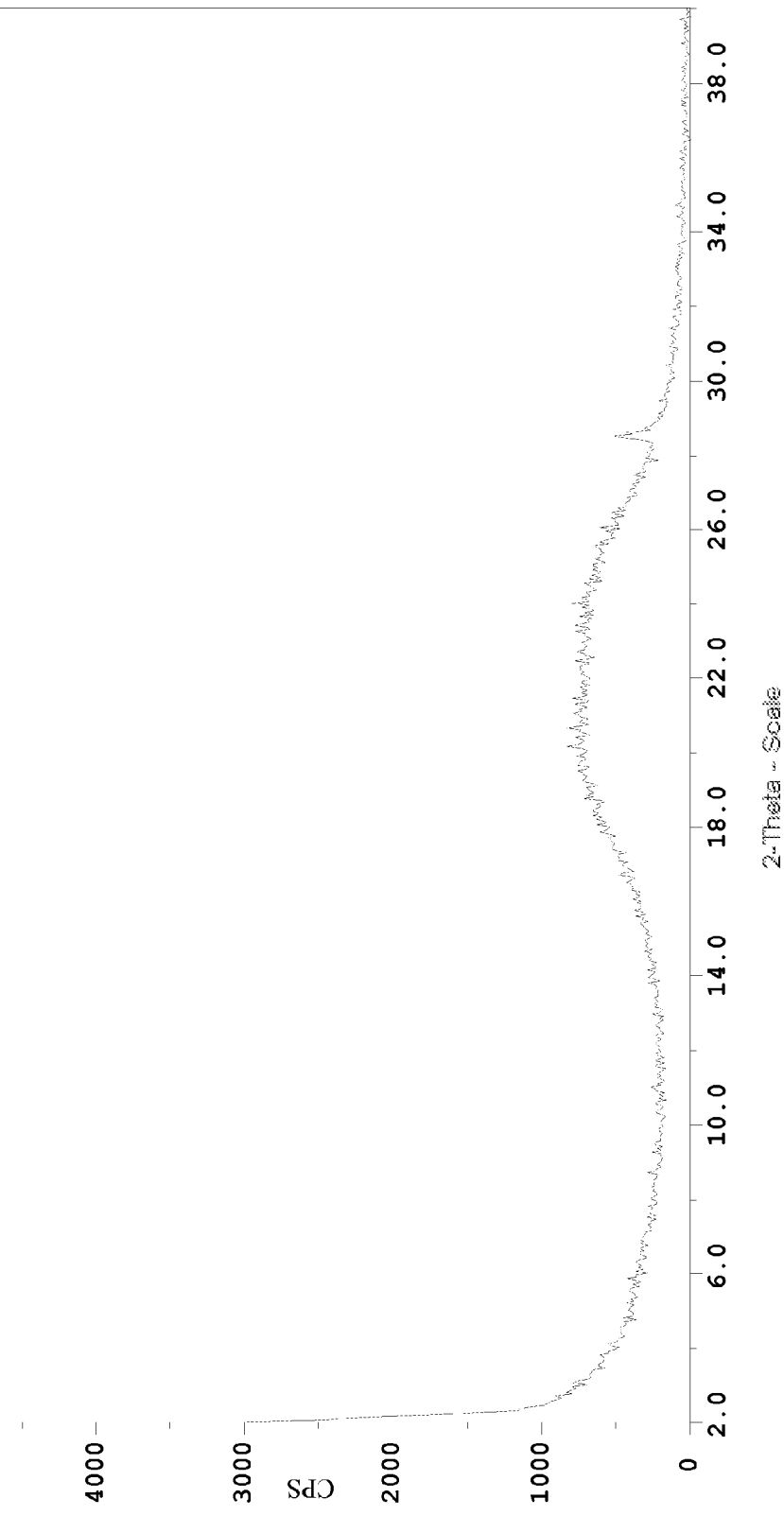
FIG. 44 shows an X-ray powder diffractogram of Nilotinib L-malate amorphous form.
Figure 45:
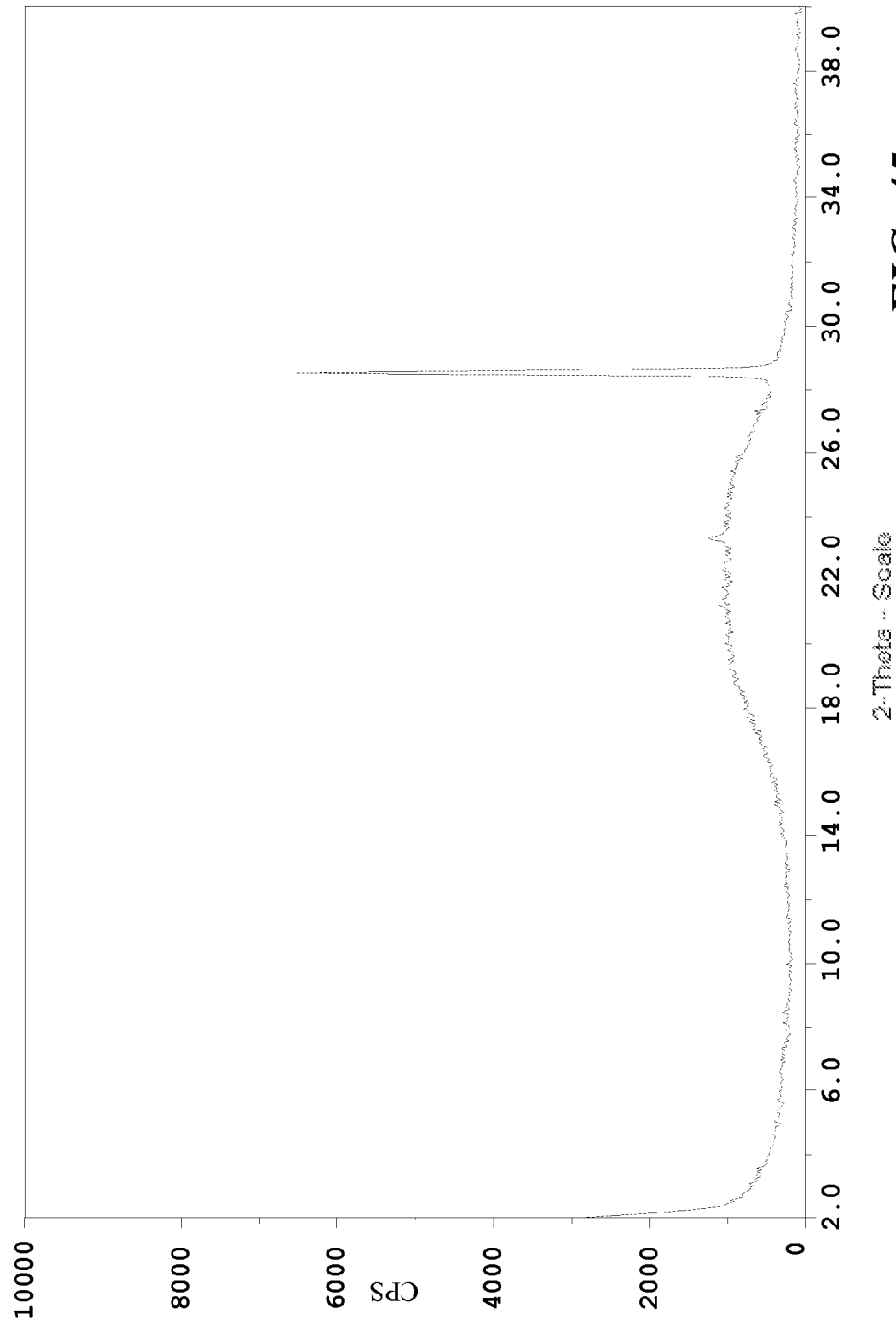
FIG. 45 shows an X-ray powder diffractogram of Nilotinib L-malate amorphous form.
Figure 46:
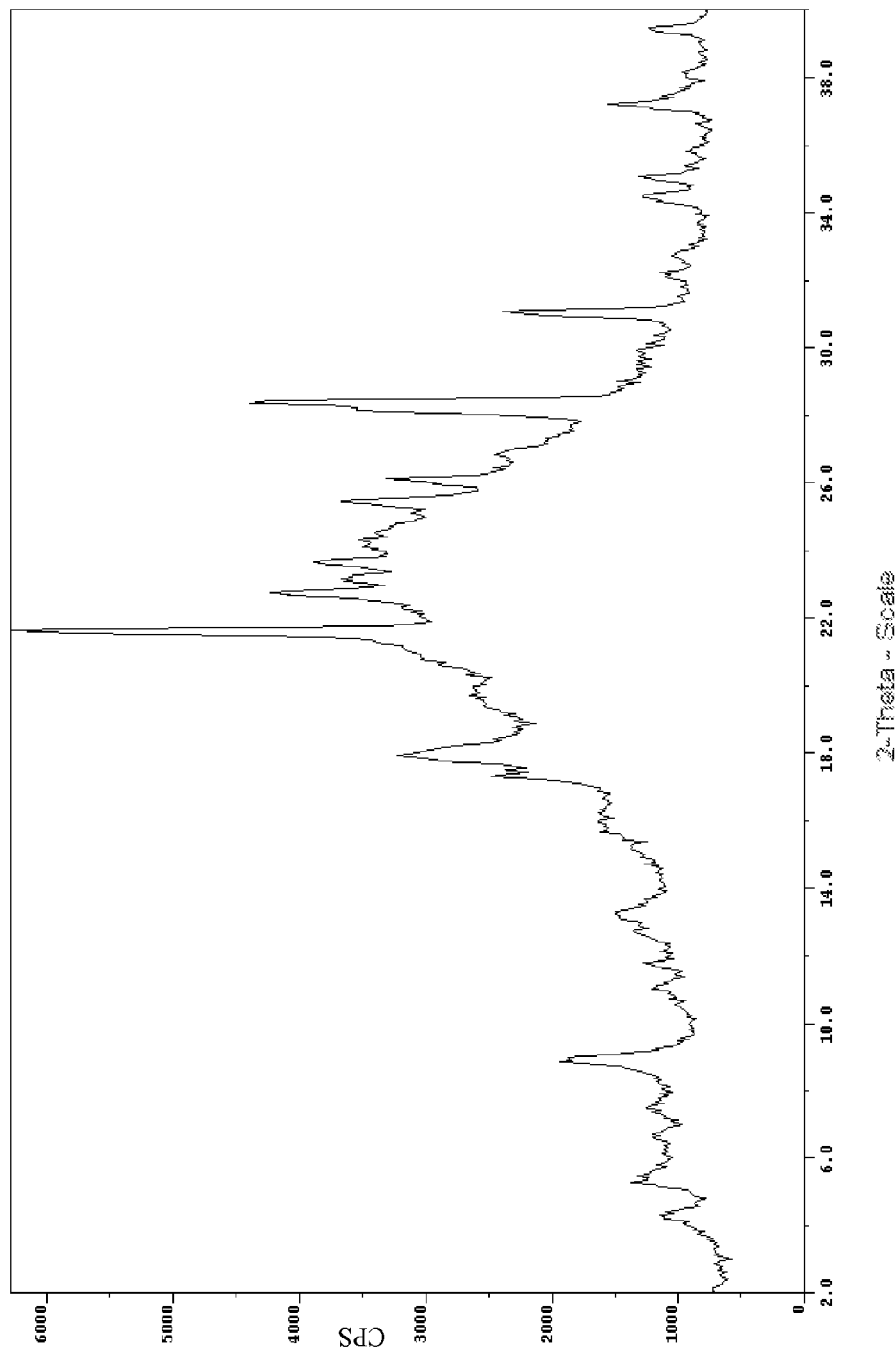
FIG. 46 shows an X-ray powder diffractogram of Nilotinib L-aspartate crystalline form I.

The present invention encompasses an amorphous form of Nilotinib L-malate. The amorphous Nilotinib L-malate can be characterized by an X-ray powder diffraction pattern substantially as depicted in FIG. 44 or FIG. 45.

Figure 47:
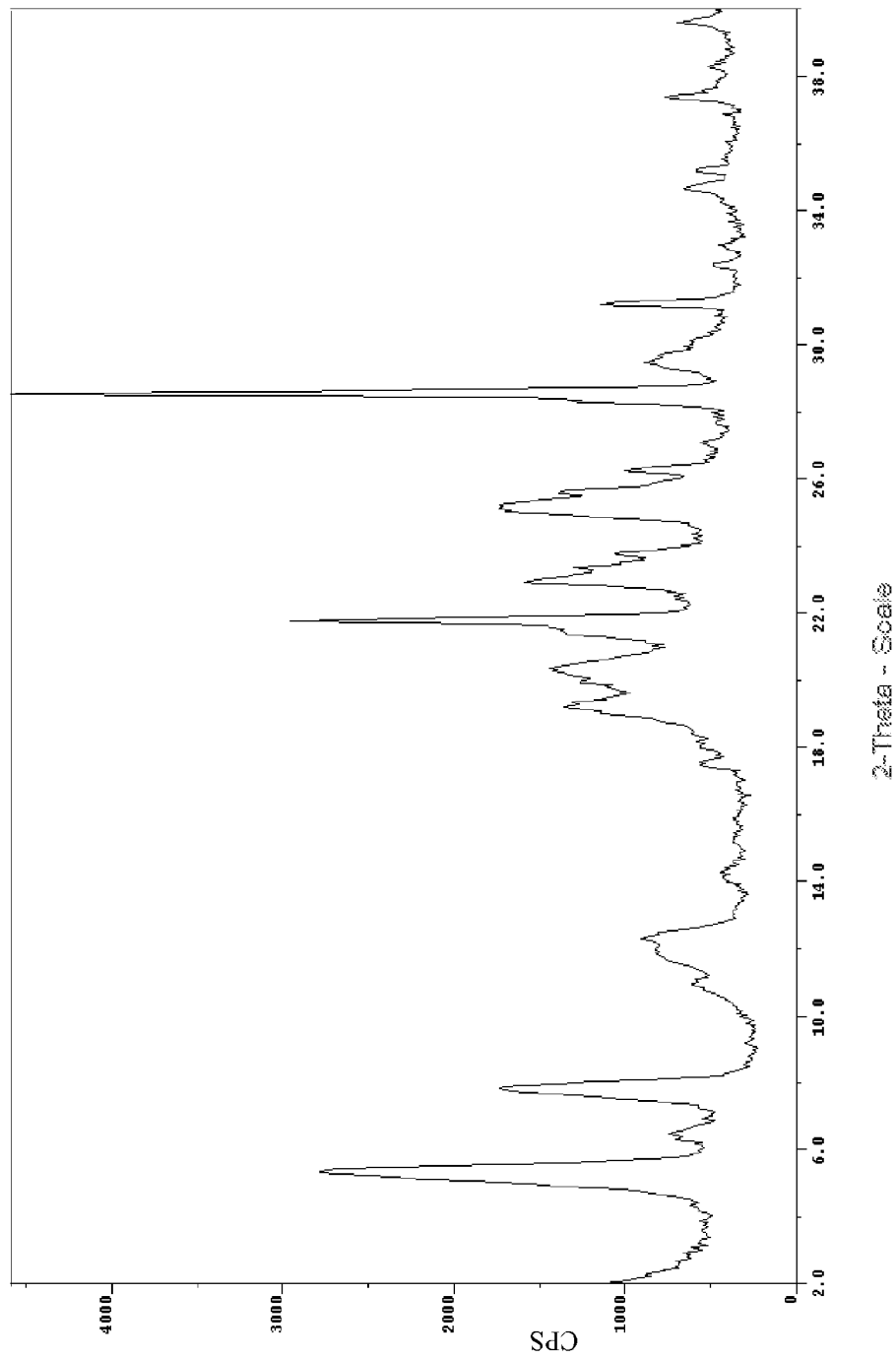
FIG. 47 shows an X-ray powder diffractogram of Nilotinib L-aspartate crystalline form II.

The present invention encompasses a crystalline form of Nilotinib L-aspartate, designated as form I. Nilotinib L-aspartate form I can be characterized by data selected from: an X-ray powder diffraction pattern having peaks at 4.4, 5.4, 9.0 and 18.0 degrees two theta±0.2 degrees two theta; an X-ray powder The present invention encompasses a crystalline form of Nilotinib L-aspartate, designated as form II. Nilotinib L-aspartate form II can be characterized by data selected from: an X-ray powder diffraction pattern having peaks at 5.3, 7.8, 10.9, 19.3 and 25.1 degrees two theta±0.2 degrees two theta; an X-ray powder diffraction pattern substantially as depicted in FIG. 47; and combinations thereof. The Nilotinib L-aspartate form II may be further characterized by additional X-ray powder diffraction peaks at 6.2, 20.3 and 29.2 degrees two theta±0.2 degrees two theta.

Figure 48:
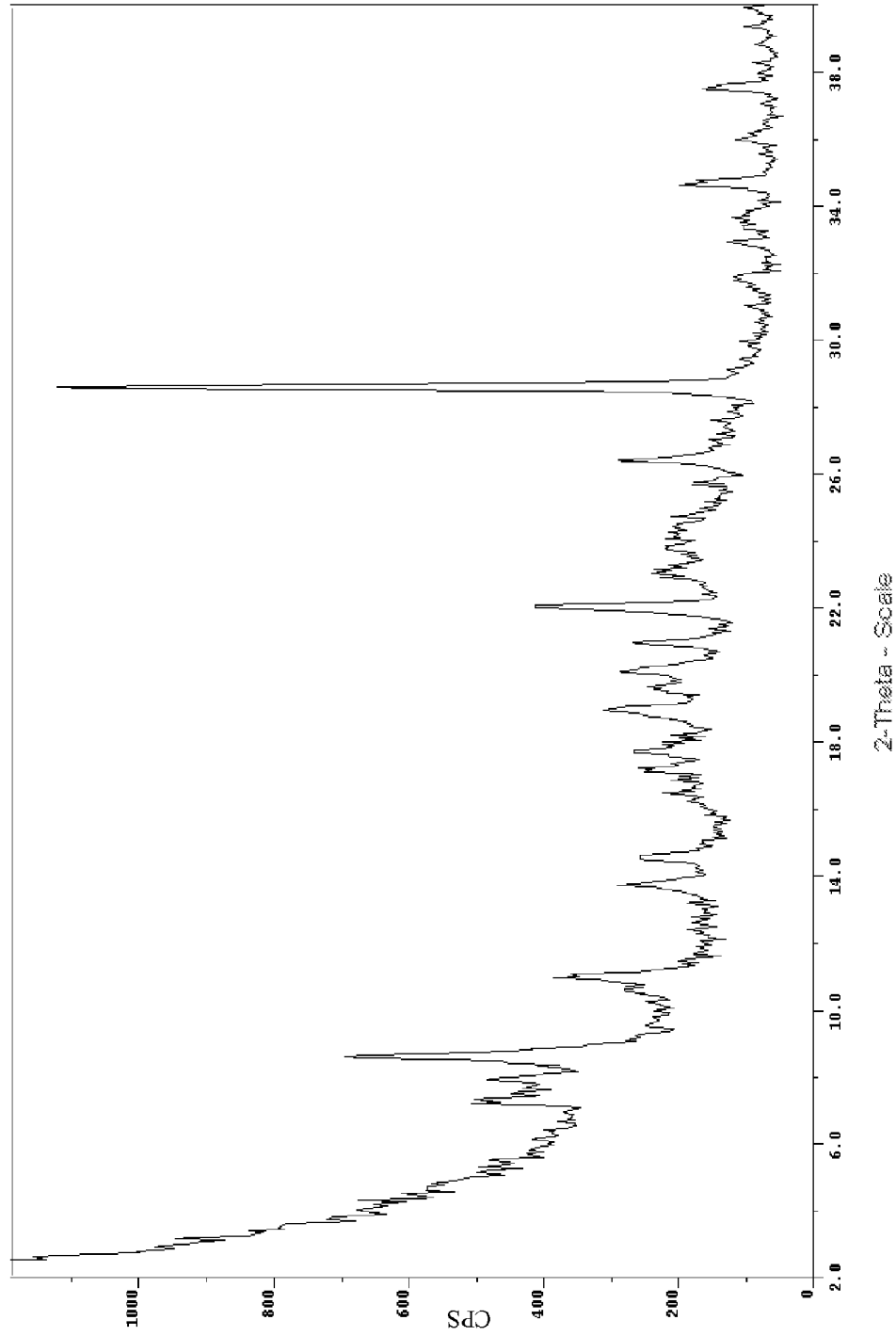
FIG. 48 shows an X-ray powder diffractogram of Nilotinib L-aspartate crystalline form III.

The present invention encompasses a crystalline form of Nilotinib L-aspartate, designated as form III. Nilotinib L-aspartate form III can be characterized by data selected from: an X-ray powder diffraction pattern having peaks at 7.2, 8.6, 13.7, 14.5 and 20.9 degrees two theta±0.2 degrees two theta; an X-ray powder diffraction pattern substantially as depicted in FIG. 48; and combinations thereof. The Nilotinib L-aspartate form III may be further characterized by additional X-ray powder diffraction peaks at 11.0, 18.9, 19.6, 20.1 and 22.0 degrees two theta±0.2 degrees two theta.

Figure 49:
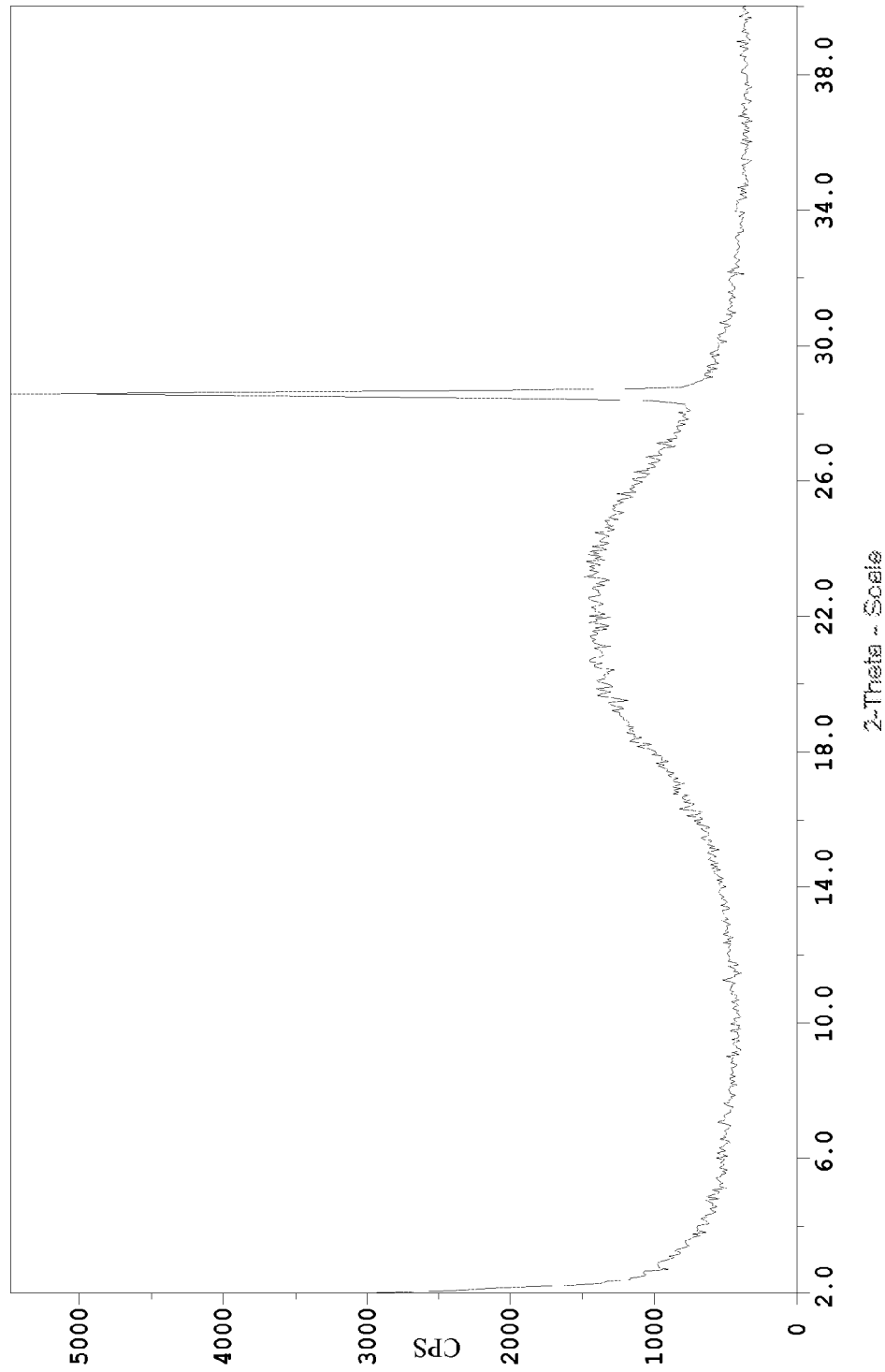
FIG. 49 shows an X-ray powder diffractogram of Nilotinib formate amorphous form.
Figure 50:
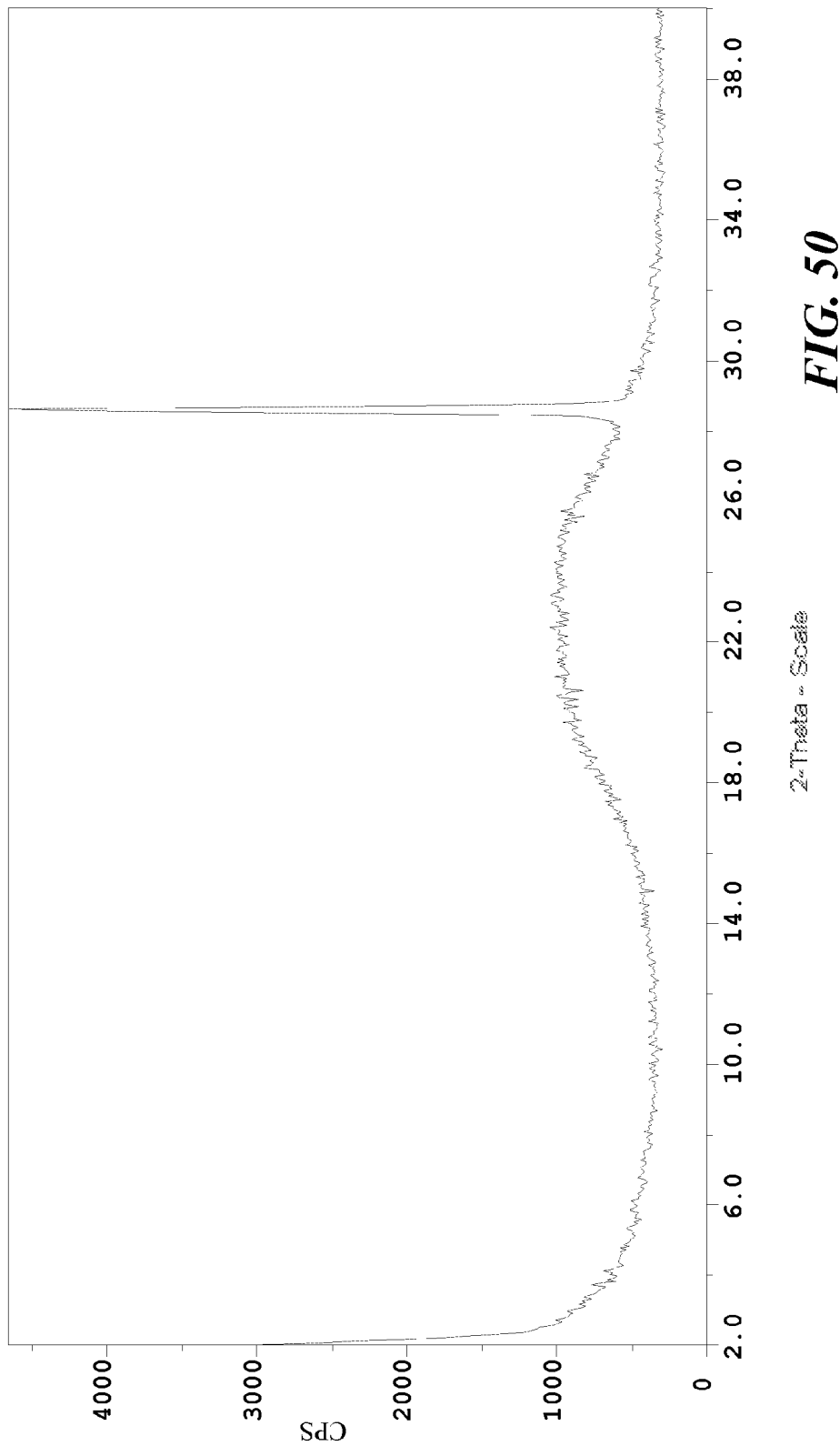
FIG. 50 shows an X-ray powder diffractogram of Nilotinib formate amorphous form.

The present invention encompasses an amorphous form of Nilotinib formate. The amorphous Nilotinib formate can be characterized by an X-ray powder diffraction pattern substantially as depicted in FIG. 49 or FIG. 50.

Figure 51:
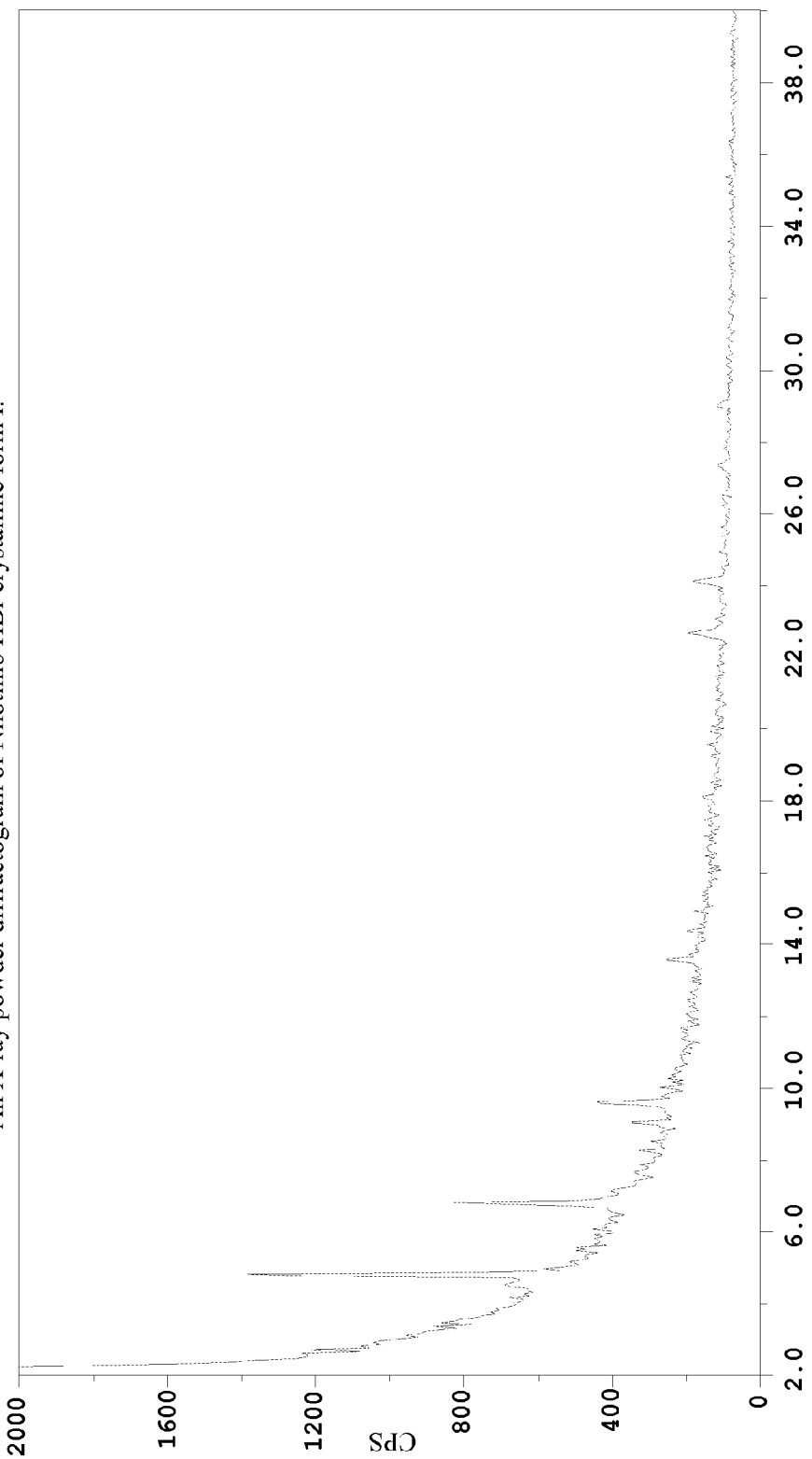
FIG. 51 shows an X-ray powder diffractogram of Nilotinib hydrobromide crystalline form I.

The present invention encompasses a crystalline form of Nilotinib hydro-bromide (HBr), designated as form I. Nilotinib HBr form I can be characterized by data selected from: an X-ray powder diffraction pattern having peaks at 4.8, 6.8, 9.0, 9.6 and 13.6 degrees two theta±0.2 degrees two theta; an X-ray powder diffraction pattern substantially as depicted in FIG. 51; and combinations thereof. The Nilotinib HBr form I may be further characterized by an X-ray powder diffraction pattern having one, two, three, four or five peaks selected from 4.5, 22.7, 24.1, 27.3 and 29.0 degrees two theta±0.2 degrees two theta.

Figure 52:
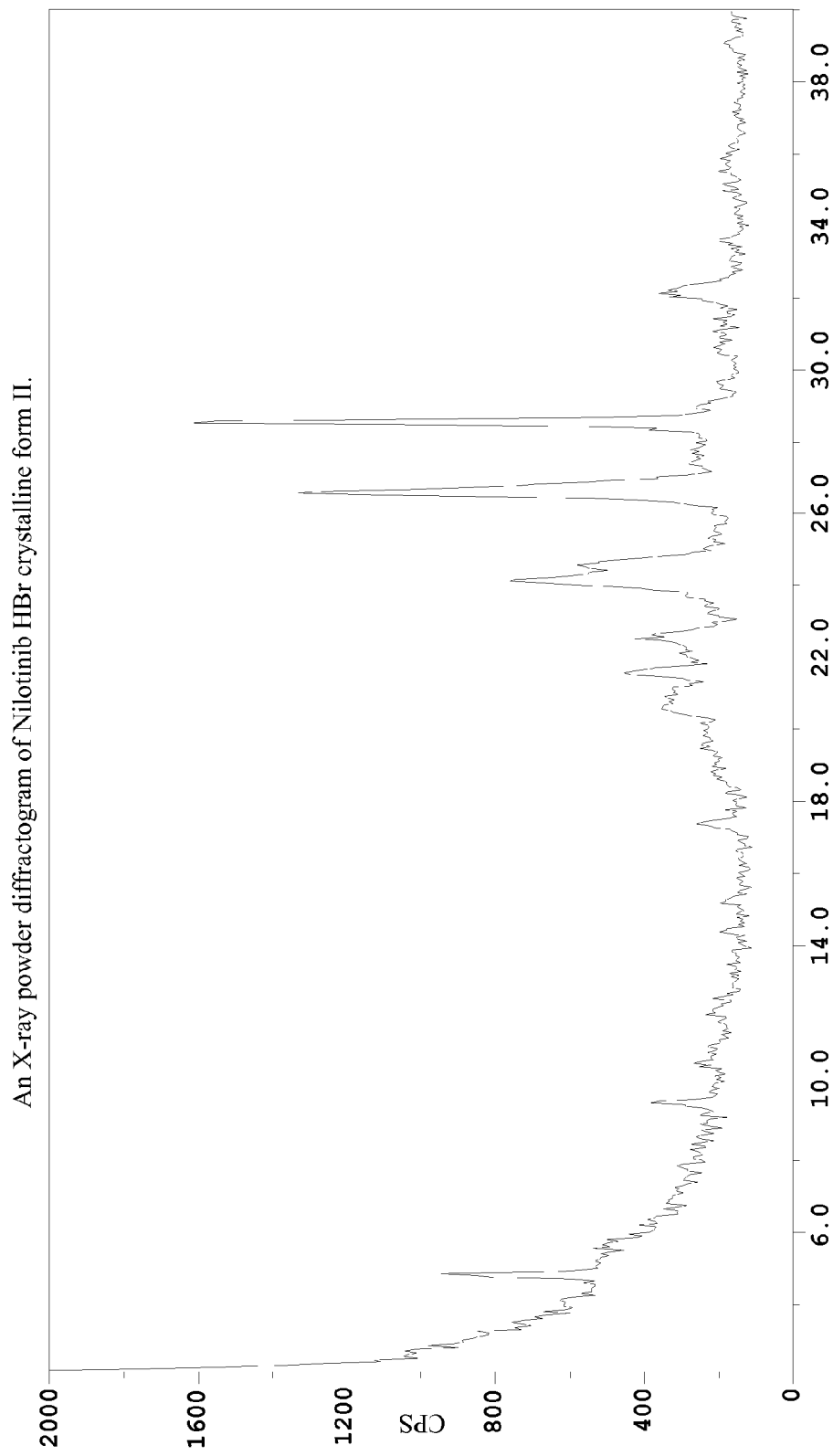
FIG. 52 shows an X-ray powder diffractogram of Nilotinib hydrobromide crystalline form II.

The present invention encompasses a crystalline form of Nilotinib HBr, designated as form II can be characterized by data selected from: an X-ray powder diffraction pattern having peaks at 17.3, 21.5, 24.5 and 26.5 degrees two theta±0.2 degrees two theta and a broad peak having a maximum at 20.8 degrees two theta±0.2 degrees two theta; an X-ray powder diffraction pattern substantially as depicted in FIG. 52; and combinations thereof. The Nilotinib HBr form II may be further characterized by an X-ray powder diffraction pattern having one, two, three, four or five peaks selected from 4.8, 9.5, 22.5, 24.0 and 32.1 degrees two theta±0.2 degrees two theta.

Figure 53:
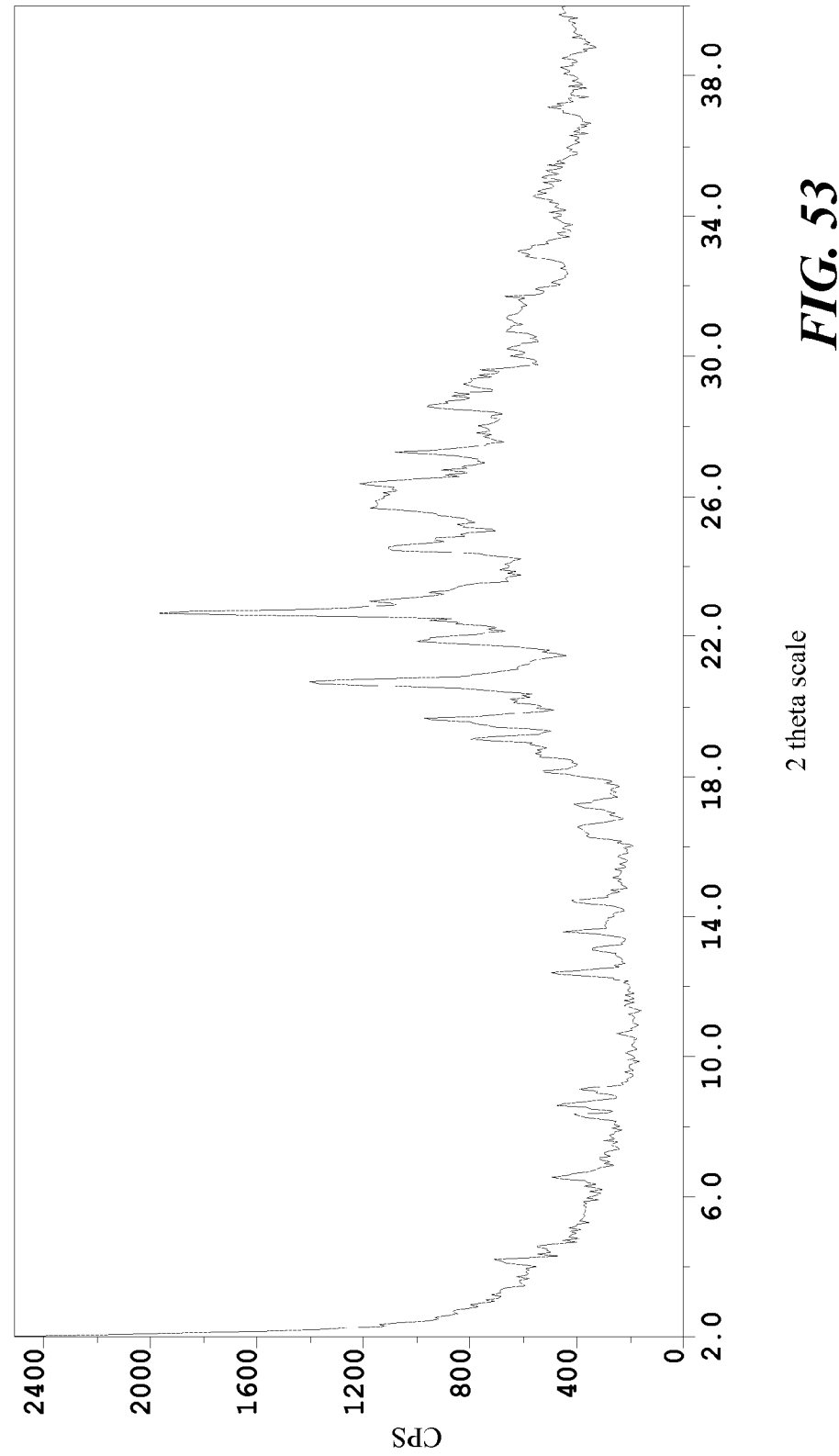
FIG. 53 shows an X-ray powder diffractogram of Nilotinib hydrobromide crystalline form III.

The present invention encompasses a crystalline form of Nilotinib HBr, designated as form III. Nilotinib HBr form III can be characterized by data selected from: an X-ray powder diffraction pattern having peaks at 6.5, 8.5, 12.3, 19.5 and 20.6 degrees two theta±0.2 degrees two theta; an X-ray powder diffraction pattern substantially as depicted in FIG. 53; and combinations thereof. The Nilotinib HBr form III may be further characterized by an X-ray powder diffraction pattern having one, two, three, four or five peaks selected from 14.3, 18.9, 21.7, 22.6 and 24.4 degrees two theta±0.2 degrees two theta.

Figure 54:
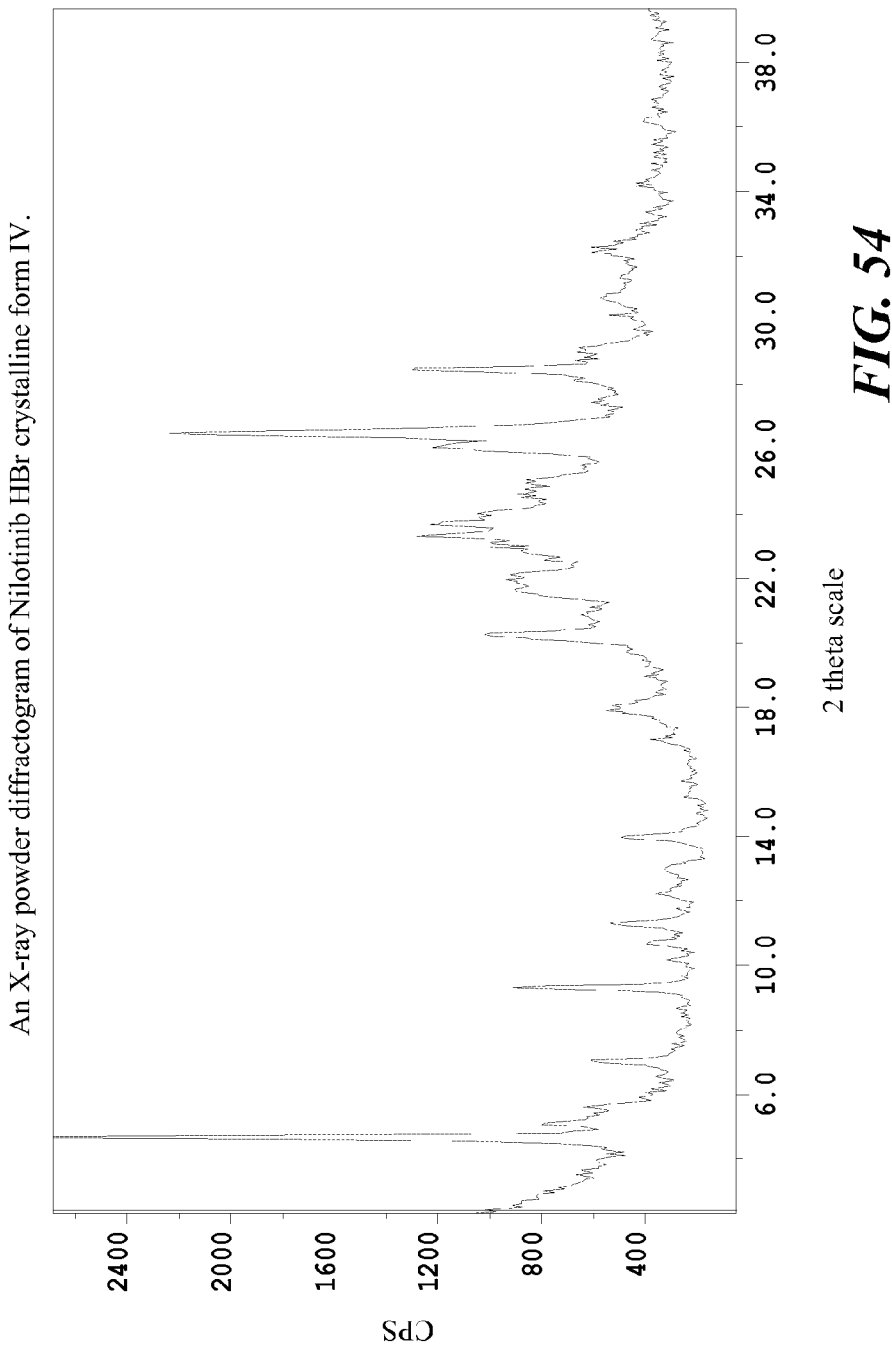
FIG. 54 shows an X-ray powder diffractogram of Nilotinib hydrobromide crystalline form IV.

The present invention encompasses a crystalline form of Nilotinib HBr, designated as form IV. Nilotinib HBr form IV can be characterized by data selected from: an X-ray powder diffraction pattern having peaks at 4.7, 9.3, 11.3, 14.0 and 20.2 degrees two theta±0.2 degrees two theta; an X-ray powder diffraction pattern substantially as depicted in FIG. 54; and combinations thereof. The Nilotinib HBr form IV may be further characterized by an X-ray powder diffraction pattern having one, two, three, four or five peaks selected from 5.1, 7.0, 10.7, 23.3 and 26.5 degrees two theta±0.2 degrees two theta.

Figure 55:
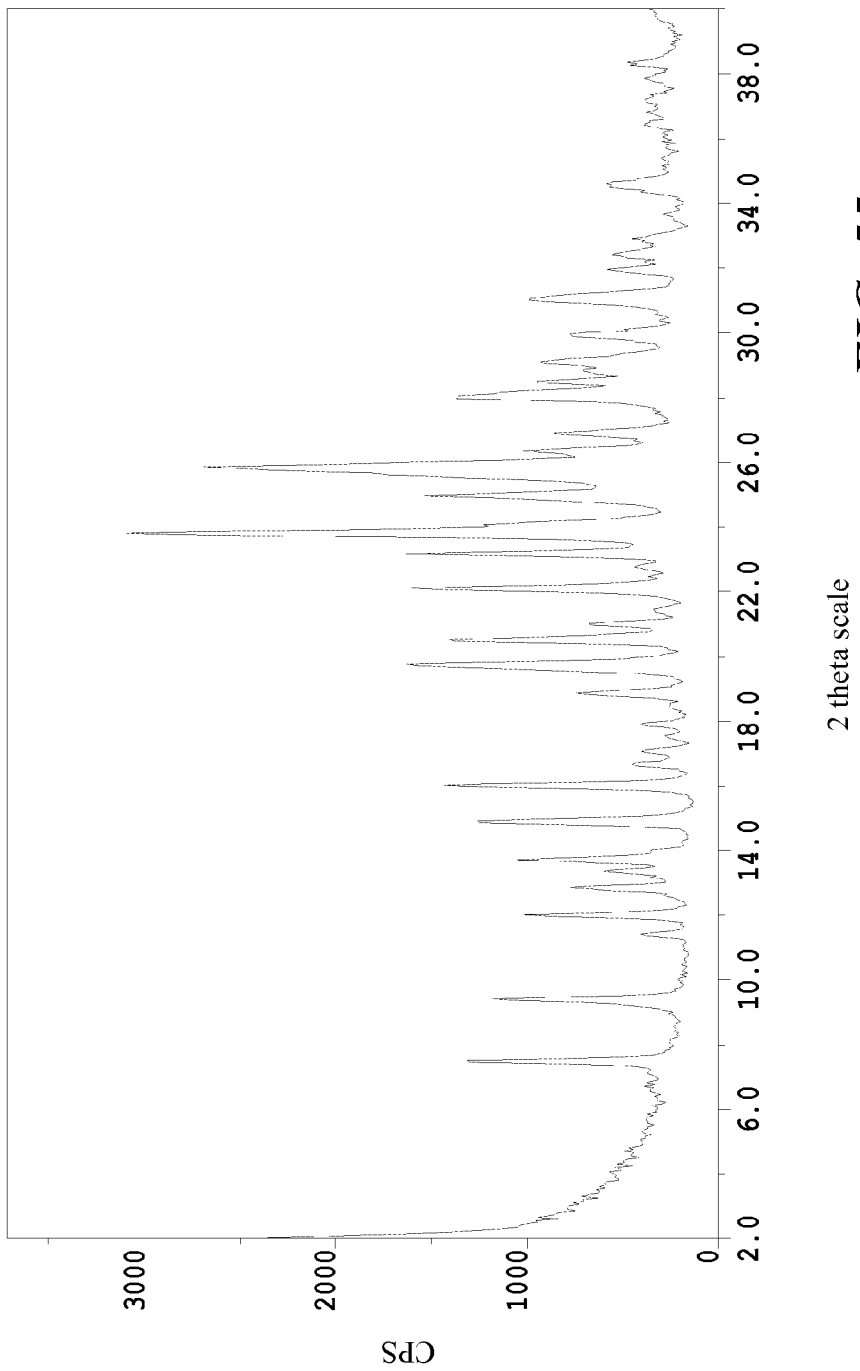
FIG. 55 shows an X-ray powder diffractogram of Nilotinib hydrobromide crystalline form V.

The present invention encompasses a crystalline form of Nilotinib HBr, designated as form V. Nilotinib HBr form V can be characterized by data selected from: an X-ray powder diffraction pattern having peaks at 7.4, 9.4, 12.0, 14.8 and 16.0 degrees two theta±0.2 degrees two theta; an X-ray powder diffraction pattern substantially as depicted in FIG. 55; and combinations thereof. The Nilotinib HBr form V may be further characterized by an X-ray powder diffraction pattern having one, two, three, four or five peaks selected from 12.8, 13.7, 19.7, 20.4 and 23.8 degrees two theta±0.2 degrees two theta.

Figure 56:
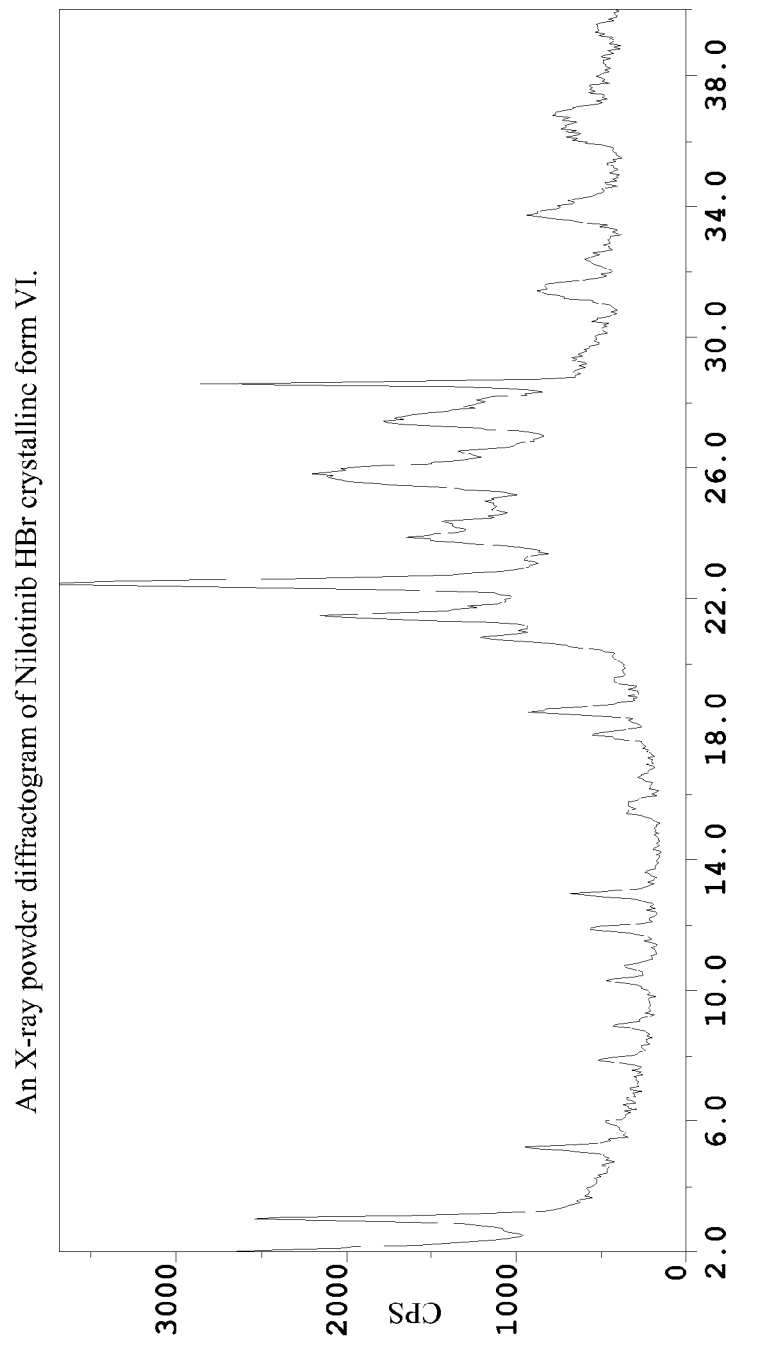
FIG. 56 shows an X-ray powder diffractogram of Nilotinib hydrobromide crystalline form VI.

The present invention encompasses a crystalline form of Nilotinib HBr, designated as form VI. Nilotinib HBr form VI can be characterized by data selected from: an X-ray powder diffraction pattern having peaks at 2.9, 11.8, 12.8, 18.4 and 22.3 degrees two theta±0.2 degrees two theta; an X-ray powder diffraction pattern substantially as depicted in FIG. 56; and combinations thereof. The Nilotinib HBr form VI may be further characterized by an X-ray powder diffraction pattern having one, two, three, four or five peaks selected from 5.1, 7.7, 17.7, 20.7 and 21.3 degrees two theta±0.2 degrees two theta.

Figure 58:
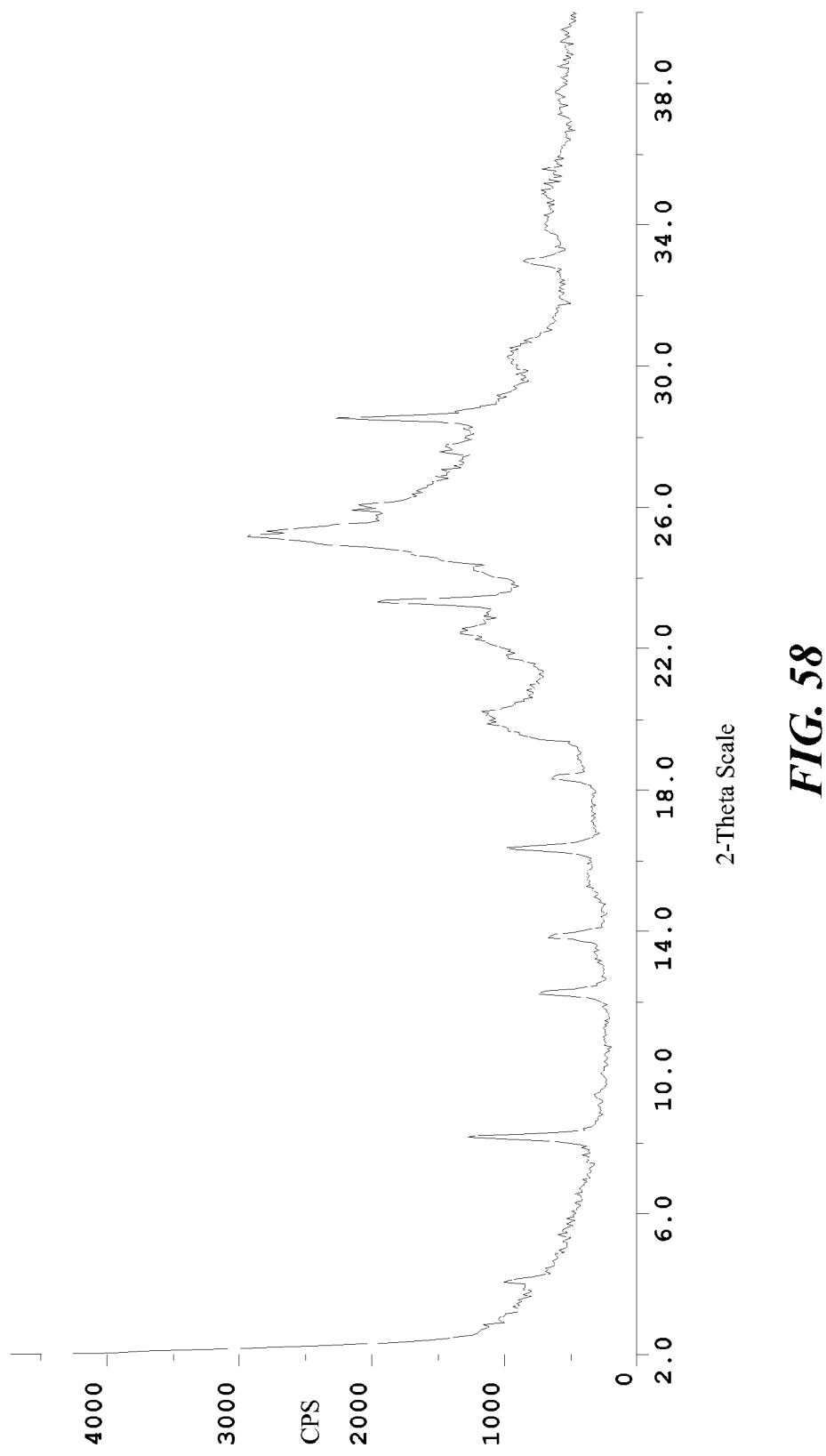
FIG. 58 shows an X-ray powder diffractogram of Nilotinib hydrobromide crystalline form VII.

The present invention encompasses a crystalline form of Nilotinib HBr, designated as form VII. Nilotinib HBr form VII can be characterized by data selected from: an X-ray powder diffraction pattern having peaks at 8.1, 12.2, 13.8, 16.3 and 23.3 degrees two theta±0.2 degrees two theta; an X-ray powder diffraction pattern substantially as depicted in FIG. 58; and combinations thereof. The Nilotinib HBr form VII may be further characterized by an X-ray powder diffraction pattern having one, two, three, four or five peaks selected from 4.0, 18.3, 25.1 and 26.0 degrees two theta±0.2 degrees two theta.

Figure 64:
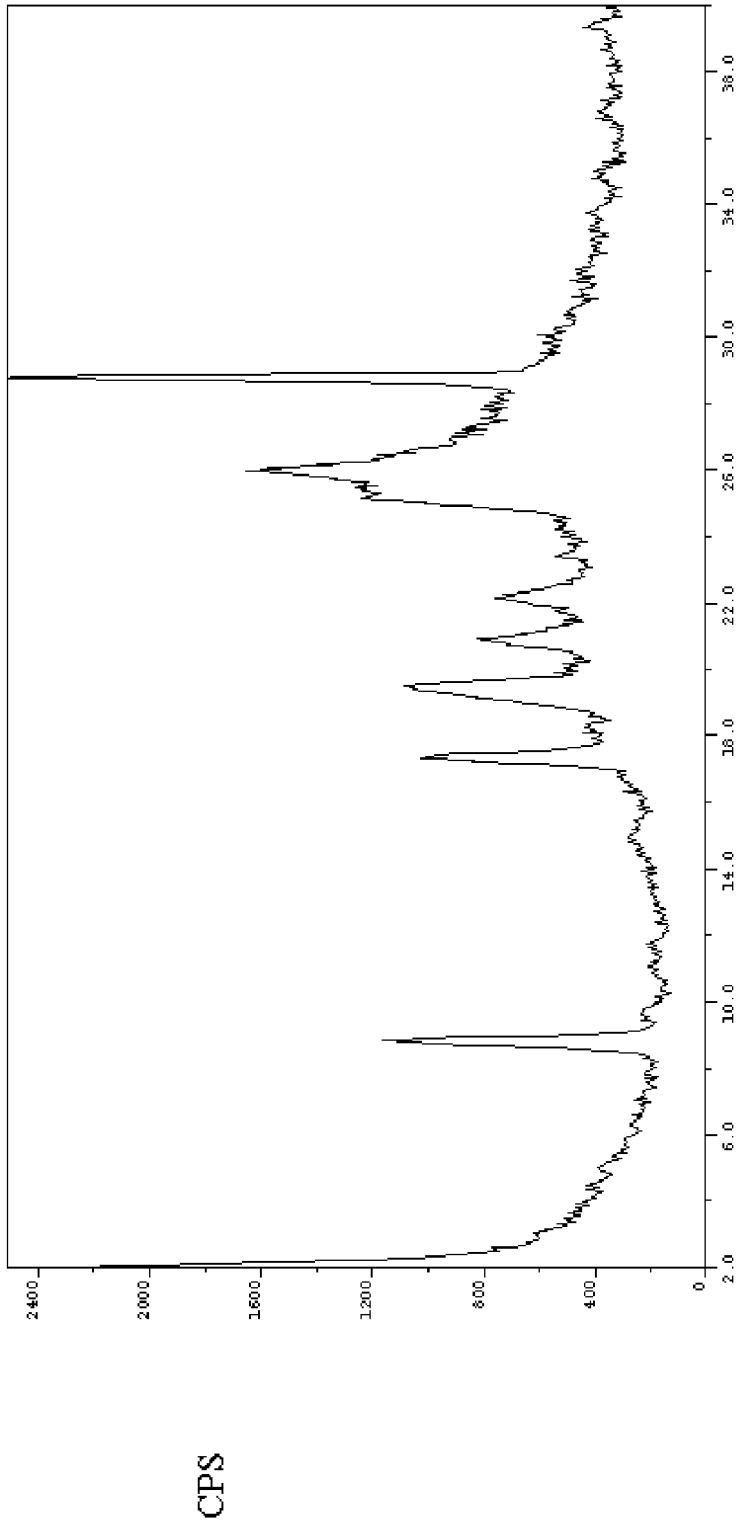
FIG. 64 shows an X-ray powder diffractogram of Nilotinib hydrobromide crystalline form VIII.

The present invention encompasses a crystalline form of Nilotinib HBr, designated as form VIII. Nilotinib HBr form VIII can be characterized by data selected from: an X-ray powder diffraction pattern having peaks at 8.5, 17.0, 19.2, 20.6 and 21.8 degrees two theta±0.2 degrees two theta; an X-ray powder diffraction pattern substantially as depicted in FIG. 64; and combinations thereof. The Nilotinib HBr form VIII may be further characterized by an X-ray powder diffraction pattern having an additional broad peak at 25.6 degrees two theta±0.2 degrees two theta.

Figure 65:
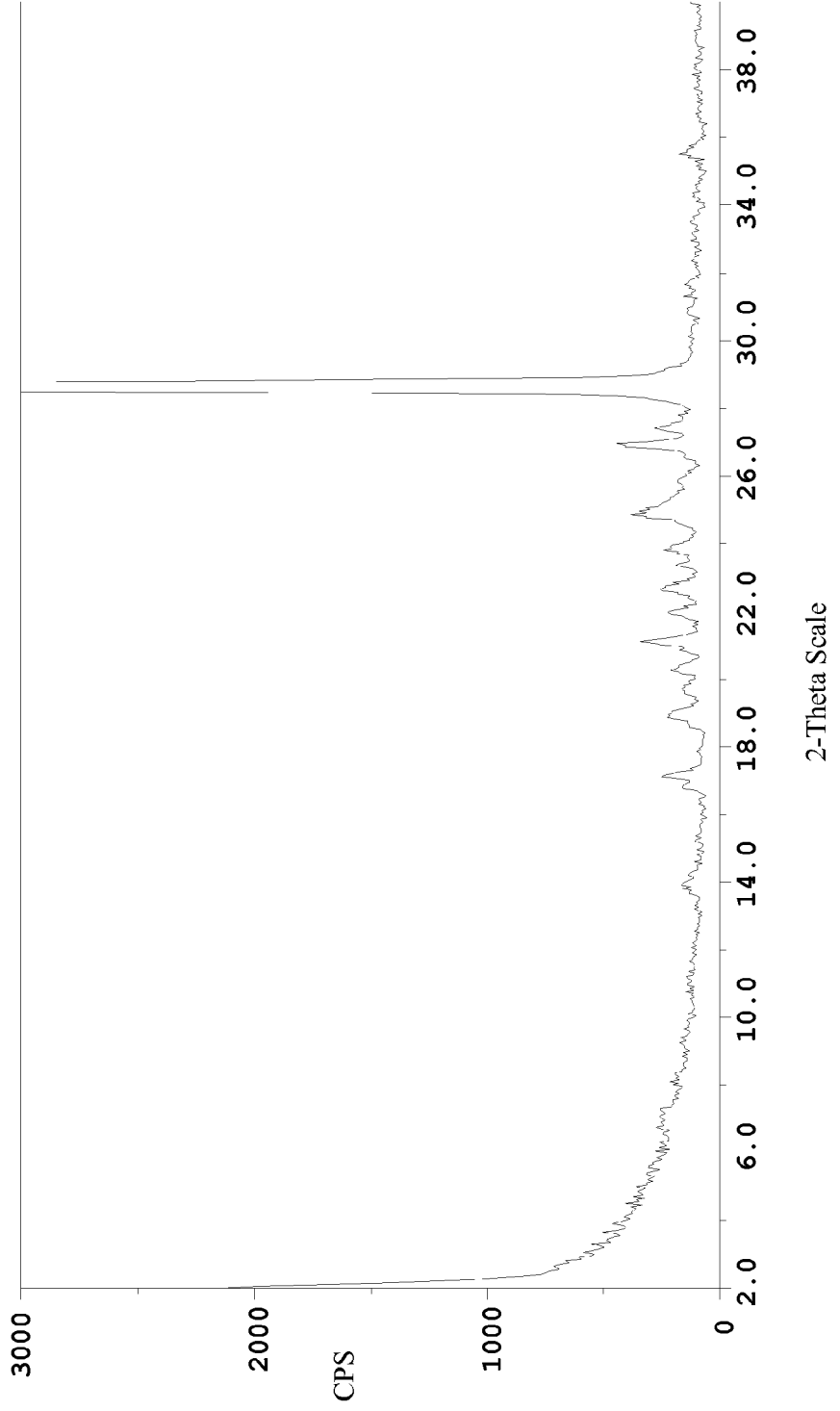
FIG. 65 shows an X-ray powder diffractogram of Nilotinib hydrobromide crystalline form IX.

The present invention encompasses a crystalline form of Nilotinib HBr, designated as form IX. Nilotinib HBr form IX can be characterized by data selected from: an X-ray powder diffraction pattern having peaks at 16.9, 18.7, 20.9, 21.8 and 26.7 degrees two theta±0.2 degrees two theta; an X-ray powder diffraction pattern substantially as depicted in FIG. 65; and combinations thereof. The Nilotinib HBr form IX may be further characterized by an X-ray powder diffraction pattern one, two, three, four or five peaks selected from 13.7, 16.6, 20.1, 22.5 and a broad peak having a maximum at 24.7 degrees two theta±0.2 degrees two theta.

Figure 66:
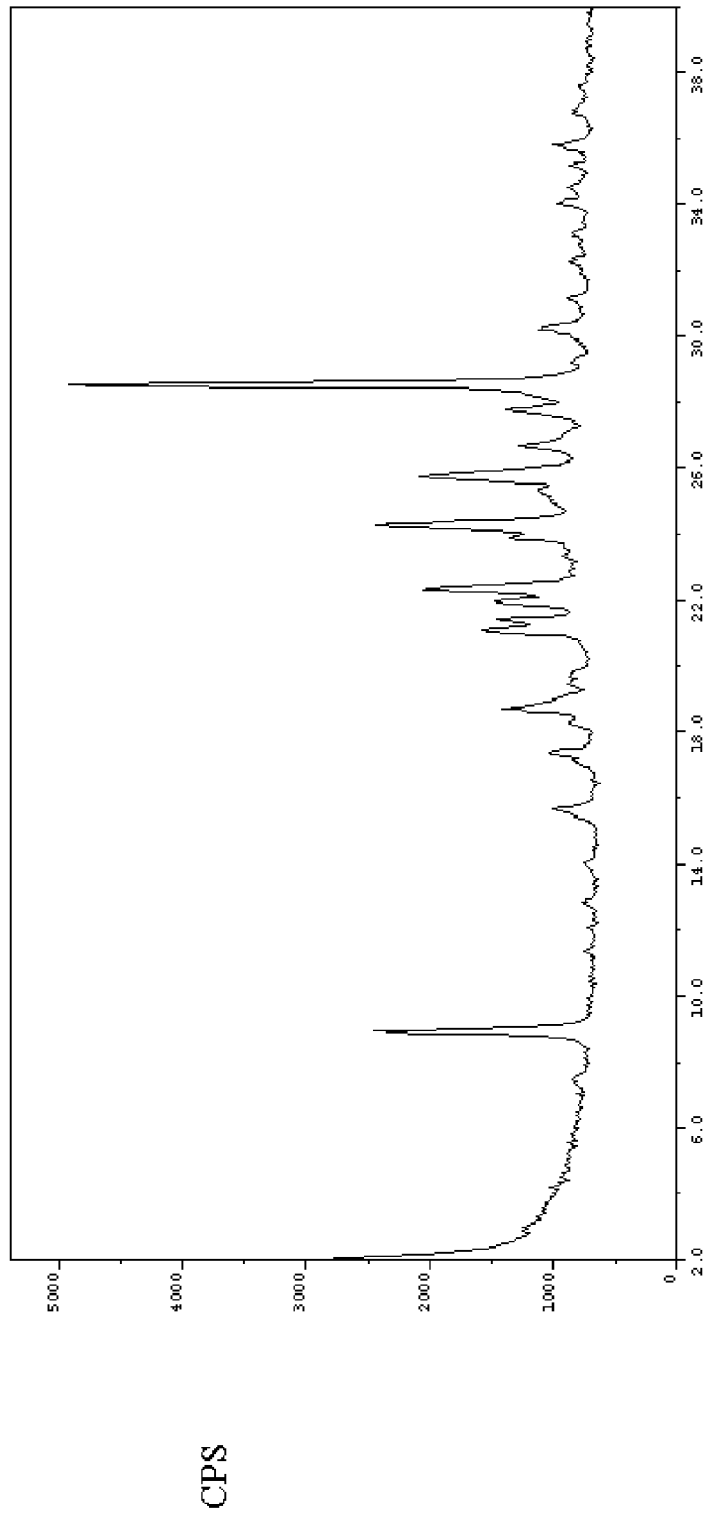
FIG. 66 shows an X-ray powder diffractogram of Nilotinib hydrobromide crystalline form X.

The present invention encompasses a crystalline form of Nilotinib HBr, designated as form X. Nilotinib HBr form X can be characterized by data selected from: an X-ray powder diffraction pattern having peaks at 8.8, 15.5, 18.6, 22.2 and 24.2 degrees two theta±0.2 degrees two theta; an X-ray powder diffraction pattern substantially as depicted in FIG. 66; and combinations thereof. The Nilotinib HBr form X may be further characterized by an X-ray powder diffraction pattern having one, two, three, four or five peaks selected from 17.3, 21.0, 21.3, 21.8 and 25.7 degrees two theta±0.2 degrees two theta.

Figure 67:
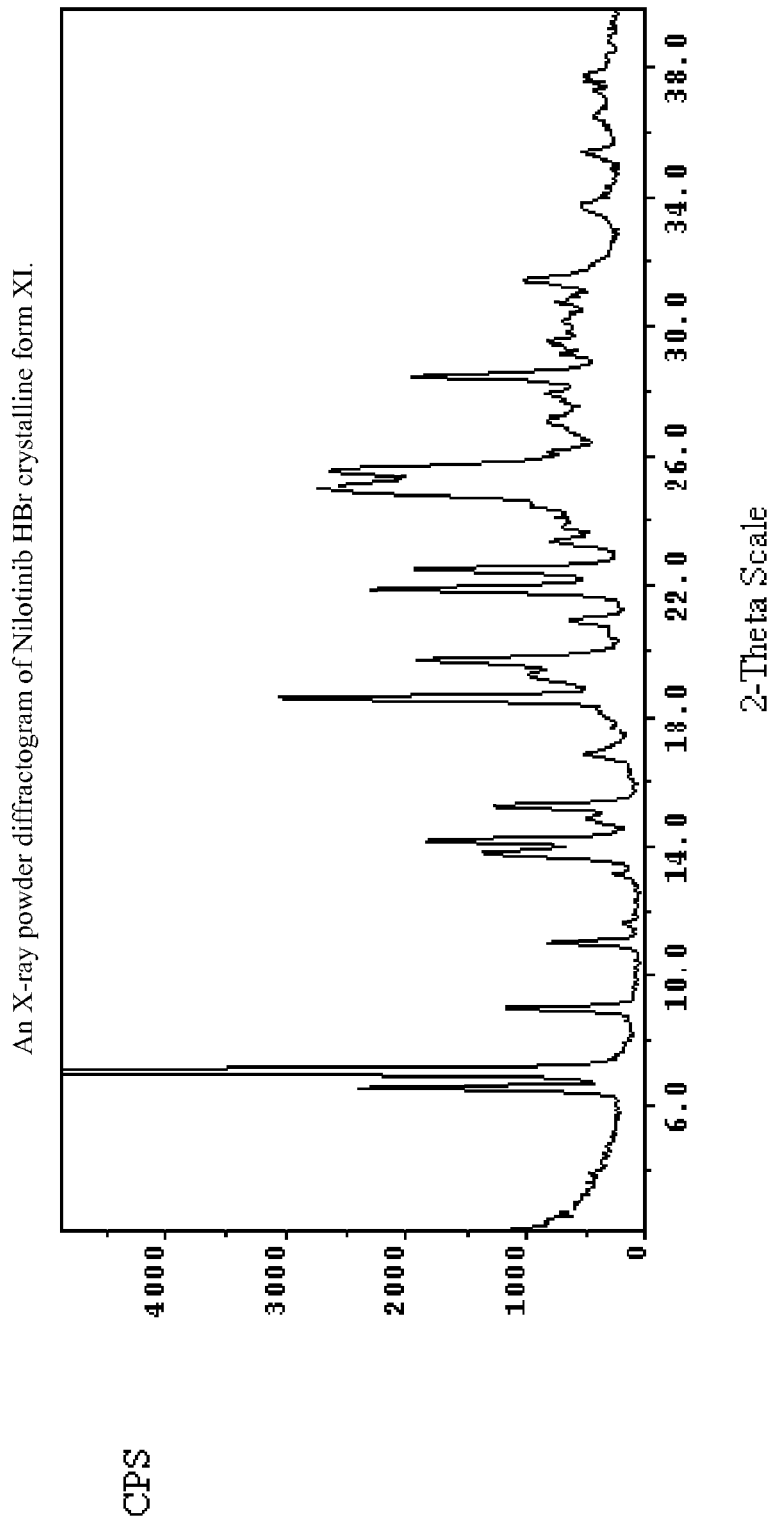
FIG. 67 shows an X-ray powder diffractogram of Nilotinib hydrobromide crystalline form XI.

The present invention encompasses a crystalline form of Nilotinib HBr, designated as form XI. Nilotinib HBr form XI can be characterized by data selected from: an X-ray powder diffraction pattern having peaks at 7.1, 14.1, 18.6, 21.9 and 22.5 degrees two theta±0.2 degrees two theta; an X-ray powder diffraction pattern substantially as depicted in FIG. 67; a solid state $^{13}$C NMR spectrum having signals at 129.8, 132.3 and 160.5±0.2 ppm; a solid-state $^{13}$C NMR spectrum having chemical shift differences between the signal exhibiting the lowest chemical shift in the chemical shift range of 100 to 180 ppm and another in the chemical shift range of 100 to 180 ppm of 23.0, 25.5 and 53.7±0.1 ppm; a solid state $^{13}$C NMR spectrum as depicted in any one of FIGS. 73-74; and combinations thereof. Typically, the signal exhibiting the lowest chemical shift in the chemical shift in the range of 100 to 180 ppm is typically at about 106.8±1 ppm. The Nilotinib HBr form XI may be further characterized by an X-ray powder diffraction pattern having one, two, three, four or five peaks selected from 9.0, 11.1, 13.8, 15.2 and 19.7 degrees two theta±0.2 degrees two theta.

Alternatively Nilotinib HBr form XI can be characterized by a powder XRD pattern with peaks at 6.5, 7.1, 9.0, 11.1, 11.6, 13.1, 13.8, 14.1, 14.8, 15.2, 16.8, 18.6, 19.3, 19.7, 20.9, 21.9, 22.5, 23.2, 25.0, 25.6 degrees two theta±0.2 degrees two theta.

Typically, the Nilotinib HBr form XI can be of Nilotinib monohydro-bromide.

As discussed above, Nilotinib HBr form XI has advantageous properties. In particular, the crystalline Nilotinib HBr form XI of the present invention is polymorphically stable. For example when exposed to ethanol or methanol vapors, at a temperature of about RT for a time period of about 1 hour to about 24 hours form XI of Nilotinib HBr does not convert to other forms of Nilotinib HBr. This stability is an advantage for the production, storage and processing of pharmaceuticals comprising Nilotinib HBr.

Figure 59:
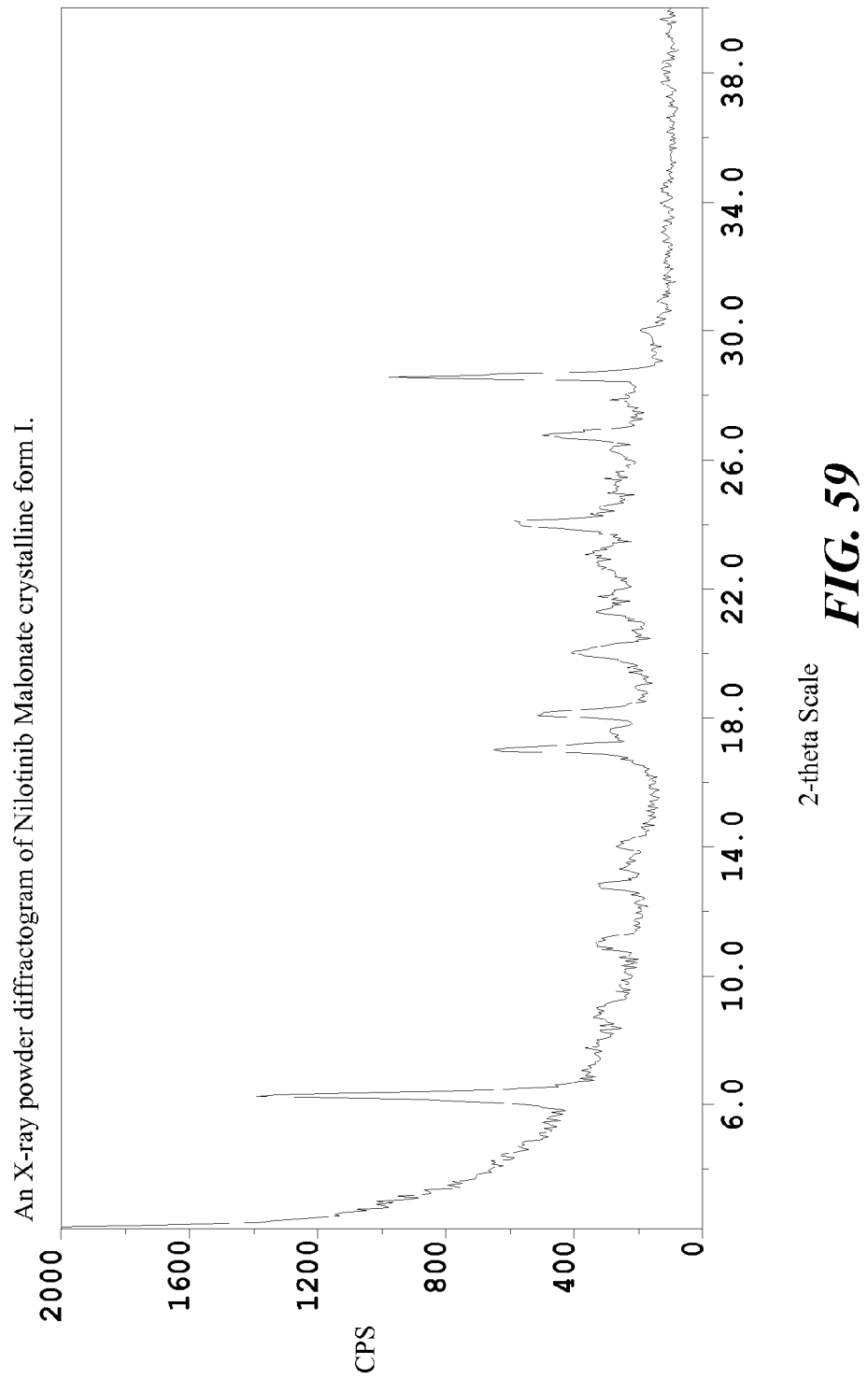
FIG. 59 shows an X-ray powder diffractogram of Nilotinib malonate crystalline form I.

The present invention encompasses a crystalline form of Nilotinib malonate, designated as form I. Nilotinib malonate form I can be characterized by data selected from: an X-ray powder diffraction pattern having peaks at 6.2, 16.9, 18.0, 19.9 and 24.0 degrees two theta±0.2 degrees two theta; an X-ray powder diffraction pattern substantially as depicted in FIG. 59; and combinations thereof. The Nilotinib malonate form I may be further characterized by an X-ray powder diffraction pattern having additional broad peaks having maxima at 11.0, 12.8, 14.0, 21.3, and 23.1 degrees two theta±0.3 degrees two theta.

Figure 63:
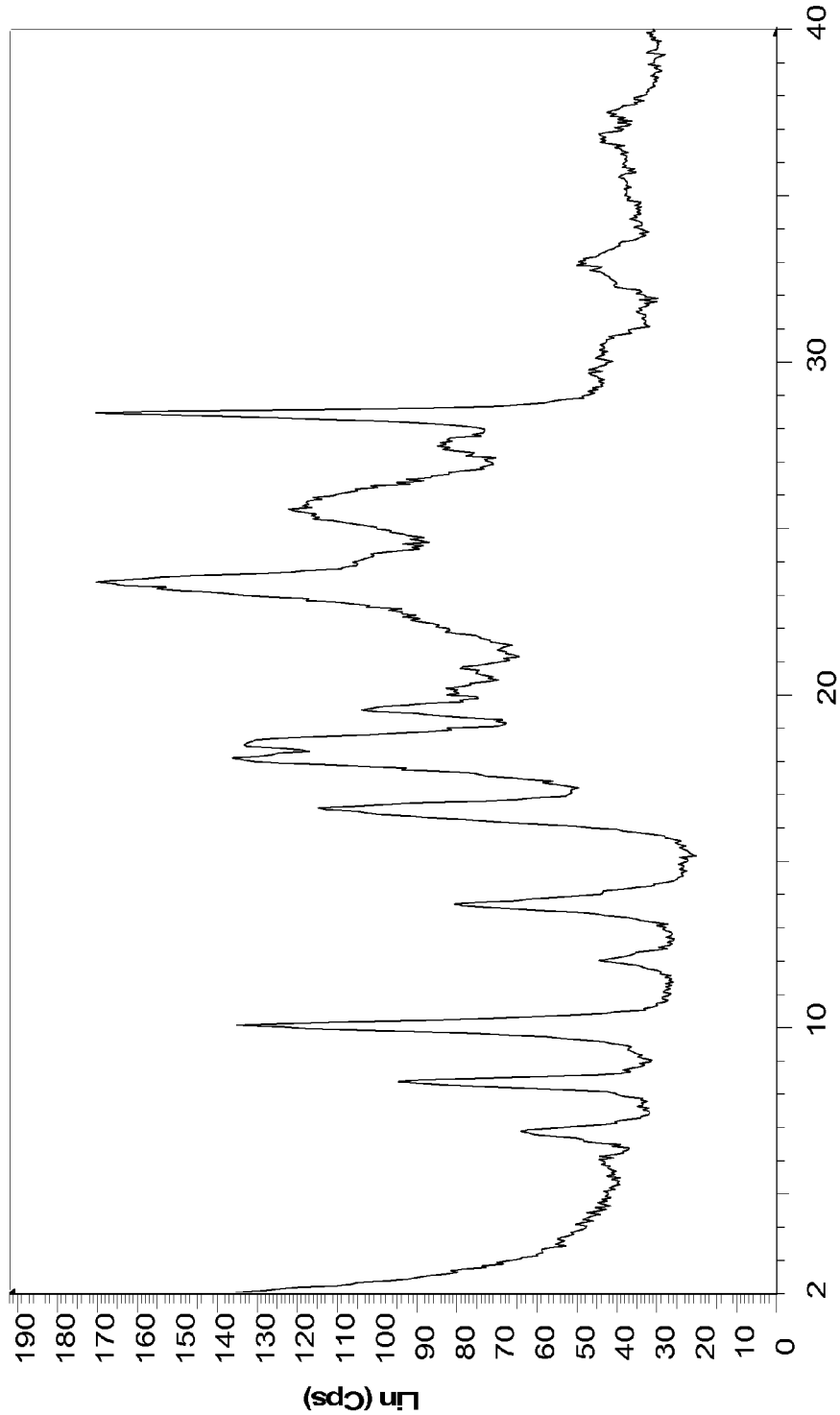
FIG. 63 shows an X-ray powder diffractogram of Nilotinib oxalate crystalline form I.

In one embodiment, the present invention encompasses a crystalline form of Nilotinib Oxalate, designated as form I. Nilotinib oxalate form I can be characterized by data selected from: an X-ray powder diffraction pattern having peaks at 8.3, 10.0, 13.6, 16.5 and 23.3 degrees two theta±0.2 degrees two theta; an X-ray powder diffraction pattern substantially as depicted in FIG. 63; and combinations thereof. The Nilotinib oxalate form I may be further characterized by an X-ray powder diffraction pattern having additional peaks at 6.8, 12.0, 18.1, 19.5 and a broad peak having a maximum at 25.6 degrees two theta±0.3 degrees two theta. Typically, the Nilotinib oxalate form I can be of Nilotinib dioxalate salt.

The above described Nilotinib salts and solid state forms can be used to prepare Nilotinib base or Nilotinib HCl, preferably Nilotinib monohydrochloride salt, and hydrates thereof, particularly Nilotinib monohydrochloride monohydrate, and pharmaceutical formulations thereof.

The present invention encompasses a process for preparing Nilotinib HCl comprising preparing any one of the above salts and solid state forms of Nilotinib by the processes of the present invention and converting it to Nilotinib HCl preferably Nilotinib monohydrochloride salt, and hydrates thereof, particularly Nilotinib monohydrochloride monohydrate. The conversion may be done for example, by basifying the Nilotinib salt to obtain Nilotinib base and further reacting the formed Nilotinib base with HCl.

The present invention also encompasses a process for preparing Nilotinib base comprising preparing any one of the above salts and solid state forms of Nilotinib by the processes of the present invention and converting it to Nilotinib base. The conversion may be done for example, by basifying the Nilotinib salt to obtain the Nilotinib base.

Also, the above Nilotinib salts and solid state forms can be used in the preparation of a pharmaceutical composition. The present invention encompasses a pharmaceutical composition comprising any one of the forms of Nilotinib salts of the invention as described above and at least one pharmaceutically acceptable excipient. Preferably, the Nilotinib salt is Nilotinib L-tartrate (particularly Nilotinib L-tartrate form IV), or Nilotinib hydrobromide (particularly Nilotinib hydrobromide Form XI).

The present invention provides the use of any of any one of the above crystalline or amorphous forms or any of the above pharmaceutical compositions for the treatment of drug-resistant chronic myelogenous leukemia (CML). The present invention also provides a method of treating drug-resistant CML, comprising administering a therapeutically effective amount of at least one of the above crystal or amorphous forms or at least one of the above pharmaceutical compositions to a person suffering from CML. In another embodiment, the invention provides the Nilotinib salt described in any of the above embodiments, for use as a medicament, preferably wherein the medicament is for the treatment of CML. Preferably, the Nilotinib salt is selected from: Nilotinib L-tartrate (particularly Nilotinib L-tartrate form IV), Nilotinib HBr (particularly Nilotinib HBr Form XI), Nilotinib succinate, Nilotinib glutamate, Nilotinib acetate and Nilotinib L-malate, more preferably, the Nilotinib salt is Nilotinib L-tartrate or Nilotinib HBr.

Having thus described the invention with reference to particular preferred embodiments and illustrative examples, those in the art can appreciate modifications to the invention as described and illustrated that do not depart from the spirit and scope of the invention as disclosed in the specification. The Examples are set forth to aid in understanding the invention but are not intended to, and should not be construed to limit its scope in any way.

X-Ray Powder Diffraction Method:

The X-ray powder diffraction of the Nilotinib salts were performed on one of two different X-ray diffractometers. One instrument was an ARL X-ray powder diffractometer model X'TRA-019, with a Peltier detector. Copper $K\alpha_1$ radiation ($\lambda$=1.5418 Å) was used. The sample holder was a round standard aluminum sample holder with round zero background quartz plate. The scanning parameters were: range: 2-40 degrees two-theta; scan mode: continuous scan; and scan rate: 3 degrees/minute. The other instrument was a Bruker X-Ray powder diffractometer model D8 advance equipped with lynxEye. $\lambda$=1.5418 Å. The scanning parameters were: range: 2-40 degrees two theta, step size: 0.05 degrees two theta, time per step: 0.5 sec.

FIGS. 7, 8, 10, 13, 14, 17, 18, 21, 24-28, 42 and 63 were obtained from measurements performed on an ARL X-ray powder diffractometer model X'TRA-019.

FIGS. 1-6, 9, 11, 12, 15, 16, 19, 20, 22, 23, 29-41, 43-62 and 64-70 were obtained from measurements performed on a Bruker X-Ray powder diffractometer model D8 advance.

The peak positions for all samples, except for Nilotinib hydrochloride form T20 and Nilotinib hydrobromide form I, were determined by using silicon powder as an internal standard in an admixture with the sample measured. The position of the silicon (111) peak was corrected to be 28.45 degrees two theta. The positions of the peaks were corrected respectively, but no corrections were performed on the diffractograms provided herein in the figures).

X-Ray Powder Diffraction Method—Nilotinib Acetate Form VI:

XRPD analysis of Acetate Form VI was performed on a Bruker X-Ray powder diffractometer model D8 advance equipped with lynxEye. $\lambda$=1.5418 Å. Scanning parameters: Range: 2-40 deg., step size: 0.05 deg, time per step: 0.5 sec, divergence slit: 1 deg. The peak positions were determined by using silicon powder as an internal standard in an admixture with the sample measured. The position of the silicon (111) peak was corrected to be 28.45 degrees two theta. The positions of the peaks were corrected respectively, but no corrections were performed on the diffractograms provided herein in the figures).

FT-IR Instrumentation and Method:

FT-IR spectroscopy Perkin Elmer Spectrum One FT-IR Spectrometer S/N 58001.

Scanning parameters: Nujol mode was used for all samples; the spectra were scanned between: 4000-400 cm$^{-1}$. All the spectra were measured in 16 scans in resolution of 4.0 cm$^{-1}$.

Solid State $^{13}$C NMR Instrumentation and Method:

Solid-state $^{13}$C NMR spectra were recorded with variable amplitude cross polarization, magic angle spinning and high power proton decoupling using a BRUKER Advance II+500 spectrometer operating at 125 MHz and at ambient temperature (about 25° C.—not controlled). A probe using 4 mm o.d. zirconia rotors was employed. The operation conditions were: contact time of 2 ms; recycle delay of 5 s; 1024 scans, and spin rate of 11 KHz. Chemical shifts were referenced via a replacement sample of glycine (carboxyl carbon chemical shift assigned as 176.03 ppm relative to the signal of tetramethylsilane). Homogeneity of the magnetic field was checked using adamantine. Magic angle was set using KBr.

REFERENCE EXAMPLES

Nilotinib HCl form A as used in any of the processes described in the present application may be prepared according to WO '870 (e.g., examples 2 and 4), which is incorporated herein by reference.

Nilotinib HCl form T18 as used in any of the processes described in the present application may be prepared according to WO 2010/054056, examples 33-38, which is incorporated herein by reference. For example: To a 1 Liter reactor was added Nilotinib-base form A (20 g, 0.04 mol), absolute ethanol (188 ml) and 13.77% HCl solution in ethanol abs. (10 g, 0.04 mol). The slurry formed thereby was heated to reflux, and dissolution occurred during the stirring. The solution was then filtered under reduced pressure. The filtrate was fed back to the reactor and heated back to reflux. At 76.6° C. the solution was seeded with 0.2 g of dry material obtained by the process of example 23. Precipitation was observed. Then, the solution was maintained at reflux for 1 h, followed by cooling over 2 h to 6° C. At 6° C. ethanol abs. was added (300 ml) and the slurry was stirred at 5° C. for 30 minutes, filtered, washed with ethanol abs. to yield Nilotinib-HCl, form T18.

Nilotinib base form A as used in any of the processes described in the present application may be prepared according to U.S. Pat. No. 7,169,791, Example 92, which is incorporated herein by reference.

Nilotinib HCl Form T17 seed crystals can be made by a process as disclosed in WO 2010/054056, such as by examples 23-28 or Examples 31-33, and preferably Example 25:

To a 1 Liter reactor was added Nilotinib-base form A (20 g, 0.04 mol), absolute ethanol (200 ml), and HCl 32% solution in water (6.45 g, 0.04 mol). A slurry was formed. The slurry was heated to reflux, dissolution occurred during the stirring, and the solution was then filtered under reduced pressure. The filtrate was fed to a second reactor and heated back to reflux. At 76.0° C. the solution was seeded with 0.2 g of a dry material obtained by the process of example 23. Precipitation was observed. Then, the mixture was maintained at reflux for 0.5 h, followed by cooling over 2 h to 5° C. During cooling at 20° C. absolute ethanol was added (100 ml) and the slurry was stirred till it cooled to 5° C. The cooled slurry was then filtered, and the collected solid was washed with absolute ethanol, and dried over night at 70° C. in a vacuum oven to yield Nilotinib-HCl form T17 (16.3 g, 73% yield).

EXAMPLES

The starting material Nilotinib base can be prepared by the following procedure:

Preparation of Nilotinib Base

To a 1 liter reactor was fed 40 g of 4-methyl-3-(4-(pyridine-3-yl)pyrimidin-2-ylamino)benzoic acid (0.13 mol), 200 ml of N-methylpyrrolidone (NMP) (5V) and 13 ml of thionyl chloride (0.18 mol). The reactor was heated to 60° C. and maintained at 60° C. for 1.5 hr. After 1.5 hr of heating, 31.5 g of 3-(trifluoromethyl)-5-(4-methyl-1H-imidazol-1-yl)benzenamine (0.13 mol) was fed into the reactor. The reactor was then heated to 90° C., and maintained for 30 minutes at this temperature. Then 200 ml (5V) of water was added. The resulting mixture was maintained for 2 hours at 90° C. Then, an additional 240 ml (6V) of N-methylpyrrolidone was added, followed by 26.5 ml of sodium hydroxide (47% aqueous) to raise the pH to 6.5-7. The reactor was then cooled to 40° C. and maintained for 3 hours. The mixture was then filtered and the filter cake was washed with ethanol and water. The washed material was then dried in a vacuum tray oven overnight to provide dry Nilotinib base (62.1 g, Yield 90%)

Example 1

Preparation of Crystalline Nilotinib HCl Form T20

To a 2 Liter reactor was added Nilotinib-HCl form T18+A (20 g, 0.03 mol) and absolute ethanol (400 ml). The resulting slurry was stirred at 20-25° C. for 15 min. No dissolution occurred during the stirring. The slurry was then sampled under nitrogen atmosphere and filtered and the collected solid was dried at 45° C. to yield Nilotinib-HCl form T20.

Example 2

Preparation of Crystalline Nilotinib HCl Form T20

To a 2 Liter reactor was added Nilotinib-HCl form T18+A (20 g, 0.03 mol) and absolute ethanol (400 ml). The resulting slurry was stirred and heated to reflux. No dissolution occurred during the stirring/heating. The heated slurry was maintained at reflux for 21 h. A sample was taken from the edge of the reactor to yield Nilotinib-HCl form T20.

Example 3

Preparation of Crystalline Nilotinib HCl Form T20

To a 2 Liter reactor was added Nilotinib-HCl form T18+ form A (20 g, 0.03 mol) and absolute ethanol (400 ml). The resulting slurry was stirred at 20-25° C. for 15 min. No dissolution occurred during the stirring. The mixture was then sampled under nitrogen atmosphere and filtered to yield Nilotinib-HCl form T20.

Example 4

Preparation of Nilotinib HCl Form T19

To a 2 Liter reactor was added Nilotinib-HCl form A (20 g, 0.03 mol) and absolute ethanol (400 ml). The resulting slurry was stirred and heated to reflux. No dissolution occurred during the stirring/heating. The slurry was then maintained at reflux for 1 h, and sampled under nitrogen atmosphere and filtered to yield Nilotinib-HCl form T19.

Example 5

Preparation of Nilotinib Fumarate Form I

To a 50 ml flask was added Nilotinib base (0.5 g, 0.94 mmol) and 2,2,2-trifluoroethanol (TFE) (5 ml). A clear solution was obtained. Fumaric acid (0.11 g, 1.03 mmol) was added, and the reaction was stirred at 40° C. for 1 hour. Then it was cooled to room temperature (20-30° C.) and stirred for 2 days. The solvent was then evaporated. A thick yellow paste was obtained, which was dried in a vacuum oven at 60° C. for 2 days to give Nilotinib fumarate form I.

Example 6

Preparation of Nilotinib Fumarate Form II

Nilotinib base (0.300 g, 0.57 mmol) was dissolved in TFE (2 mL) at 40° C. The stirred mixture was added to a solution of fumaric acid (0.033 g, 0.28 mmol) in TFE (1 mL) at 40° C.

Stirring of the resulting clear solution was continued for about 4 h at 40° C. and the solution was subsequently cooled to 5° C. and kept at this temperature overnight to obtain a precipitate. The precipitate was filtered to give Nilotinib fumarate form II.

Example 7

Preparation of Nilotinib 2-Chloromandelate Form I

Nilotinib base (0.300 g, 0.57 mmol) was dissolved in TFE (2 mL) at 40° C. to obtain a mixture. The mixture was stirred and added to a solution of 2-chloromandelic acid (0.106 g, 0.57 mmol) in TFE (1 mL) at 40° C. Stirring of the resulting clear solution was continued for about 4 h at 40° C. and the solution was subsequently cooled to 5° C. The mixture was kept at 5° C. overnight and then methyl tert-butyl ether (MTBE) (1.5 v/v) was added to the mixture at room temperature, leading to precipitation. The precipitate was filtered to give a white solid of Nilotinib 2-chloromandelate form I.

Example 8

Preparation of Nilotinib 2-Chloromandelate Amorphous Form

Nilotinib base (0.300 g, 0.57 mmol) was dissolved in TFE (2 mL) at 40° C. to obtain a mixture. The mixture was stirred and added to a solution of 2-chloromandelic acid (0.106 g, 0.57 mmol) in TFE (1 mL) at 40° C. Stirring of the resulting solution was continued for about 1 h and it was subsequently cooled to 5° C. The mixture was kept at 5° C. overnight and then a sample (1 ml) was taken from the mixture and evaporated to dryness under reduced pressure at 40° C. to give amorphous Nilotinib 2-chloromandelate.

Example 9

Preparation of Nilotinib Succinate Form I

Nilotinib base (0.300 g, 0.57 mmol) was dissolved in TFE (2 mL) at 40° C. to obtain a mixture. The mixture was stirred and added to a solution of succinic acid (0.033 g, 0.28 mmol) in TFE (1 mL) at 40° C. The resulting clear solution was stirred for about 4 h at 40° C. and the solution was subsequently cooled to 5° C. The mixture was kept at 5° C. overnight and then MTBE (1.5 v/v) was added to the mixture at room temperature leading to precipitation. The precipitate was filtered and the filter cake was dried at 40° C. in a vacuum oven overnight to give Nilotinib succinate form I.

Example 10

Preparation of Nilotinib Succinate Form II

Nilotinib base (0.300 g, 0.57 mmol) was dissolved in TFE (2 mL) at 40° C. to obtain a mixture. The mixture was stirred and added to a solution of succinic acid (0.066 g, 0.57 mmol) in TFE (1 mL) at 40° C. The resulting solution was stirred for about 4 h and subsequently cooled to 5° C. The mixture was kept at 5° C. overnight and then a sample (1 mL) was taken from the mixture and evaporated to dryness under reduced pressure at 40° C. to give Nilotinib succinate form II.

Example 11

Preparation of Nilotinib Succinate Form III

Nilotinib base (0.5 g, 0.94 mmol) and succinic acid (0.144 g, 0.94 mmol) were mixed with NMP (1.5 mL, 3.0V). The mixture was stirred and heated to 80° C. to dissolution. The stirring was continued at the same temperature for 5 h, after which the mixture was allowed to cool to room temperature resulting in precipitation. The precipitate was separated by filtration to give Nilotinib succinate form III. The filter cake was then washed with EtOH (27 mL, 95%) and dried in a vacuum oven (30 mbar) at 40° C. for 16 h to give Nilotinib succinate form III (0.17 g) as an off-white solid.

Example 12

Preparation of Nilotinib Adipate Form I

Nilotinib base (0.300 g, 0.57 mmol) was dissolved in TFE (2 mL) at 40° C. to obtain a mixture. The mixture was stirred and added to a solution of adipic acid (0.041 g, 0.28 mmol) in TFE (1 mL) at 40° C. The resulting clear solution was stirred for about 4 h at 40° C. and the solution was subsequently cooled to 5° C. The mixture was kept at 5° C. overnight and then MTBE (1.5 v/v) was added to the mixture at room temperature leading to precipitation. The precipitate was filtered and the filter cake was dried at 40° C. in a vacuum oven overnight to give a white solid of Nilotinib adipate form I.

Example 13

Preparation of Nilotinib L-Tartrate Form I

Nilotinib base (0.300 g, 0.57 mmol) was dissolved in TFE (2 mL) at 40° C. The stirred mixture was added to a solution of L-tartaric acid (0.043 g, 0.28 mmol) in TFE (1 mL) at 40° C. The resulting clear solution was stirred for about 4 h at 40° C. and the solution was subsequently cooled to 5° C. and kept at this temperature overnight to obtain a precipitate. The precipitate was filtered and the filter cake was dried at 40° C. in a vacuum oven overnight to give a white solid of Nilotinib L-tartrate form I.

Example 14

Preparation of Nilotinib L-Tartrate Form II

Nilotinib base (0.300 g, 0.57 mmol) was dissolved in TFE (2 mL) at 40° C. The stirred mixture was added to a solution of L-tartaric acid (0.083 g, 0.57 mmol) in TFE (1 mL) at 40° C. The resulting clear solution was stirred for about 4 h at 40° C. and subsequently cooled to 5° C. and kept at this temperature overnight leading to precipitation. The precipitate was filtered and the filter cake was dried at 40° C. in a vacuum oven overnight to give to give Nilotinib L-tartrate form II.

Example 15

Preparation of Nilotinib L-Tartrate Form III

About 10 mg of Nilotinib L-tartrate Form II was heated by TGA instrument to 90° C. (Heat rate 10 deg/min, 40 ml/min under $N_2$). The temperature was kept at 90° C. for 10 min, and then the sample was analyzed by XRD.

Example 16

Preparation of Nilotinib Glutarate Form I

Nilotinib base (0.300 g, 0.57 mmol) was dissolved in TFE (2 mL) at 40° C. to obtain a mixture. The mixture was stirred and added to a solution of glutaric acid (0.037 g, 0.28 mmol)

in TFE (1 mL) at 40° C. The resulting clear solution was stirred for about 4 h at 40° C. The solution was subsequently cooled to 5° C. The mixture was kept at 5° C. overnight and then MTBE (1.5 v/v) was added to the mixture at room temperature leading to precipitation. The precipitate was filtered to give Nilotinib glutarate form I.

Example 17

Preparation of Nilotinib Glutarate Form II

Nilotinib base (0.300 g, 0.57 mmol) was dissolved in TFE (2 mL) at 40° C. to obtain a mixture. The mixture was stirred and added to a solution of glutaric acid (0.037 g, 0.28 mmol) in TFE (1 mL) at 40° C. The resulting clear solution was stirred for about 4 h at 40° C. and the solution was subsequently cooled to 5° C. The mixture was kept at 5° C. overnight and then MTBE (1.5 v/v) was added to the mixture at room temperature leading to precipitation. The precipitate was filtered and the filter cake was dried at 40° C. in a vacuum oven overnight to give Nilotinib glutarate form II.

Example 18

Preparation of Nilotinib Glutarate Form III

Nilotinib base (0.300 g, 0.57 mmol) was dissolved in TFE (2 mL) at 40° C. to obtain a mixture. The mixture was stirred and added to a solution of glutaric acid (0.15 g, 1.14 mmol) in TFE (1 mL) at 40° C. The resulting clear solution was stirred for about 4 h at 40° C. and subsequently cooled to 5° C. and kept at this temperature overnight leading to precipitation. The precipitate was filtered and the filter cake was dried at 60° C. in a vacuum oven over 2 days to give Nilotinib glutarate form III.

Example 19

Preparation of Nilotinib p-Toluenesulfonate Form I

Nilotinib base (0.300 g, 0.57 mmol) was dissolved in TFE (2 mL) at 40° C. to obtain a mixture. The mixture was stirred and added to a solution of p-toluenesulfonic acid (0.108 g, 0.57 mmol) in TFE (1 mL) at 40° C. The resulting solution was stirred for about 4 h and it was subsequently cooled to 5° C. The mixture was kept at 5° C. overnight and then a sample (1 ml) was taken from the mixture and evaporated to dryness under reduced pressure at 40° C. to provide Nilotinib p-toluenesulfonate form I as a white solid.

Example 20

Preparation of Nilotinib p-Toluenesulfonate Form II

Nilotinib base (0.300 g, 0.57 mmol) was dissolved in TFE (2 mL) at 40° C. to obtain a mixture. The mixture was stirred and added to a solution of p-toluenesulfonic acid (0.108 g, 0.57 mmol) in TFE (1 mL) at 40° C. The resulting clear solution was stirred for about 4 h at 40° C. and subsequently cooled to 5° C. The mixture was kept at 5° C. overnight and then MTBE (1.5 v/v) was added to the mixture at room temperature leading to precipitation. The precipitate was filtered to provide Nilotinib p-toluenesulfonate form II as a white solid.

Example 21

Preparation of Nilotinib Camphorsulfonate Form I

Nilotinib base (0.300 g, 0.57 mmol) was dissolved in TFE (2 mL) at 40° C. to obtain a mixture. The mixture was stirred and added to a solution of (S)-camphor-sulfonic acid (0.132 g, 0.57 mmol) in TFE (1 mL) at 40° C. The resulting clear solution was stirred for about 4 h at 40° C. and it was subsequently cooled to 5° C. The mixture was kept at 5° C. overnight and then MTBE (1.5 v/v) was added to the mixture at room temperature leading to precipitation. The precipitate was filtered and the filter cake was dried at 40° C. in a vacuum oven overnight to give Nilotinib camphorsulfonate form I.

Example 22

Preparation of Nilotinib Camphorsulfonate Amorphous Form

Nilotinib base (0.300 g, 0.57 mmol) was dissolved in TFE (2 mL) at 40° C. to obtain a mixture. The mixture was stirred and added to a solution of (S)-camphor-sulfonic acid (0.132 g, 0.57 mmol) in TFE (1 mL) at 40° C. The resulting solution was stirred for about 2 h and it was subsequently cooled to 5° C. No precipitation was observed upon cooling. The mixture was kept at 5° C. overnight while stirring and then a sample (1 ml) was taken from the mixture and evaporated to dryness under reduced pressure at 40° C. to give amorphous Nilotinib camphorsulfonate.

Example 23

Preparation of Nilotinib Glutamate Form I

Nilotinib base (0.300 g, 0.57 mmol) was dissolved in TFE (2 mL) at 40° C. to obtain a mixture. The mixture was stirred and added to a solution of L-glutamic acid (0.042 g, 0.28 mmol) in TFE (1 mL) at 40° C. The resulting solution was stirred for about 4 h and subsequently cooled to 5° C. No precipitation was observed upon cooling. The mixture was kept at 5° C. overnight and then a sample (1 ml) was taken from the mixture and evaporated to dryness under reduced pressure at 40° C. to give Nilotinib glutamate form I.

Example 24

Preparation of Nilotinib Palmitate Form I

Nilotinib base (0.300 g, 0.57 mmol) was dissolved in TFE (2 mL) at 40° C. The stirred mixture was added to a solution of palmitic acid (0.145 g, 0.57 mmol) in TFE (1 mL) at 40° C. The resulting clear solution was stirred for about 4 h at 40° C. and it was subsequently cooled to 5° C. and kept at this temperature overnight to obtain a precipitate The precipitate was filtered and the filter cake was dried at 40° C. in a vacuum oven overnight to give Nilotinib palmitate form I.

Example 25

Preparation of Nilotinib Quinate Form I

Nilotinib base (0.300 g, 0.57 mmol) was dissolved in TFE (2 mL) at 40° C. to obtain a mixture. The mixture was stirred and added to a solution of D-quinic acid (0.109 g, 0.57 mmol) in TFE (1 mL) at 40° C. The resulting clear solution was stirred for about 4 h at 40° C. and it was subsequently cooled to 5° C. The mixture was kept at 5° C. overnight and then MTBE (1.5 v/v) was added to the mixture at room temperature leading to precipitation. The precipitate was filtered to give Nilotinib quinate form I.

Example 26

Preparation of Nilotinib Citrate Form I

Nilotinib base (0.300 g, 0.57 mmol) was dissolved in TFE (2 mL) at 40° C. to obtain a mixture. The mixture was stirred and added to a solution of citric acid (0.036 g, 0.19 mmol) in TFE (1 mL) at 40° C. The resulting clear solution was stirred for about 4 h at 40° C. and it was subsequently cooled to 5° C. The mixture was kept at 5° C. overnight and then MTBE (1.5 v/v) was added to the mixture at room temperature leading to precipitation. The precipitate was filtered to give Nilotinib citrate form I.

Example 27

Preparation of Nilotinib Citrate Amorphous Form

Nilotinib base (0.300 g, 0.57 mmol) was dissolved in TFE (2 mL) at 40° C. to obtain a mixture. The mixture was stirred and added to a solution of citric acid (0.036 g, 0.19 mmol) in TFE (1 mL) at 40° C. The resulting clear solution was stirred for about 4 h and it was subsequently cooled to 5° C. The mixture was kept at 5° C. overnight while stirring and then a sample (1 ml) was taken from the mixture and evaporated to dryness under reduced pressure at 40° C. to give amorphous Nilotinib citrate.

Example 28

Preparation of Nilotinib Citrate Amorphous Form

Figure 28:
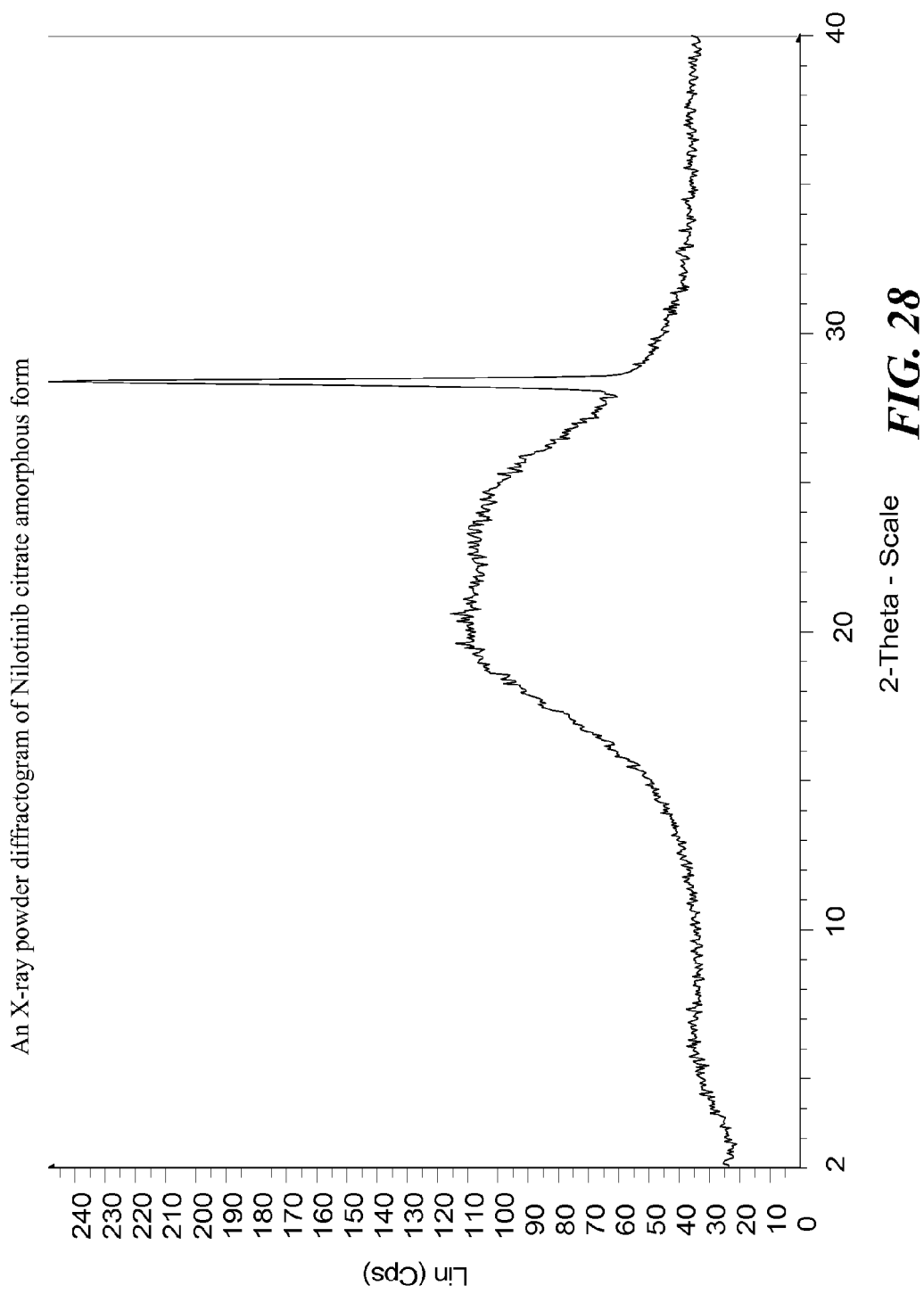
FIG. 28 shows an X-ray powder diffractogram of Nilotinib citrate amorphous form.
Figure 29:
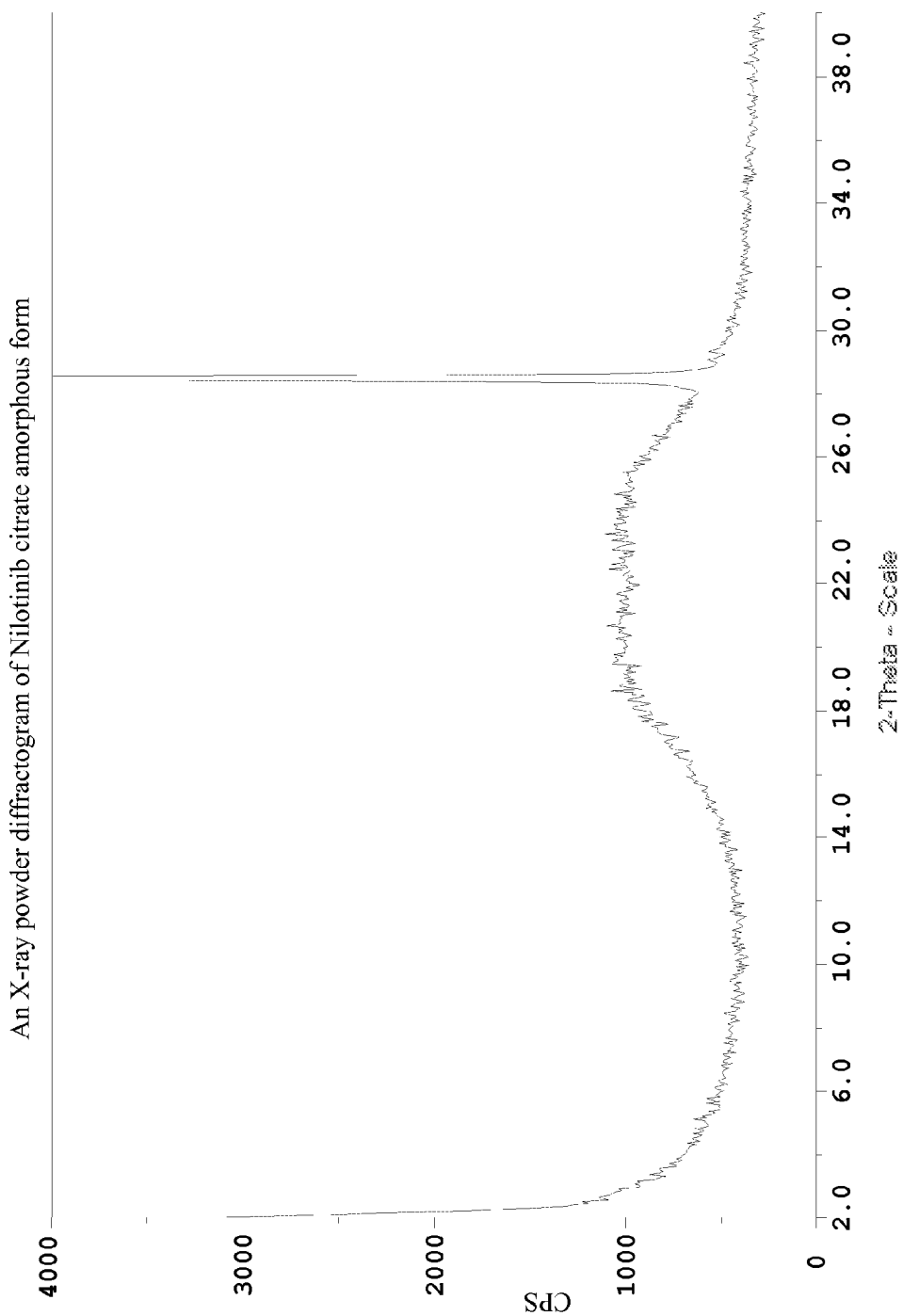
FIG. 29 shows an X-ray powder diffractogram of Nilotinib citrate amorphous form.
Figure 30:
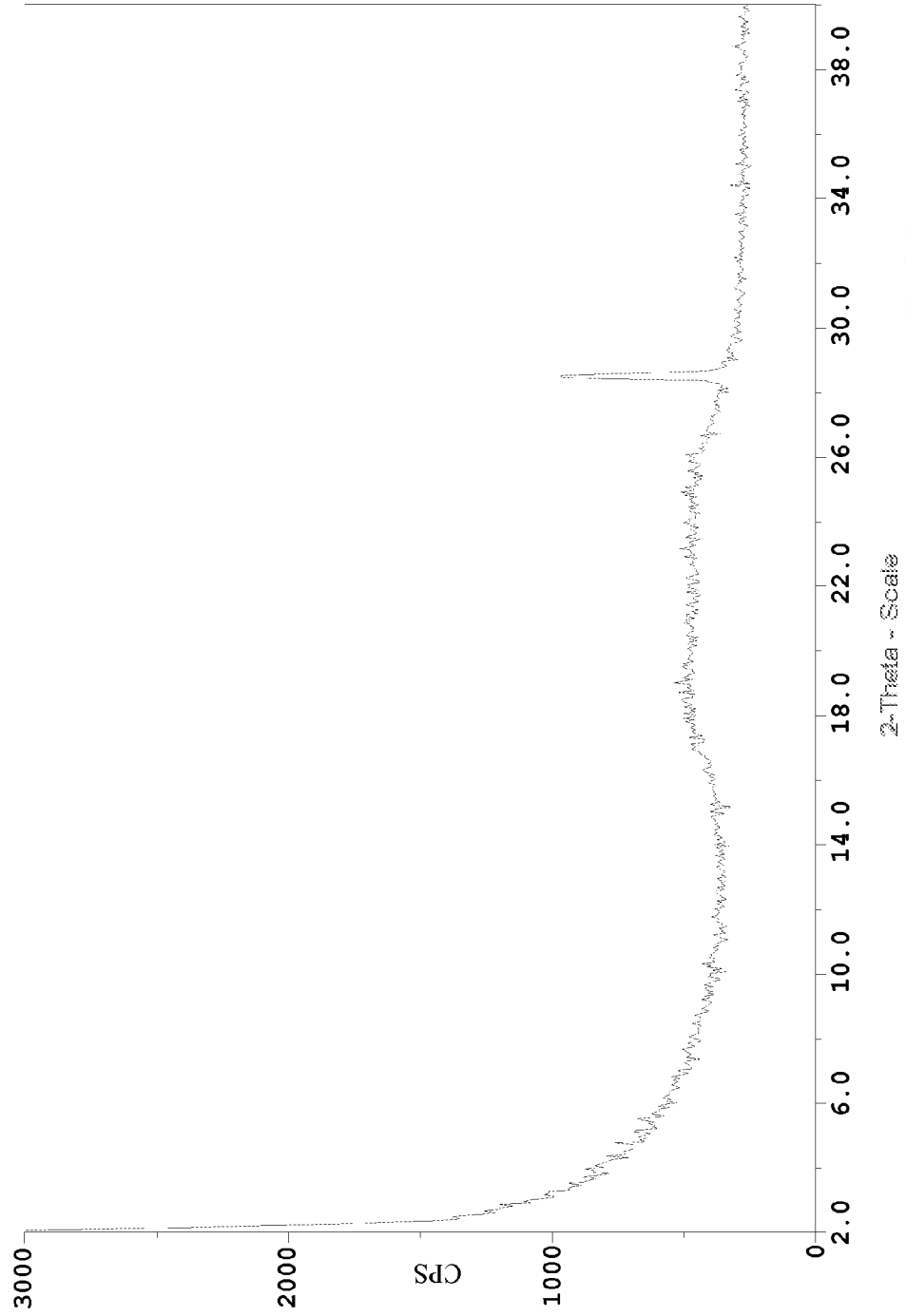
FIG. 30 shows an X-ray powder diffractogram of Nilotinib citrate amorphous form.
Figure 31:
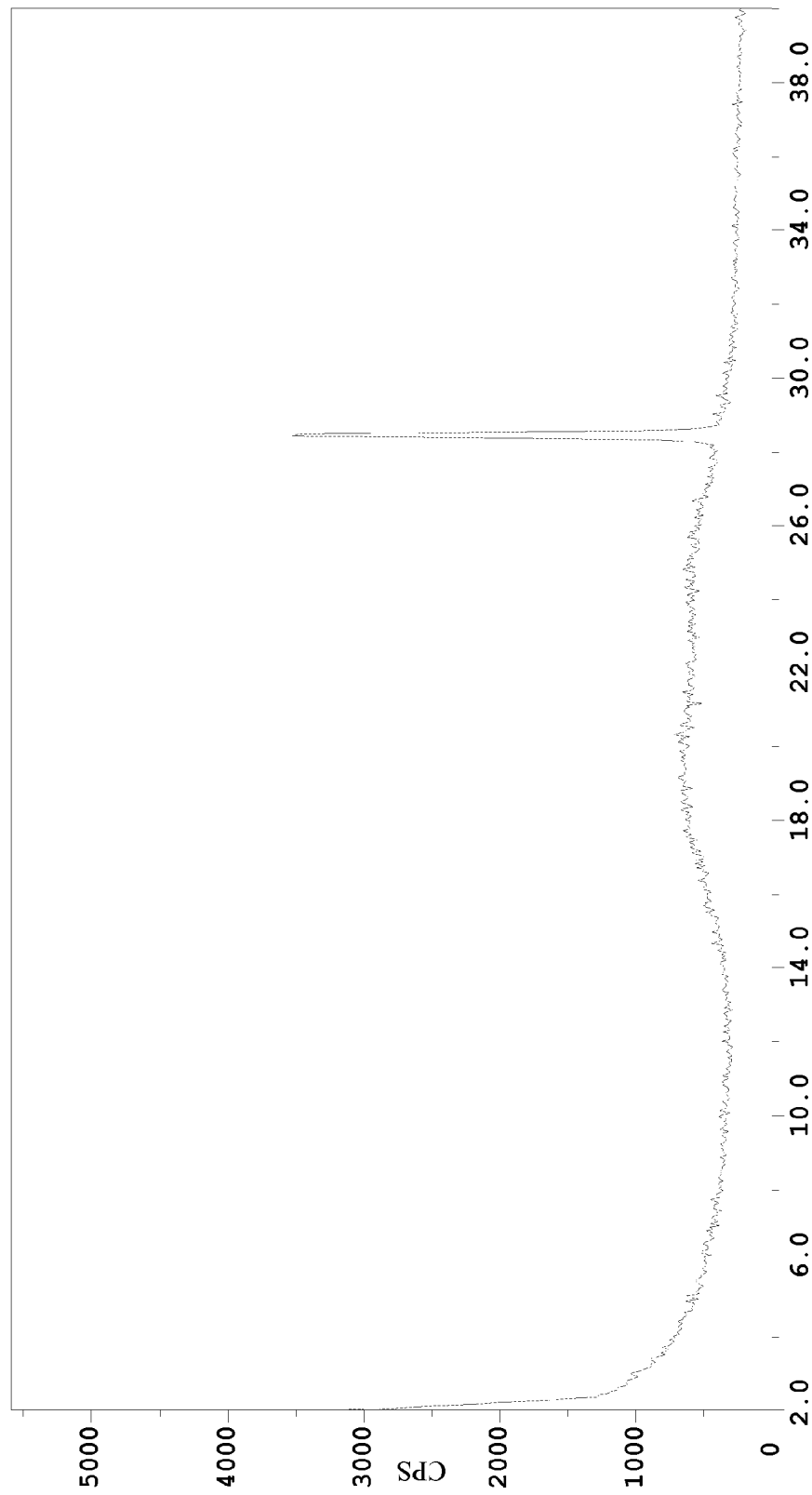
FIG. 31 shows an X-ray powder diffractogram of Nilotinib citrate amorphous form.

Nilotinibe citrate form I (obtained according to Example 26) was dried at 40° in a vacuum oven overnight to give amorphous Nilotinib citrate as characterized by the powder X-ray diffractogram depicted in FIG. 28.

Example 29

Preparation of Nilotinib Citrate Amorphous Form

Nilotinib base (0.300 g, 0.57 mmol) was dissolved in TFE (2 mL) at 40° C. to obtain a mixture. The mixture was stirred and added to a solution of citric acid (0.18 g, 0.57 mmol) in TFE (1 mL) at 40° C. The resulting clear solution was stirred for about 4 h and subsequently cooled to 5° C. The mixture was kept at 5° C. overnight and then a sample (1 mL) was taken from the mixture and evaporated to dryness under reduced pressure at 40° C. to give amorphous Nilotinib citrate as characterized by the powder X-ray diffractogram depicted in FIG. 29.

Example 30

Preparation of Nilotinib Citrate Amorphous Form

Nilotinib base (0.300 g, 0.57 mmol) was dissolved in TFE (2 mL) at 40° C. to obtain a mixture. The mixture was stirred and added to a solution of citric acid (0.18 g, 0.57 mmol) in TFE (1 mL) at 40° C. The resulting clear solution was stirred for about 4 h at 40° C. and subsequently cooled to 5° C. The mixture was kept at 5° C. overnight and then MTBE (1.5 v/v) was added to the mixture at room temperature leading to precipitation. The precipitate was filtered and the filter cake was dried at 40° C. in a vacuum oven over night to give Nilotinib amorphous citrate as characterized by the powder X-ray diffractogram depicted in FIG. 30.

Example 31

Preparation of Nilotinib Citrate Amorphous Form

Nilotinib base (0.300 g, 0.57 mmol) was dissolved in TFE (2 mL) at 40° C. to obtain a mixture. The mixture was stirred and added to a solution of citric acid (0.218 g, 1.13 mmol) in TFE (1 mL) at 40° C. The resulting clear solution was stirred for about 4 h at 40° C. and subsequently cooled to 5° C. The mixture was kept at 5° C. overnight and then MTBE (1.5 v/v) was added to the mixture at room temperature leading to precipitation. The precipitate was filtered and the filter cake was dried at 60° C. in a vacuum oven for two days to give amorphous Nilotinib citrate as characterized by the powder X-ray diffractogram depicted in FIG. 31.

Example 32

Preparation of Nilotinib Maleate Form I

Nilotinib base (0.300 g, 0.57 mmol) was dissolved in TFE (2 mL) at 40° C. to obtain a mixture. The mixture was stirred and added to a solution of maleic acid (0.033 g, 0.28 mmol) in TFE (1 mL) at 40° C. The resulting clear solution was stirred for about 4 h at 40° C. and subsequently cooled to 5° C. The mixture was kept at 5° C. overnight and then MTBE (1.5 v/v) was added to the mixture at room temperature leading to precipitation. The precipitate was filtered to give Nilotinib maleate form I.

Example 33

Preparation of Nilotinib Maleate Form II

Nilotinib base (0.300 g, 0.57 mmol) was dissolved in TFE (2 mL) at 40° C. to obtain a mixture. The mixture was stirred and added to a solution of maleic acid (0.066 g, 0.57 mmol) in TFE (1 mL) at 40° C. The resulting solution was stirred for about 4 h and subsequently cooled to 5° C. The mixture was kept at 5° C. overnight and then a sample (1 mL) was taken from the mixture and evaporated to dryness under reduced pressure at 40° C. to give Nilotinib maleate form II.

Example 34

Preparation of Nilotinib Maleate Form III

Nilotinib base (0.300 g, 0.57 mmol) was dissolved in TFE (2 mL) at 40° C. to obtain a mixture. The mixture was stirred and added to a solution of maleic acid (0.066 g, 0.57 mmol) in TFE (1 mL) at 40° C. The resulting clear solution was stirred for about 4 h at 40° C. and subsequently cooled to 5° C. The mixture was kept at 5° C. overnight and then MTBE (1.5 v/v) was added to the mixture at room temperature leading to precipitation. The precipitate was filtered and the filter cake was dried at 40° C. in a vacuum oven overnight to give Nilotinib maleate form III.

Example 35

Preparation of Nilotinib Maleate Amorphous Form

Nilotinib base (0.300 g, 0.57 mmol) was dissolved in TFE (2 mL) at 40° C. to obtain a mixture. The mixture was stirred and added to a solution of maleic acid (0.132 g, 1.13 mmol) in TFE (1 mL) at 40° C. The resulting solution was stirred for about 4 h and subsequently cooled to 5° C. The mixture was kept at 5° C. overnight and then a sample (1 mL) was taken from the mixture and evaporated to dryness under reduced pressure at 40° C. to give amorphous Nilotinib maleate.

Example 36

Preparation of Nilotinib Maleate Amorphous Form

Nilotinib base (0.300 g, 0.57 mmol) was dissolved in TFE (2 mL) at 40° C. to obtain a mixture. The mixture was stirred and added to a solution of maleic acid (0.132 g, 1.13 mmol) in TFE (1 mL) at 40° C. The resulting clear solution was stirred for about 4 h at 40° C. and subsequently cooled to 5° C. The mixture was kept at 5° C. overnight and then MTBE (1.5 v/v) was added to the mixture at room temperature leading to precipitation. The precipitate was filtered and the filter cake was dried at 60° C. in a vacuum oven for two days to give amorphous Nilotinib maleate.

Example 37

Preparation of Nilotinib Maleate Form IV

Nilotinib base (3.85 g, 7.27 mmol) was suspended in TFE (19 ml, 5V) and the mixture was heated to 40° C. with stirring. To the resulting cloudy yellow solution, maleic acid (0.84 g, 7.27 mmol) was added in one portion, followed by TFE (19 ml, 5V) at 45-50° C. Dissolution of the solid was achieved after about 5 min stirring at the same temperature. The resulting clear yellow solution was then stirred at 45° C. for about 3 h, and then at room temperature overnight (about 19 h). MTBE (10V) was added with stirring, leading to immediate precipitation. The resulting slurry was stirred for 1 h at room temperature and then the solid was separated from the mother liquors by filtration. The yellow solid was isolated and dried in a vacuum oven (35 mmHg) at 40° C. for 18.5 h to give Nilotinib maleate form IV (3.49 g, 74%) as a pale yellow solid.

Example 38

Preparation of Nilotinib Maleate Form IV

The mother liquors collected from the filtration described in example 37 were transferred to a refrigerator and maintained at 5° C. for 16 h leading to additional crystallisation. The solids were filtered and dried on the filter to give Nilotinib maleate form IV as a pale yellow solid.

Example 39

Preparation of Nilotinib Acetate Form I

Nilotinib base (0.300 g, 0.57 mmol) was dissolved in TFE (2 mL) at 40° C. to obtain a mixture. The mixture was stirred and added to a solution of acetic acid (0.034 g, 0.57 mmol) in TFE (1 mL) at 40° C. The resulting solution was stirred for about 4 h and subsequently cooled to 5° C. The mixture was kept at 5° C. overnight and then a sample (1 mL) was taken from the mixture and evaporated to dryness under reduced pressure at 40° C. to give Nilotinib acetate form I.

Example 40

Preparation of Nilotinib Acetate Form II

Nilotinib base (0.300 g, 0.57 mmol) was dissolved in TFE (2 mL) at 40° C. to obtain a mixture. The mixture was stirred and added to a solution of acetic acid (0.034 g, 0.57 mmol) in TFE (1 mL) at 40° C. The resulting clear solution was stirred for about 4 h at 40° C. and subsequently cooled to 5° C. The mixture was kept at 5° C. overnight and then MTBE (1.5 v/v) was added to the mixture at room temperature leading to precipitation. The precipitate was filtered and the filter cake was dried at 40° C. in a vacuum oven overnight to give Nilotinib acetate form II.

Example 41

Preparation of Nilotinib Acetate Form III

A solution of Nilotinib base (0.5 g, 0.94 mmol) in glacial acetic acid (2 mL, 4V) was stirred at 40° C. for 5 h. The clear yellow solution was then cooled to 5° C. and maintained at that temperature for 72 h. The mixture was then allowed to warm up to room temperature over a period of 1 h. A solid precipitate formed and was separated by filtration to give Nilotinib acetate form III.

Example 42

Preparation of Nilotinib Acetate Form IV

Nilotinib acetate form III, prepared according to example 41, was dried in a vacuum oven (30 mbar) at 40° C. for 16 h to provide Nilotinib acetate form IV.

Example 43

Preparation of Nilotinib Acetate Form V

Nilotinib base (1.5 g, 2.83 mmol) in glacial acetic acid (5 mL, 3.3V) was heated to 40° C. leading to dissolution. A precipitate was observed after stirring the solution at 40° C. for about 10 min. The mixture was then sonicated at 40° C. for 1 h leading to a clear solution. The solution was then allowed to cool to room temperature while stirring. A precipitate formed and was filtered to give Nilotinib acetate form V as a white solid.

Example 44

Preparation of Nilotinib Acetate Form VI

Nilotinib base (3.00 g, 5.66 mmol) was suspended in glacial acetic acid (12 mL, 4V) and the resulting mixture was heated to 40° C. with stirring, leading to dissolution. Stirring was continued for another 5 h at the same temperature leading to gradual precipitation. The mixture was then cooled to −18° C. and maintained at this temperature over a period of 15 h, leading to the formation of a large solid block. The solid was allowed to warm to room temperature and then heated to 40° C. for 4 h leading to a viscous suspension. The suspension was filtered and the collected solid was dried in a vacuum oven (35 mmHg) at 40° C. for 24 h to give Nilotinib acetate form VI (1.57 g) as a yellow solid.

Example 45

Preparation of Nilotinib L-Malate Form I

Nilotinib base (0.300 g, 0.57 mmol) was dissolved in TFE (2 mL) at 40° C. to obtain a mixture. The mixture was stirred and added to a solution of L-malic acid (0.038 g, 0.28 mmol) in TFE (1 mL) at 40° C. The resulting clear solution was stirred for about 4 h at 40° C. and subsequently cooled to 5° C. The mixture was kept at 5° C. overnight and then MTBE (1.5 v/v) was added to the mixture at room temperature leading to precipitation. The precipitate was filtered and the filter cake was dried at 40° C. in a vacuum oven over night to give Nilotinib L-malate form I.

Example 46

Preparation of Nilotinib L-Malate Amorphous Form

Nilotinib base (0.300 g, 0.57 mmol) was dissolved in TFE (2 mL) at 40° C. to obtain a mixture. The mixture was stirred and added to a solution of L-malic acid (0.038 g, 0.28 mmol) in TFE (1 mL) at 40° C. The resulting solution was stirred for about 2 h and it was subsequently cooled to 5° C. The mixture was kept at 5° C. overnight while stirring and then a sample (1 ml) was taken from the mixture and evaporated to dryness under reduced pressure at 40° C. to give amorphous Nilotinib L-malate as characterized by the powder X-ray diffractogram depicted in FIG. 44.

Example 47

Preparation of Nilotinib L-Malate Amorphous Form

Nilotinib base (0.300 g, 0.57 mmol) was dissolved in TFE (2 mL) at 40° C. to obtain a mixture. The mixture was stirred and added to a solution of L-malic acid (0.066 g, 0.57 mmol) in TFE (1 mL) at 40° C. The resulting solution was stirred for about 4 h and subsequently cooled to 5° C. The mixture was kept at 5° C. overnight and then a sample (1 mL) was taken from the mixture and evaporated to dryness under reduced pressure at 40° C. to give amorphous Nilotinib L-malate as characterized by the powder X-ray diffractogram depicted in FIG. 45.

Example 48

Preparation of Nilotinib L-Aspartate Form I

Nilotinib base (0.300 g, 0.57 mmol) was dissolved in TFE (2 mL) at 40° C. to obtain a mixture. The mixture was stirred and added to a solution of L-aspartic acid (0.038 g, 0.28 mmol) in TFE (1 mL) at 40° C. The resulting solution was stirred for about 4 h and subsequently cooled to 5° C. The mixture was kept at 5° C. overnight and then a sample (1 mL) was taken from the mixture and evaporated to dryness under reduced pressure at 40° C. to give Nilotinib L-aspartate form I.

Example 49

Preparation of Nilotinib L-Aspartate Form II

Nilotinib base (0.300 g, 0.57 mmol) was dissolved in TFE (2 mL) at 40° C. to obtain a mixture. The mixture was stirred and added to a solution of L-aspartic acid (0.038 g, 0.28 mmol) in TFE (1 mL) at 40° C. The resulting clear solution was stirred for about 4 h at 40° C. and subsequently cooled to 5° C. The mixture was kept at 5° C. overnight and then MTBE (1.5 v/v) was added to the mixture at room temperature leading to precipitation. The precipitate was filtered and the filter cake was dried at 40° C. in a vacuum oven overnight to give Nilotinib L-aspartate form II.

Example 50

Preparation of Nilotinib L-Aspartate Form III

Nilotinib base (0.300 g, 0.57 mmol) was dissolved in TFE (2 mL) at 40° C. to obtain a mixture. The mixture was stirred and added to a solution of L-aspartic acid (0.076 g, 0.57 mmol) in TFE (1 mL) at 40° C. The resulting clear solution was stirred for about 4 h at 40° C. and subsequently cooled to 5° C. The mixture was kept at 5° C. overnight and then MTBE (1.5 v/v) was added to the mixture at room temperature leading to precipitation. The precipitate was filtered and the filter cake was dried at 40° C. in a vacuum oven overnight to give Nilotinib L-aspartate form III.

Example 51

Preparation of Nilotinib Formate Amorphous Form

Nilotinib base (0.300 g, 0.57 mmol) was dissolved in TFE (2 mL) at 40° C. to obtain a mixture. The mixture was stirred and added to a solution of formic acid (0.0261 g, 0.57 mmol) in TFE (1 mL) at 40° C. The resulting solution was stirred for about 4 h and subsequently cooled to 5° C. The mixture was kept at 5° C. overnight and then a sample (1 mL) was taken from the mixture and evaporated to dryness under reduced pressure at 40° C. to give amorphous Nilotinib formate as characterized by the powder X-ray diffractogram depicted in FIG. 49.

Example 52

Preparation of Nilotinib Formate Amorphous Form

Nilotinib base (0.300 g, 0.57 mmol) was dissolved in TFE (2 mL) at 40° C. to obtain a mixture. The mixture was stirred and added to a solution of formic acid (0.052 g, 1.13 mmol) in TFE (1 mL) at 40° C. The resulting solution was stirred for about 4 h and subsequently cooled to 5° C. The mixture was kept at 5° C. overnight and then a 1 mL sample was taken from the mixture and evaporated to dryness under reduced pressure at 40° C. to give amorphous Nilotinib formate as characterized by the powder X-ray diffractogram depicted in FIG. 50.

Example 53

Preparation of Nilotinib Hydrobromide Form I

Nilotinib base (0.5 g, 0.94 mmol) was dissolved in TFE (5 mL, 10V) to obtain a mixture. The mixture was stirred at 40° C. HBr (48% aq., 0.175 g, 1.1 eq) was added to the resulting clear pale yellow solution. The solution was stirred at 40° C. for 5 h. The mixture was then cooled to 5° C. while stirring for 16 h. The resulting precipitate was isolated by filtration to give Nilotinib hydrobromide form I.

Example 54

Preparation of Nilotinib Hydrobromide Form II

Nilotinib hydrobromide form I, prepared according to example 53, was dried in a vacuum oven (30 mbar) at 40° C. for 17 h to provide Nilotinib HBr form II (0.2 g).

Example 55

Preparation of Nilotinib Hydrobromide Form III

A mixture of Nilotinib base (2.00 g, 3.77 mmol) and TFE (12 mL, 6V) was stirred and heated to 55° C. to provide a clear pale yellow solution. The solution was cooled to 50° C. and HBr (48% aq, 0.4 mL, 8.31 mmol, 2.2 eq) was added. The resulting deep yellow solution was stirred at 50° C. for 1 h, and then cooled to ambient temperature. Stirring was continued for 2 h and then the mixture was cooled to 5° C. in an ice-bath. About ⅔V of the solvent were removed under reduced pressure and the resulting mixture was kept in a refrigerator (5° C.) overnight. A solid precipitated and was separated by filtration to give Nilotinib HBr form III.

Example 56

Preparation of Nilotinib Hydrobromide Form IV

Nilotinib base Form A (3.50 g, 6.61 mmol) was suspended in EtOH (70 mL, 20V) and the resulting slurry was heated to 50° C. over 15 min with stirring. To the resulting pale yellow slurry was added HBr (48% aq., 1.23 g, 7.27 mmol, 1.1 eq) followed by another 2V of EtOH (7 mL). This addition led to a colour change to give a neon yellow suspension. The suspension was heated to reflux and another 18V EtOH (63 mL) was added portion-wise with stirring. After 1.5 h the suspension was removed from the heat source and stirred at room temperature overnight. After about 15 h the suspension was subjected to hot filtration (60° C.) under nitrogen. The mother liquors were separated from the solid and the collected solid was dried in a vacuum oven (35 mmHg) at 40° C. for 20 h to give Nilotinib HBr form IV (1.86 g) as a yellow solid.

Example 57

Preparation of Nilotinib Hydrobromide Form V

The mother liquors collected during the hot filtration in example 55 above were evaporated to dryness to afford Nilotinib HBr form V (3.32 g) as a yellow solid.

Example 58

Preparation of Nilotinib Hydrobromide Form VI

Nilotinib base (2.00 g, 3.77 mmol) was mixed with glacial acetic acid (8.00 mL, 4.0V). The mixture was heated to 40° C. with stirring which lead to a clear yellow solution. HBr 33% in acetic acid (0.8 mL, 4.53 mmol, 1.2 eq) was added in one portion to the stirred solution, leading to the formation of a yellow suspension. Stirring was continued at 40° C. over a period of 1 h. Due to the high viscosity of the mixture another 5 mL acetic acid (2.5V) was added. The mixture was then allowed to cool to room temperature by removal of the heat source, and the mixture was stirred at room temperature for an additional 4 h. The suspension was then filtered to give Nilotinib HBr form VI. The obtained product was dried in a vacuum oven (35 mmHg) at 40° C. for 3 days. The dried product was analyzed by PXRD and was found to be Nilotinib HBr form VI. The dried product was then subjected to additional drying at 60° C. in a vacuum oven for 15 hours, and then it was analyzed by PXRD and was found to be Nilotinib HBr form VI.

Example 59

Preparation of Nilotinib Maleate Form V

Nilotinib base form A (4.00 g, 7.55 mmol) was stirred with EtOH abs (40 mL, 10V) and the suspension was heated to 80° C. Stirring was continued at the same temperature for 30 min. To the stirred suspension was added a solution of maleic acid (0.96 g, 8.31 mol. 1.1 eq) in EtOH abs (10 mL, 2.5V) in one portion. The resulting mixture was stirred at 80° C. for 1 h and then cooled to room temperature and stirred for another 6 h. The solids were isolated by filtration to give Nilotinib maleate form V. The obtained Nilotinib maleate form V was dried in a vacuum oven (35 mmHg) at 60° C. for 16 hours. The dried product was analyzed by PXRD and was found to be Nilotinib maleate form V. Mono maleate was obtained as confirmed by assay determination.

Example 60

Preparation of Nilotinib Hydrobromide Form VII

Nilotinib base Form A (2.00 g, 3.77 mmol) was mixed with EtOH abs (50 mL, 25V) and the resulting suspension was heated to 80° C. and stirred at the same temperature for 30 min. Gaseous HBr was bubbled through the stirred suspension over a period of 5 min and dissolution was observed followed by the precipitation of an orange solid. The heating source was removed and the mixture was allowed to cool to ambient temperature whilst stirring over a period of 4 h. The resulting light orange solid was isolated by vacuum filtration to give Nilotinib HBr form VII. The obtained Nilotinib HBr form VII was dried in a vacuum oven (35 mmHg) at 60° C. for 16 h. The dried product was analyzed by PXRD and was found to be Nilotinib hydrobromide form VII.

Example 61

Preparation of Nilotinib Malonate Form I

Nilotinib base Form A (3.00 g, 5.67 mmol) was dissolved in TFE (29 mL, 9.7V) at room temperature with stirring. Separately, malonic acid (0.62 g, 5.95 mmol, 1.05 mol eq), was mixed with TFE (3 mL) and heated to 68° C. to afford dissolution. The malonic acid solution was added to the solution of Nilotinib base in TFE at 68° C. and stirring was continued at the same temperature for 5 h. The heating source was removed and the mixture was allowed to cool to ambient temperature over a period of 30 min. Then, the mixture was transferred to the refrigerator and kept at 5° C. for 16 h. Methyl tert-butyl ether ("MTBE") (30 mL) was then added and the resulting mixture was stirred at room temperature for about 20 min leading to the formation of a white precipitate. The precipitate was filtered and dried overnight in a vacuum oven (60° C.) to give Nilotinib malonate form I.

Example 62

Preparation of Nilotinib L-Tartrate Form IV

Nilotinib base form A (4.00 g, 7.55 mmol) was mixed with ethanol absolute (40 mL, 10V) in a 250 mL reactor equipped with a mechanical stirrer and a reflux condenser to obtain a suspension. The suspension was heated to 80° C. and stirred at the same temperature for 30 min. To the suspension was added a solution of L-tartaric acid (1.25 g, 8.31 mmol, 1.1 mol eq) in ethanol absolute (10 mL, 2.5V) in one portion. The resulting mixture was stirred at 80° C. for 1 hour. Then the heating source was removed and the mixture was allowed to cool to room temperature. The stirring was continued at ambient temperature over a period of 6 h, during which time the mixture became viscous. To the viscous mixture was added another 80 mL ethanol. The mixture was then transferred to the refrigerator and was kept at about 5° C. for 5 days (in a closed vessel) A yellow precipitate formed and was isolated by vacuum filtration to give Nilotinib L-tartrate form IV as indicated by XRD (wet sample). The obtained Nilotinib L-tartrate form IV was dried in a vacuum oven (35 mmHg) at 60° C. for 16 h. The sample was then analyzed by PXRD using a Bruker X-Ray powder diffractometer model D8 and was found to be Nilotinib L-tartrate form IV (4.7 g).

Example 63

Preparation of Nilotinib L-Tartrate Form V

Nilotinib base Form A (4.00 g, 7.55 mmol) was mixed with dimethylformamide ("DMF") (40 mL, 10V) to obtain a suspension. The suspension was heated to 80° C. and stirred at the same temperature for 30 min to produce a clear yellow solution. To the solution was added a solution of L-tartaric acid (1.25 g, 8.31 mmol, 1.1 mol eq) in DMF (4 mL, 1V) in one portion. The solution was stirred at 80° C. for 1 hour. Then the heating source was removed and the mixture was allowed to cool to room temperature. The stirring was continued at ambient temperature over a period of 6 h after which time the mixture was transferred to the refrigerator for 16 h. MTBE (400 mL) was added portion-wise to the mixture at room temperature until a light yellow precipitate was formed. The resulting suspension was stirred at room temperature for 6 h and then filtered to give Nilotinib L-tartrate form V as a light-yellow solid.

Example 64

Preparation of Nilotinib L-Tartrate Form VI

Nilotinib L-tartrate form V was dried in a vacuum oven (35 mmHg, 60°) for 36 h. The sample was analyzed by PXRD and was found to be Nilotinib L-tartrate form VI (4.22 g).

Example 65

Preparation of Nilotinib Oxalate Form I

Nilotinib base Form A (4.00 g, 7.55 mmol) was suspended in EtOH abs. (40 mL, 10V) at room temperature. The suspension was heated to 80° C. and stirred at that temperature for 30 min. A solution of oxalic acid (1.38 g, 15.33 mmol, 2.03 mol eq) in EtOH abs. (10 mL 2.5V) was added in one portion and a suspension was obtained. Stirring of the suspension was continued for 1 h at 80° C. The reaction vessel was then allowed to cool to ambient temperature by removal of the reaction vessel from the heating source, and the mixture was stirred at ambient temperature for 6 h. Another 20 mL EtOH abs. was added during this time to improve the stirring. A yellow precipitate formed and was isolated by vacuum filtration and dried in a vacuum oven (35 mmHg) at 70° C. for 24 h to give Nilotinib oxalate form I (5.3 g) as a yellow solid. The sample was analyzed by PXRD (Bruker X-Ray powder diffractometer model D8 advance equipped with lynxEye). Di oxalate salt was obtained according to assay determination.

Example 66

Preparation of Nilotinib Hydrobromide Form VIII

Nilotinib base Form A (4.00 g, 7.55 mmol) was suspended in EtOH abs. (40 mL, 10V) at room temperature. The suspension was heated to 80° C. and stirred for 30 min. HBr (48% aq., 0.9 mL, 7.78 mmol, 1.03 eq) was added in one portion. The suspension was stirred for one hour at 80° C. then cooled to ambient temperature by removal of the heating source. The stirring was then continued for about 20 h. A yellow solid was isolated by filtering the suspension thereby providing Nilotinib HBr form VIII. The sample was analyzed by PXRD (ARL X-ray powder diffractometer model X'TRA-019).

Example 67

Preparation of Nilotinib Hydrobromide Form IX

Nilotinib base Form A (4.00 g, 7.55 mmol) was suspended in EtOH abs. (40 mL, 10V) at room temperature. The suspension was heated to 80° C. and stirred for 30 min. HBr (48% aq., 1.7 mL, 15.33 mmol, 2.03 eq) was added in one portion. The suspension was stirred for 1 h at 80° C. and then cooled to ambient temperature by removal of the heating source. Stirring was then continued for about 6 h. The resulting yellow solid was isolated by filtration to give Nilotinib HBr form IX. (ARL X-ray powder diffractometer model X'TRA-019).

Example 68

Preparation of Nilotinib Hydrobromide Form X

Nilotinib base Form A (4.00 g, 7.55 mmol) was suspended in acetone (40 mL, 10V) at room temperature. The suspension was heated to reflux and stirred for 30 min. HBr (33% in acetic acid, 1.4 mL, 7.78 mmol, 1.03 eq) was added in one portion. The suspension was stirred for 1 h at reflux and then cooled to ambient temperature by removal of the heating source. The stirring was continued for about 6 h. The resulting yellow solid was isolated by filtration and dried in a vacuum oven (35 mmHg) at 70° C. for 15 h to give Nilotinib HBr form X as a yellow solid. (ARL X-ray powder diffractometer model X'TRA-019).

Example 69

Preparation of Nilotinib Hydrobromide Form XI

Nilotinib base Form A (4.00 g, 7.55 mmol) was mixed with acetone (40 mL, 10V) and the resulting suspension was heated to reflux and stirred for 0.5 h. To the mixture was then added HBr (48% aq., 0.9 mL, 7.78 mmol, 1.03 eq) in one portion and stirring was continued at reflux temperature for 0.5 h. The mixture was then allowed to cool to room temperature by removal of the heating source, and was stirred at room temperature for 6 h. The flask containing the mixture was then transferred to a refrigerator where it was kept for about 3 days at 2° C. to about 8° C. (in a closed vessel). The mixture was then filtered and the isolated solid was dried in a vacuum oven (35 mmHg) at 70° C. for 24 h to afford Nilotinib HBr form XI as a yellow solid. The sample was analyzed in ARL X-ray powder diffractometer model X'TRA-019, and $^{13}$C NMR spectra are provided in FIGS. 73-74.

Example 70

Preparation of Nilotinib Hydrochloride Form T17

To a 1 liter reactor was added Nilotinib-base (20 g, 0.04 mol), absolute ethanol (9.4 vol) and HCl solution (13.77% in ethanol abs., 10 g, 0.04 mol). The resulting slurry was heated to reflux, and dissolution occurred during the stirring. The solution was filtered under reduced pressure. The filtrate was fed back to the reactor and heated back to reflux temperature. At 76.6° C. the solution was seeded with 0.2 g of dry Nilotinib HCl form T17. A solid precipitate was formed, and the mixture was maintained at reflux for 1 hour. The mixture was then cooled over 2 h to 6° C. At 6° C., absolute ethanol (15 vol) was added and the resulting slurry was stirred at 5° C. for 30 minutes. The slurry was then filtered, and the separated solid was washed with absolute ethanol, and dried overnight at 70° C. in a vacuum oven to yield Nilotinib-HCl form T17 (18.4 g, 83% yield)

Example 71

Preparation of Nilotinib Hydrochloride Form T27

The mother liquor (2 Kg) from the preparation of Nilotinib HCl form T17 in example 70 (a slightly turbid yellow solution) was concentrated to dryness in a 1 liter reactor by applying vacuum (50 mm Hg) and heating the reactor jacket (50-60° C.). The resulting residue was maintained under a nitrogen atmosphere at ambient temperature overnight. Then, absolute ethanol (896 mL) was added to the reactor and the resulting mixture was heated to reflux (76-79° C.). The pH was measured as 1.33. The slurry was filtered under vacuum and dried overnight in a vacuum oven at 90° C. to yield form T27. The product was analyzed in an ARL X-ray powder diffractometer model X'TRA-019).

Example 72

Preparation of Nilotinib Hydrochloride Form T28

Nilotinib HCl form T17 (0.2 g, 0.35 mmol) was added to a 25 ml vial and the open vial was placed in a plastic sealed flask which contained 10 mL of HCl (32%, aq.) and this assembly was maintained at room temperature for 120 hours. A solid formed and was separated and dried in a vacuum oven at 90° C. overnight to yield form T28.

Example 73

Preparation of Nilotinib Hydrochloride Form T29

Nilotinib hydrochloride form T17 (0.2 g, 0.35 mmol) was added to a 25 mL vial and the open vial was placed in a plastic sealed flask which contained 10 mL of HCl (12.04% solution in absolute ethanol) and this assembly was maintained at room temperature, for 120 hours. The resulting solid was dried in a vacuum oven at 90° C. overnight to yield form T29.

Example 74

Preparation of Nilotinib Hydrochloride Form T29

Nilotinib base form A (0.2 g, 0.38 mmol) was added to a 25 mL vial and the open vial was placed in a plastic sealed flask which contained 10 ml of HCl (12.04% in abs. ethanol) and this assembly was maintained at room temperature for 120 hours. The resulting solid was dried in a vacuum oven at 90° C. overnight to yield form T29.

Example 75

Preparation of Nilotinib Hydrobromide Form XI

In a 250 mL reactor equipped with a reflux condenser and a mechanical stirrer Nilotinib base Form A (15.00 g, 28.3 mmol) was mixed with acetone (150 mL, 10V). The resulting suspension was heated to reflux over 10 min and stirred at reflux for additional 40 min. To the stirred suspension was added HBr (48% aq, 3.30 mL, 29.2 mmol, 1.03 eq) in one portion. Stirring of the resulting mixture was continued at reflux temperature for 1 h. The mixture was then allowed to cool to room temperature over a period of 3 h and maintained at room temperature overnight. The flask containing the mixture was then transferred to the refrigerator where it was kept for about 3 days at a temperature from 2° C. to about 8° C. (in a closed vessel). The mixture was then filtered and the isolated solid was dried in a vacuum oven (25 mmHg) at 70° C. for 22 h to afford Nilotinib HBr form XI as a yellow solid (17.27 g, 99%). Assay determination confirmed the stoichiometry of the salt as monohydrobromide.

Example 76

Preparation of Nilotinib Hydrobromide Form XI

Nilotinib base Form A (4.00 g, 7.55 mmol) was suspended in acetone (40 mL). The resulting mixture was stirred and heated to reflux for 0.5 h. HBr (48% aq., 0.88 mL, 7.78 mmol, 1.03 eq) was then added in one portion. The resulting mixture was refluxed for 10 min and then cooled to room temperature over 1 h. Then it was stirred at room temperature over 16 h and a solid precipitate formed. The solid was isolated by vacuum filtration and dried in a vacuum oven at 70° C. for 32 h to give Nilotinib HBr form XI as a yellow solid (4.42 g, 96%). Monohydrobromide salt was obtained according to assay determination.

Example 77

Preparation of Nilotinib L-Tartrate Form IV

Figure 71:
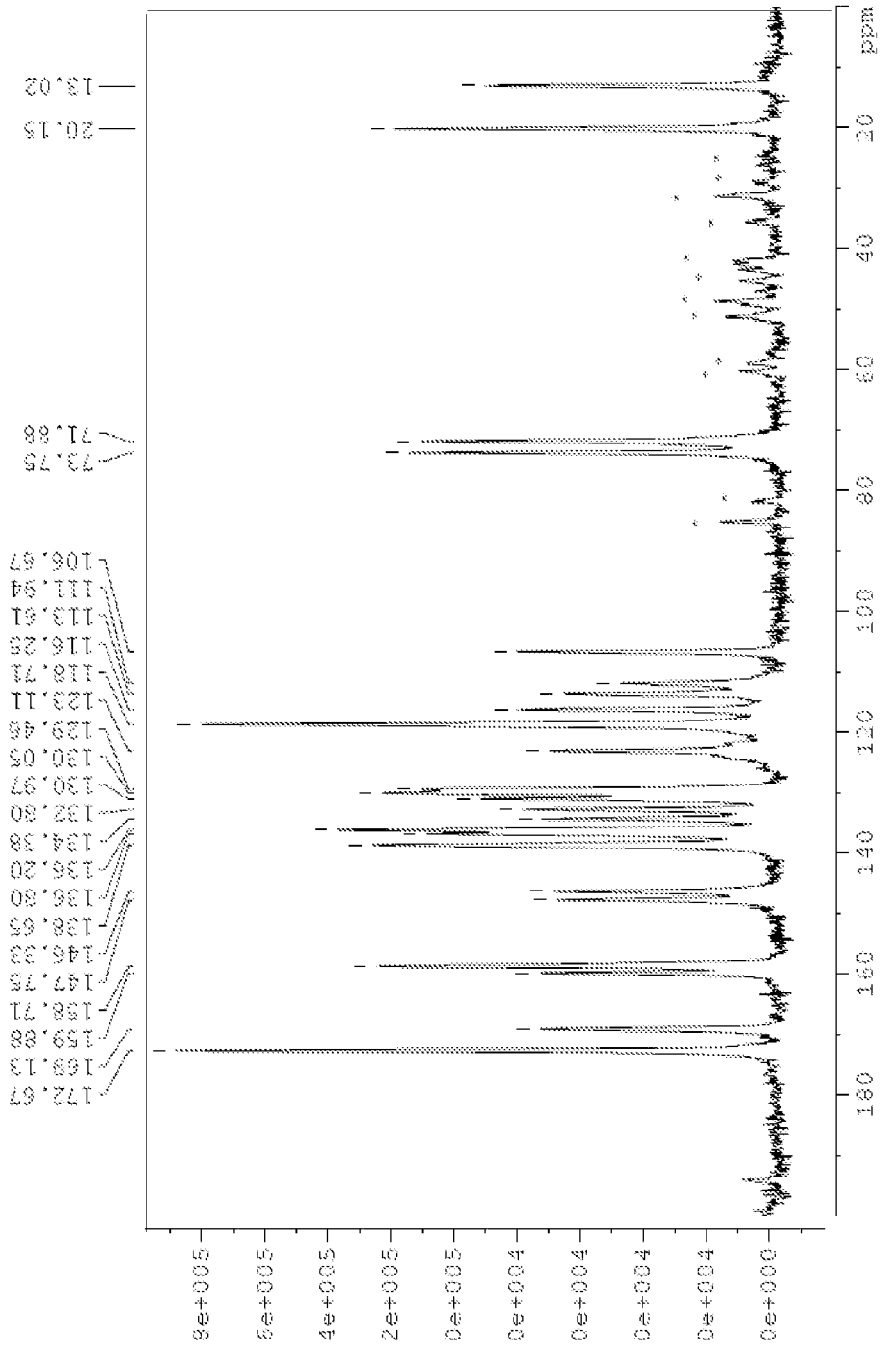
FIG. 71 shows a $^{13}$C NMR spectrum of Nilotinib L-tartrate crystalline form IV between 0-200 ppm.
Figure 72:
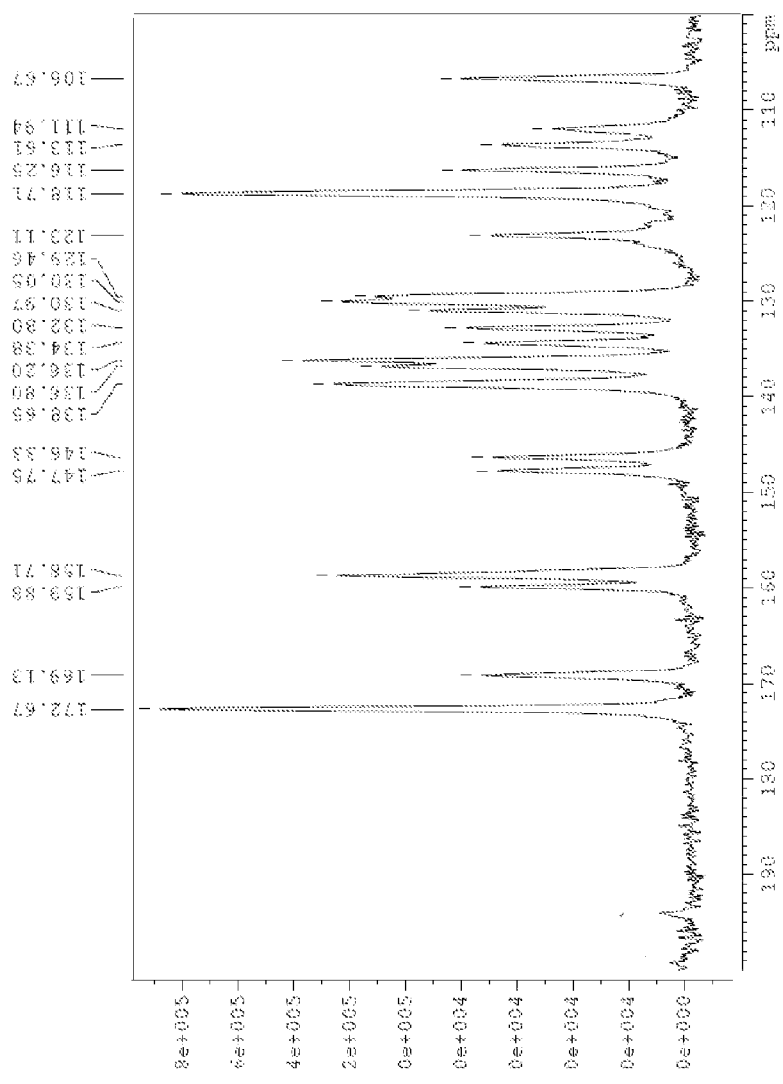
FIG. 72 shows a $^{13}$C NMR spectrum of Nilotinib L-tartrate crystalline form IV between 100-200 ppm.

Nilotinib base Form A (8.00 g, 15.11 mmol) was suspended in absolute EtOH (80 mL, 10V). The suspension was heated to 80° C. and stirred for 0.5 h. To the resulting mixture was then added a solution of L-tartaric acid (2.49 g, 16.7 mmol, 1.1 eq) in absolute EtOH (20 mL) in one portion, followed by an additional 120 mL of absolute EtOH. The resulting mixture was stirred at 80° C. for 1 h and then allowed to cool to room temperature by removal of the heat source over 1 h with continuous stirring at room temperature for another 6 h. The mixture was then transferred to a refrigerator at 5° C. and kept there for 16 h (in a closed vessel). The solid was isolated by vacuum filtration and dried in a vacuum oven at 70° C. for 24 h to give Nilotinib form IV. $^{13}$C NMR is shown in FIGS. 71-72. Mono L-tartrate salt was obtained according to assay determination.

Example 78

Preparation of Nilotinib L-Tartrate Form IV

A 250 mL reactor equipped with a reflux condenser and a mechanical stirrer was charged with Nilotinib base Form A (8.00 g, 15.11 mmol) and absolute EtOH (80 mL, 10V). The suspension was heated to 80° C. and stirred for 0.5 h. To the resulting mixture was added a solution of L-tartaric acid (2.49 g, 16.7 mmol, 1.1 eq) in absolute EtOH (20 mL) in one portion, followed by an additional 120 mL of absolute EtOH. The resulting mixture was stirred at 80° C. during 20 min and then cooled to room temperature over 0.5 h with continuous stirring at room temperature for another 16 h. The mixture was then transferred to a refrigerator at 5° C. and kept there for 16 h (in a closed vessel). The solid was isolated by vacuum filtration and dried in a vacuum oven at 70° C. for 24 h to give Nilotinib L-tartrate form IV as a yellow solid (9.10 g, 89%). Mono L-tartrate salt was obtained according to assay determination.

Example 79

Preparation of Nilotinib Maleate Form V

Nilotinib base form A (4.00 g, 7.55 mmol) was stirred with IPA (40 mL, 10V) and the suspension was heated to 80° C. Stirring was continued at the same temperature for 30 min. To the stirred suspension was added a solution of maleic acid (0.96 g, 8.31 mol. 1.1 eq) in IPA (10 mL, 2.5V) in one portion. The resulting mixture was stirred at 80° C. for 1 h and then cooled to room temperature and stirred over night. The solids were isolated by filtration to give Nilotinib maleate form V. The obtained Nilotinib maleate form V was dried in a vacuum oven (35 mmHg) at 60° C. for 32 hours. The dried product was analyzed by PXRD and was found to be Nilotinib maleate form V. Mono maleate was obtained as confirmed by assay determination.

What is claimed is:

1. A Crystalline Form of Nilotinib L-tartrate selected from:
  a) Crystalline Form I of Nilotinib L-tartrate, characterized by data selected from: an X-ray powder diffraction pattern having peaks at 9.4, 11.7, 12.7, 18.2 and 19.0 degrees two theta+0.2 degrees two theta; an X-ray powder diffraction pattern substantially as depicted in FIG. 14, and combinations thereof;
  b) Crystalline Form II of Nilotinib L-tartrate, characterized by data selected from: an X-ray powder diffraction pattern having peaks at 8.7, 15.7, 17.2, 19.4 and 20.0 degrees two theta+0.2 degrees two theta; an X-ray powder diffraction pattern substantially as depicted in FIG. 15; and combinations thereof;
  c) Crystalline Form III of Nilotinib L-tartrate, characterized by data selected from: an X-ray powder diffraction pattern having peaks at 8.2, 9.1, 12.3, 15.0 and 17.6 degrees two theta+0.2 degrees two theta; an X-ray powder diffraction pattern substantially as depicted in FIG. 16; and combinations thereof;
  d) Crystalline Form IV of Nilotinib L-tartrate, characterized by data selected from: an X-ray powder diffraction pattern having peaks at 13.6, 18.3, 19.5, 21.9 and 24.3 degrees two theta+0.2 degrees two theta; an X-ray powder diffraction pattern substantially as depicted in FIG. 60; and combinations thereof;
  e) Crystalline Form V of Nilotinib L-tartrate, characterized by data selected from: an X-ray powder diffraction pattern having peaks at 3.6, 7.6, 14.1, 17.8 and 19.5 degrees two theta+0.2 degrees two theta; an X-ray powder diffraction pattern substantially as depicted in FIG. 61; and combinations thereof; and
  f) Crystalline Form VI of Nilotinib L-tartrate, characterized by data selected from: an X-ray powder diffraction pattern having peaks at 4.7, 12.1, 16.3, 21.0 and 24.4 degrees two theta+0.2 degrees two theta; an X-ray powder diffraction pattern substantially as depicted in FIG. 62; and combinations thereof.

2. Crystalline Form IV of Nilotinib L-tartrate according to claim 1, characterized by: an X-ray powder diffraction pattern having peaks at 13.6 18.3, 19.5, 21.9 and 24.3 degrees two theta±0.2 degrees two theta.

3. The crystalline Nilotinib L-tartrate according to claim 2, further characterized by data selected from: a solid state 13C NMR spectrum having signals at 118.7, 136.2 and 172.7+0.2 ppm; a solid-state 13C NMR spectrum having chemical shift differences between the signal exhibiting the lowest chemical shift in the chemical shift range of 100 to 180 ppm and another in the chemical shift range of 100 to 180 ppm of 12.0, 29.5 and 66.0+0.1 ppm; a solid state 13C NMR spectrum as depicted in any one of FIGS. 71-72; and combinations thereof.

4. The crystalline Nilotinib L-tartrate according to claim 2, further characterized by an X-ray powder diffraction pattern having any one, two, three, four or five additional peaks selected from peaks at 10.6, 11.3, 20.8, 22.9 and 25.0 degrees two theta±0.2 degrees two theta.

5. The crystalline Nilotinib L-tartrate according to claim 2, wherein the crystalline form is anhydrous.

6. The crystalline Nilotinib L-tartrate according to claim 2, wherein the crystalline form is of Nilotinib mono L-tartrate salt.

Figure 73:
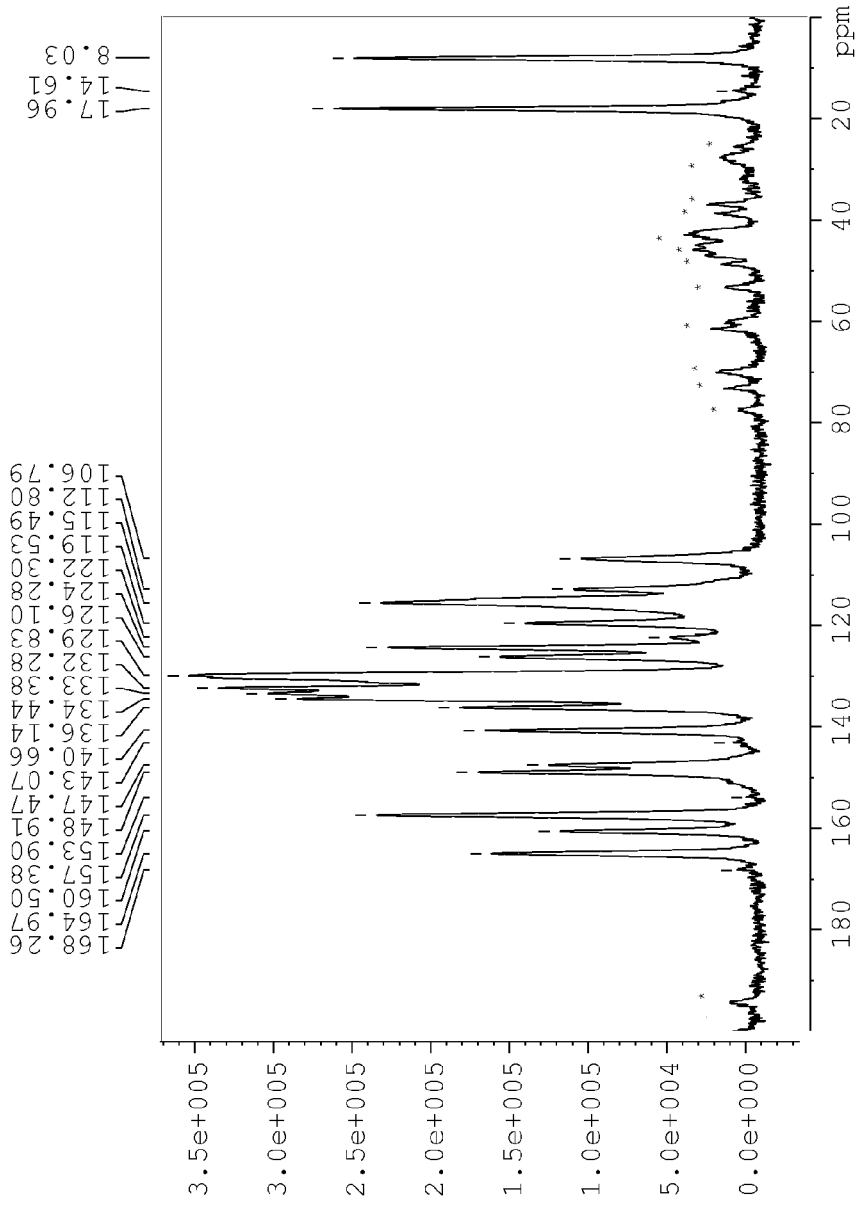
FIG. 73 shows a $^{13}$C NMR spectrum of Nilotinib HBr crystalline form XI between 0-200 ppm.
Figure 74:
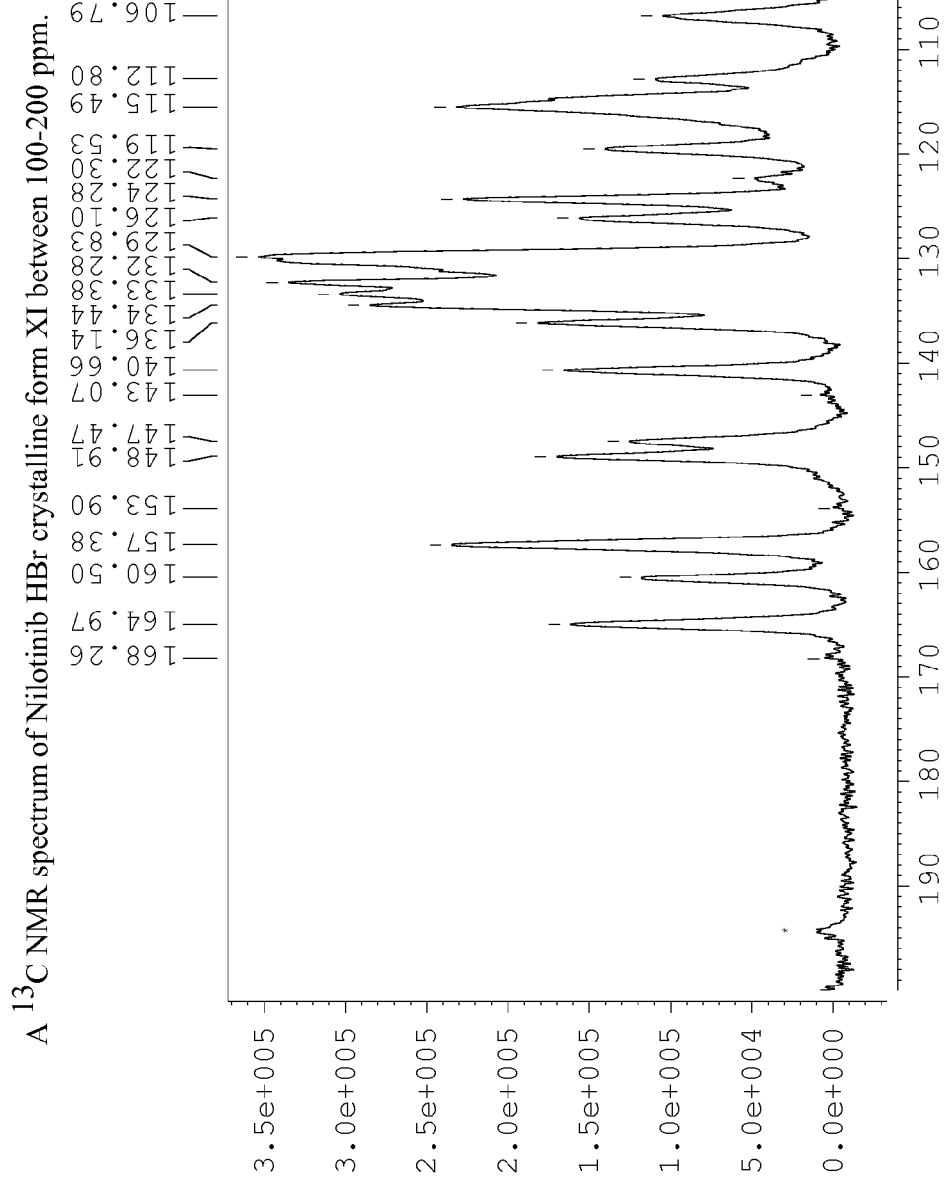
FIG. 74 shows a $^{13}$C NMR spectrum of Nilotinib HBr crystalline form XI between 100-200 ppm.

7. A crystalline form of Nilotinib hydrobromide selected from:
  a) Nilotinib hydrobromide form I, characterized by data selected from: an X-ray powder diffraction pattern having peaks at 4.8, 6.8, 9.0, 9.6 and 13.6 degrees two theta±0.2 degrees two theta, an X-ray powder diffraction pattern substantially as depicted in FIG. 51, and combinations thereof;
  b) Nilotinib hydrobromide form II, characterized by data selected from: an X-ray powder diffraction pattern having peaks at 17.3, 21.5, 24.5 and 26.5 degrees two theta±0.2 degrees two theta and a broad peak having a maximum at 20.8 degrees two theta±0.2 degrees two theta, an X-ray powder diffraction pattern substantially as depicted in FIG. 52, and combinations thereof;
  c) Nilotinib hydrobromide form III, characterized by data selected from: an X-ray powder diffraction pattern having peaks at 6.5, 8.5, 12.3, 19.5 and 20.6 degrees two theta±0.2 degrees two theta, an X-ray powder diffraction pattern substantially as depicted in FIG. 53, and combinations thereof;
  d) Nilotinib hydrobromide form IV, characterized by data selected from: an X-ray powder diffraction pattern having peaks at 4.7, 9.3, 11.3, 14.0 and 20.2 degrees two theta±0.2 degrees two theta, an X-ray powder diffraction pattern substantially as depicted in FIG. 54, and combinations thereof;
  e) Nilotinib hydrobromide form V, characterized by data selected from: an X-ray powder diffraction pattern having peaks at 7.4, 9.4, 12.0, 14.8 and 16.0 degrees two theta±0.2 degrees two theta, an X-ray powder diffraction pattern substantially as depicted in FIG. 55, and combinations thereof;

f) Nilotinib hydrobromide form VI, characterized by data selected from: an X-ray powder diffraction pattern having peaks at 2.9, 11.8, 12.8, 18.4 and 22.3 degrees two theta±0.2 degrees two theta, an X-ray powder diffraction pattern substantially as depicted in FIG. 56, and combinations thereof;

g) Nilotinib hydrobromide form VII, characterized by data selected from: an X-ray powder diffraction pattern having peaks at 8.1, 12.2, 13.8, 16.3 and 23.3 degrees two theta±0.2 degrees two theta, an X-ray powder diffraction pattern substantially as depicted in FIG. 58, and combinations thereof;

h) Nilotinib hydrobromide form VIII, characterized by data selected from: an X-ray powder diffraction pattern having peaks at 8.5, 17.0, 19.2, 20.6 and 21.8 degrees two theta±0.2 degrees two theta, an X-ray powder diffraction pattern substantially as depicted in FIG. 64, and combinations thereof;

i) Nilotinib hydrobromide form IX, characterized by data selected from: an X-ray powder diffraction pattern having peaks at 16.9, 18.7, 20.9, 21.8 and 26.7 degrees two theta±0.2 degrees two theta, an X-ray powder diffraction pattern substantially as depicted in FIG. 65, and combinations thereof;

j) Nilotinib hydrobromide form X, characterized by data selected from: an X-ray powder diffraction pattern having peaks at 8.8, 15.5, 18.6, 22.2 and 24.2 degrees two theta±0.2 degrees two theta, an X-ray powder diffraction pattern substantially as depicted in FIG. 66, and combinations thereof; and k) Nilotinib hydrobromide form XI, characterized by data selected from: an X-ray powder diffraction pattern having peaks at 7.1, 14.1, 18.6, 21.9 and 22.5 degrees two theta±0.2 degrees two theta; an X-ray powder diffraction pattern substantially as depicted in FIG. 67, a solid state 13C NMR spectrum having signals at 129.8, 132.3 and 160.5±0.2 ppm, a solid-state 13C NMR spectrum having chemical shift differences between the signal exhibiting the lowest chemical shift in the chemical shift range of 100 to 180 ppm and another in the chemical shift range of 100 to 180 ppm of 23.0, 25.5 and 53.7±0.1 ppm, a solid state 13C NMR spectrum as depicted in any one of FIGS. 73-74, and combinations thereof.

8. The crystalline form XI of Nilotinib hydrobromide according to claim 7, characterized by an X-ray powder diffraction pattern having peaks at 7.1, 14.1, 18.6, 21.9 and 22.5 degrees two theta±0.2 degrees two theta.

9. The crystalline form XI of Nilotinib hydrobromide according to claim 8, further characterized by X-ray powder diffraction pattern having any one, two, three, four or five peaks selected from peaks at 9.0, 11.1, 13.8, 15.2 and 19.7 degrees two theta±0.2 degrees two theta.

10. The Nilotinib hydrobromide crystalline form according to claim 7, wherein the crystalline form is of Nilotinib monohydrobromide salt.

11. A crystalline form of Nilotinib succinate selected from:

a) Nilotinib succinate Form I, characterized by data selected from: an X-ray powder diffraction pattern having peaks at 4.5, 7.6, 11.3, 17.4 and 18.7 degrees two theta±0.2 degrees two theta, an X-ray powder diffraction pattern having peaks at 4.4, 7.6, 11.3, 17.3 and 18.7 degrees two theta±0.2 degrees two theta, an X-ray powder diffraction pattern substantially as depicted in FIG. 10, and combinations thereof;

b) Nilotinib succinate form II, characterized by data selected from: an X-ray powder diffraction pattern having peaks at 4.8, 9.5, 13.3, 19.2 and 21.0 degrees two theta±0.2 degrees two theta, an X-ray powder diffraction pattern substantially as depicted in FIG. 11, and combinations thereof; and c) Nilotinib succinate form III, characterized by data selected from: an X-ray powder diffraction pattern having peaks at 6.8, 9.0, 10.4, 15.3 and 19.4 degrees two theta±0.2 degrees two theta, an X-ray powder diffraction pattern substantially as depicted in FIG. 12, and combinations thereof.

12. Crystalline form I of Nilotinib glutamate, characterized by data selected from: an X-ray powder diffraction pattern having peaks at 4.5, 5.5, 7.5, 9.0 and 18.0 degrees two theta±0.2 degrees two theta; an X-ray powder diffraction pattern substantially as depicted in FIG. 24; and combinations thereof.

13. A crystalline form of Nilotinib acetate selected from:

a) Nilotinib acetate form I, characterized by data selected from: an X-ray powder diffraction pattern having peaks at 5.4, 7.6, 8.8 degrees two theta±0.2 degrees two theta and broad peaks having maxima at 18.4 and 24.5 degrees two theta±0.2 degrees two theta, an X-ray powder diffraction pattern substantially as depicted in FIG. 37, and combinations thereof;

b) Nilotinib acetate form II, characterized by data selected from: an X-ray powder diffraction pattern having peaks at 7.2, 7.8, 8.6, 10.9 and 13.6 degrees two theta±0.2 degrees two theta, an X-ray powder diffraction pattern substantially as depicted in FIG. 38, and combinations thereof;

c) Nilotinib acetate form III, characterized by data selected from: an X-ray powder diffraction pattern having peaks at 3.6, 6.7, 10.0, 15.8 and 21.2 degrees two theta±0.2 degrees two theta, an X-ray powder diffraction pattern substantially as depicted in FIG. 39, and combinations thereof;

d) Nilotinib acetate form IV, characterized by data selected from: an X-ray powder diffraction pattern having peaks at 4.7, 7.1, 9.5 and 14.9 degrees two theta±0.2 degrees two theta and a broad peak having a maximum at 14.1 degrees two theta±0.2 degrees two theta, an X-ray powder diffraction pattern substantially as depicted in FIG. 40, and combinations thereof;

e) Nilotinib acetate form V, characterized by data selected from: an X-ray powder diffraction pattern having peaks at 7.4, 11.3, 14.2, 14.9 and 19.1 degrees two theta±0.2 degrees two theta, an X-ray powder diffraction pattern substantially as depicted in FIG. 41, and combinations thereof; and f) Nilotinib acetate form VI, characterized by data selected from: an X-ray powder diffraction pattern having peaks at 6.4, 10.8, 17.7, 19.0 and 19.7 degrees two theta±0.2 degrees two theta, an X-ray powder diffraction pattern substantially as depicted in FIG. 42, and combinations thereof.

14. A crystalline form of Nilotinib L-malate, characterized by data selected from: an X-ray powder diffraction pattern having peaks at 4.5, 7.5, 9.3, 11.2 and 15.2 degrees two theta±0.2 degrees two theta; an X-ray powder diffraction pattern substantially as depicted in FIG. 43; and combinations thereof.

15. A crystalline form of Nilotinib maleate selected from:

a) Nilotinib maleate Form I, characterized by data selected from: an X-ray powder diffraction pattern having peaks at 7.5, 11.1, 15.3, 16.9 and 18.6 degrees two theta±0.2 degrees two theta; an X-ray powder diffraction pattern substantially as depicted in FIG. 32; and combinations thereof;
b) Nilotinib maleate Form II, characterized by data selected from: an X-ray powder diffraction pattern having peaks at 5.2, 10.4, 15.6, 21.0 and 25.6 degrees two theta±0.2 degrees two theta; an X-ray powder diffraction pattern substantially as depicted in FIG. 33; and combinations thereof;
c) Nilotinib maleate Form III, characterized by data selected from: an X-ray powder diffraction pattern having peaks at 7.4, 10.4, 14.9, 16.1 and 18.4 degrees two theta±0.2 degrees two theta; an X-ray powder diffraction pattern substantially as depicted in FIG. 34; and combinations thereof;
d) Nilotinib maleate Form IV, characterized by data selected from: an X-ray powder diffraction pattern having peaks at 5.6, 8.3, 10.1, 14.8 and 17.0 degrees two theta±0.2 degrees two theta; an X-ray powder diffraction pattern substantially as depicted in FIG. 36; and combinations thereof; and
e) Nilotinib maleate Form V, characterized by data selected from: an X-ray powder diffraction pattern having peaks at 9.7, 13.5, 16.6, 20.3 and 21.8 degrees two theta±0.2 degrees two theta; an X-ray powder diffraction pattern substantially as depicted in FIG. 57; and combinations thereof.

16. A method for treating chronic myelogenous leukemia (CML) in a patient comprising administering to the patient a nilotinib salt or a solid state form thereof according to any one of claims 7, 11, 14, or 15.

17. A pharmaceutical composition comprising the Nilotinib solid state form according to any one of claims 1, 7, 11-14, and 15, and at least one pharmaceutically acceptable excipient.

18. A method of treating a patient suffering from drug-resistant chronic myelogenous leukemia (CML), comprising administering to said patient an effective amount of the pharmaceutical composition according to claim 17.

19. A process for preparing Nilotinib HCl comprising preparing a Nilotinib solid state form according to any one of claims 1, 7, 11-14, and 15, and converting said Nilotinib solid state form to Nilotinib HCl.

20. A process according to claim 18, wherein the converting step comprises:
a. reacting the Nilotinib solid state form with HCl; or
b. reacting the Nilotinib solid state form with a base to obtain a Nilotinib base; and reacting the Nilotinib base with HCl.

21. A process for preparing Nilotinib base comprising preparing a Nilotinib solid state form according to any one of claims 1, 7, 11-14, and 15, and converting said solid state form to Nilotinib base.

22. Crystalline Form IV of Nilotinib maleate according to claim 15, characterized by an X-ray powder diffraction pattern having peaks at 5.6, 8.3, 10.1, 14.8 and 17.0 degrees two theta±0.2 degrees two theta.

23. Crystalline Form IV of Nilotinib maleate according to claim 22, further characterized by additional X-ray powder diffraction peaks at 12.1, 17.7, 18.7, 22.7 and 24.3 degrees two theta±0.2 degrees two theta.

24. Crystalline Form V of Nilotinib maleate according to claim 15, characterized by an X-ray powder diffraction pattern having peaks at 9.7, 13.5, 16.6, 20.3 and 21.8 degrees two theta±0.2 degrees two theta.

25. Crystalline Form V of Nilotinib maleate according to claim 24, further characterized by additional X-ray powder diffraction peaks at 10.6, 11.2, 14.5, 17.4 and 18.4 degrees two theta±0.2 degrees two theta.

26. Crystalline Form VI of Nilotinib L-tartrate according to claim 1, characterized by an X-ray powder diffraction pattern having peaks at 4.7, 12.1, 16.3, 21.0 and 24.4 degrees two theta±0.2 degrees two theta.

27. The crystalline Nilotinib L-tartrate Form VI according to claim 26, further characterized by data selected from: additional X-ray powder diffraction peaks at 8.1, 10.5, 13.5, 18.9 and 27.9 degrees two theta±0.2 degrees two theta; a solid state 13C NMR spectrum having signals at 118.7, 136.2 and 172.7±0.2 ppm; a solid-state 13C NMR spectrum having chemical shift differences between the signal exhibiting the lowest chemical shift in the chemical shift range of 100 to 180 ppm and another in the chemical shift range of 100 to 180 ppm of 12.0, 29.5 and 66.0±0.1 ppm; a solid state 13C NMR spectrum as depicted in any one of FIGS. 71-72; and combinations thereof.

28. The crystalline Nilotinib L-tartrate Form VI according to claim 26, wherein the crystalline form is anhydrous.

29. The crystalline Nilotinib L-tartrate Form VI according to claim 26, wherein the crystalline form is of Nilotinib mono L-tartrate salt.

* * * * *